(12) United States Patent
Dutta

(10) Patent No.: US 10,874,669 B2
(45) Date of Patent: Dec. 29, 2020

(54) NEUROPROTECTIVE AGENTS FOR TREATMENT OF NEURODEGENERATIVE DISEASES

(71) Applicant: WAYNE STATE UNIVERSITY, Detroit, MI (US)

(72) Inventor: Aloke K. Dutta, Troy, MI (US)

(73) Assignee: WAYNE STATE UNIVERSITY, Detroit, MI (US)

( * ) Notice: Subject to any disclaimer, the term of this patent is extended or adjusted under 35 U.S.C. 154(b) by 0 days.

(21) Appl. No.: 16/124,974

(22) Filed: Sep. 7, 2018

(65) Prior Publication Data

US 2019/0076426 A1  Mar. 14, 2019

(51) Int. Cl.
*A61K 31/497* (2006.01)
*A61K 31/496* (2006.01)
*A61P 25/16* (2006.01)
*A61P 25/28* (2006.01)

(52) U.S. Cl.
CPC ......... *A61K 31/497* (2013.01); *A61K 31/496* (2013.01); *A61P 25/16* (2018.01); *A61P 25/28* (2018.01)

(58) Field of Classification Search
CPC ..... A61K 31/497; A61K 31/496; A61P 25/16; A61P 25/28
See application file for complete search history.

(56) References Cited

U.S. PATENT DOCUMENTS

| | | | |
|---|---|---|---|
| 6,982,332 B2 | 1/2006 | Dutta | |
| 10,125,127 B2 * | 11/2018 | Dutta | A61K 31/496 |
| 2005/0032856 A1 | 2/2005 | Bennett, Jr. | |
| 2005/0032585 A1 | 10/2005 | Bennet | |
| 2006/0020132 A1 | 1/2006 | Dutta | |
| 2011/0046153 A1 | 2/2011 | Holger et al. | |
| 2012/0108815 A1 | 5/2012 | Wayne | |
| 2015/0299180 A1 * | 10/2015 | Dutta | A61K 31/496 544/364 |

FOREIGN PATENT DOCUMENTS

| | | | | |
|---|---|---|---|---|
| WO | 96/08228 A2 | 3/1996 | | |
| WO | 02/098367 A2 | 12/2002 | | |
| WO | WO-02098367 A2 * | 12/2002 | ........... | A61K 31/495 |
| WO | 2010/123995 A2 | 10/2010 | | |
| WO | 2014-085600 A1 | 6/2014 | | |

OTHER PUBLICATIONS

Biswas, S., "Further structure—activity relationships study of hybrid 7-{[2-(4-phenylpiperazin-1-y1) ethyl] propylamino}-5, 6, 7, 8-tetrahydronaphthalen-2-ol analogues: identification of a high-affinity D3-preferring agonist with potent in vivo activity with long duration of action." Journal of medicinal chemistry 51.1 (2007): 101-117.

Biswas, S. et al., "Bioisosteric Heterocyclic Versions of 7-{[2-(4-Phenyl-piperazin-1-yl)ethyl]propy Identification of Highly Potent and Selective Agonists for Dopamine D3 Receptor with Potent In Vivo Activity," J. Med. Che. 2008, 51, pp. 3005-3019.

Brown, D.A., "Investigation of various N-heterocyclic substituted piperazine versions of 5/7-{[2-(4-aryl-piperazin-1-y1)-ethyl1]-propyl-amino}-5, 6, 7, 8-tetrahydro-naphthalen-2-ol: Effect on affinity and selectivity for dopamine D3 receptor." Bioorganic & medicinal chemistry 17.11 (2009): 3923-3933.

Brown, D.A., "Structurally constrained hybrid derivatives containing octahydrobenzo [g or f] quinoline moieties for dopamine D2 and D3 receptors: binding characterization at D2/D3 receptors and elucidation of a pharmacophore model." Journal of medicinal chemistry 51.24 (2008): 7806.

(Continued)

*Primary Examiner* — John M Mauro
(74) *Attorney, Agent, or Firm* — Brooks Kushman P.C.

(57) ABSTRACT

A compound having formula IA is useful for treating a neurodegenerative disease:

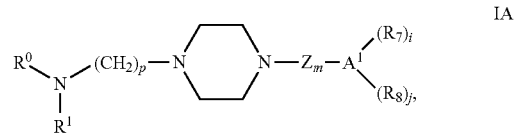

or a pharmaceutically acceptable salt or ester thereof, where $R^0$, $R^1$, $R^2$, $R^7$, $R^8$ are delineated substituents; $A^1$ is a $C_{6-12}$ aryl group, $C_{5-12}$ heteroaryl group, substituted 3-hydroxy-pyridin-4(1H)-one,

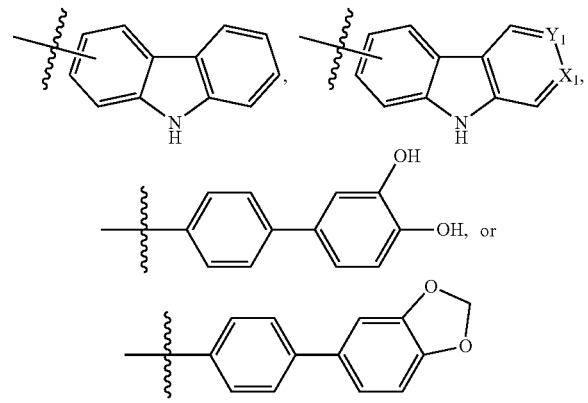

with i hydrogen atoms replaced with $R^7$ and j hydrogen atoms replaced with $R^8$; p is an integer from 1 to 6; $X^1$, $Y^1$ are each independently CH or N; M is absent or a divalent linking moiety in which Z is repeated m times; m is an integer from 0 to 5; i, j are each independently 0, 1, 2, or 3; and o is 0, 1, 2, 3, or 4.

18 Claims, 32 Drawing Sheets

(56) References Cited

OTHER PUBLICATIONS

Chen, J., "High-affinity and selective dopamine D 3 receptor full agonists." Bioorganic & medicinal chemistry letters 22.17 (2012): 5612-5617.
Dutta, A.K., "A novel series of hybrid compounds derived by combining 2-aminotetralin and piperazine fragments: Binding activity at D 2 and D 3 receptors," Bioorganic & Medicinal Chemistry Ltrs 12.4 (2002): 619-622.
Dutta, A.K., "Synthesis and biological characterization of novel hybrid 7-{[2-(4-phenyl-piperazin-1-y1)-ethyl]-propyl-amino}-5, 6, 7, 8-tetrahydro-naphthalen-2-ol and their heterocyclic bioisosteric analogues for dopamine D2 and D3 receptors," Bioorganic & Medicinal Chemistry, 12. 16 (2004), pp. 4361-4373.
Ghosh, B., "Development of (S)-N6-(2-(4-(Isoquinolin-1-yl) piperazine-1-yl) ethyl)-N6-propyl—4, 5, 6, 7-tetrahydrobenzo [d]-thiazole-2, 6-diamine and its analogue as a D3 receptor preferring agonist: Potent in vivo activity in Parkinson's disease animal models," J. of Medicinal Chemistry 53.3 (2010, p. 1023.
Ghosh, B., "Further delineation of hydrophobic binding sites in dopamine D 2/D 3 receptors for N-4 substituents on the piperazine ring of the hybrid template 5/7-{[2-(4-aryl-piperazin-1-y1)-ethyl]propyl-amino)-5, 6, 7, 8-tetrahydro-naphthalen-2-ol." Bioorganic & medicinal chemistry 18.15 (2010): 5661-5674.
Ghosh, B., "Discovery of 4-(4-(2-((5-hydroxy-1, 2, 3, 4-tetrahydronaphthalen-2-yl)(propyl) amino)-ethyl) piperazin-1-yl) quinolin-8-ol and its analogues as highly potent dopamine D2/D3 agonists and as iron chelator: In vivo activity indicates potential application in symptomatic and neuroprotective therapy for Parkinson's Disease," J. Med. Chem. 2010, 53, pp. 2114-2125.
Johnson, M. et al., Correction to Structure-Activity Relationship Study of N6-(2-(4-(1H-Indol-5-yl)piperazin-1-y1) ethyl)-N6-propyl-4,5,6,7-tetrahydrobenzol[d]thiazole-2,6-diamine Analogues: Development of Highly Selective D3 Dopamine Receptor Agonists along with a Highly Potent D2/D3 Agonist and Their Pharmacological Characterization, J. of J. Med. Chem., Jan. 4, 2013, 56, pp. 589-590.
Johnson, M. et al., "Structure-Activity Relationship Study of N6-(2(4-(1H-indol-5-yl)piperazin-1-yl)ethyl)-N6-propyl-4,5,6,7-tetrahydrobenzo[d]thiazole-2,6-diamine analogues: Development of highly selective D3 dopamine receptor agonists along with a highly potent D2/D3 agonist and their pharmacological characterization," J Med Chem. 2012, 55(12), pp. 5826-5840.
Kortagere, S., "Interaction of novel hybrid compounds with the D3 dopamine receptor: Site-directed mutagenesis and homology modeling studies." Biochemical pharmacology 81.1 (2011): 157-163.
Wang, C.H. et al., "Novel synthesis and functionalization of orth-ortho disubstituted biphenyls and a highly condensed novel heterocycle using radical cylization reaction," Tetrahedron 68 (2012, pp. 9750-9762.
International Search Report dated Mar. 5, 2014 from PCT/US2013/072253, filed Nov. 27, 2013, 3 pgs.
Partial Supplementary European Search Report dated Jun. 13, 2016 for EP Appn. No. 13859526.9, 2 pgs.
Dholkawala, F. et al., "Synthesis and characterization of brain penetrant prodrug of neuroprotective D-264: Potential Therapeutic application in the treatment of Parkinson's diseases," European J. of Pharmaceutics and Biopharmaceutics, 2016, v. 103, pp. 62-70.
Modi, G. et al., "Multifunctional D2/D3 agonist D-520 with high in vivo efficacy: modulator of toxicity of alpha-synuclein aggregates," ACS Chemical Neuroscience, 2014, v. 5, n. 8, pp. 700-717.
Modi, G. et al., "Understanding the structural requirements of hybrid (S)-6-((2-(4-phenylpiperazin-1-yl) ethyl) (propyl) amino)-5, 6, 7, 8-tetrahydronaphthalen-1-ol and its analogs as D2/D3 receptor ligands: a 3D QSAR investigation," Med. Chem. Comm., 2014, v. 5, n. 9, pp. 1384-1399.
Yedlapudi, D. et al., "Inhibition of alpha-synuclein aggregation by multifunctional dopamine agonists assessed by a novel in vitro assay and an in vivo *Drosophila synucleinopahty* model," Scientific Reports, 2016, v. 6, n. 38510, pp. 1-12.
Int'l Search Report dated Jan. 2, 2020 for PCT/US2019/049927 filed Sep. 6, 2019, 11 pgs.
Non-final Office Action dated Jul. 31, 2019 for U.S. Appl. No. 16/154,301, filed Oct. 8, 2018, 18 pgs.
Caplus-Registry Nos. 1027589-19-0, 1027223-61-5, and 80119-88-6, having database entry dates of Jun. 12, 2008, Jun. 11, 2008, and Nov. 16, 1984, respectively (entries accessed Jul. 17, 2019), p. 1.

\* cited by examiner

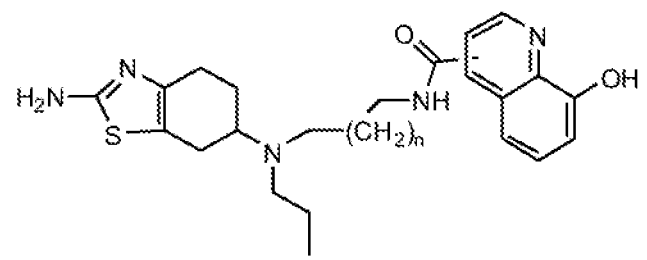
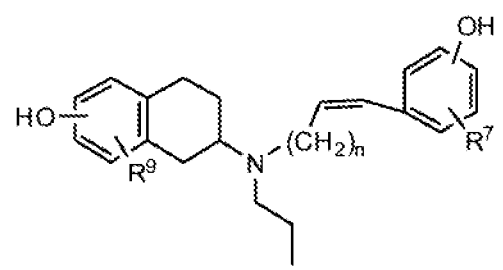
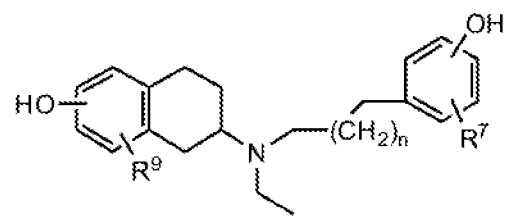
Fig. 8

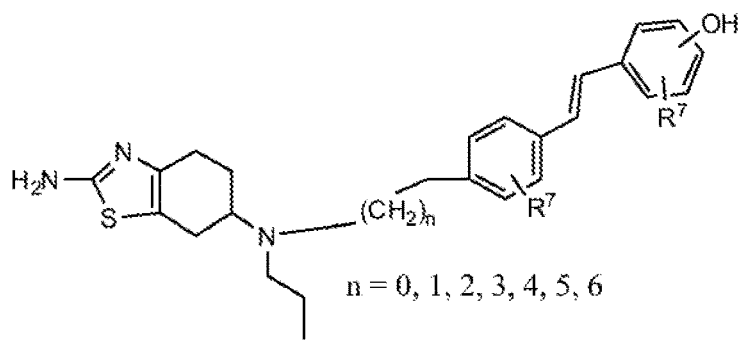
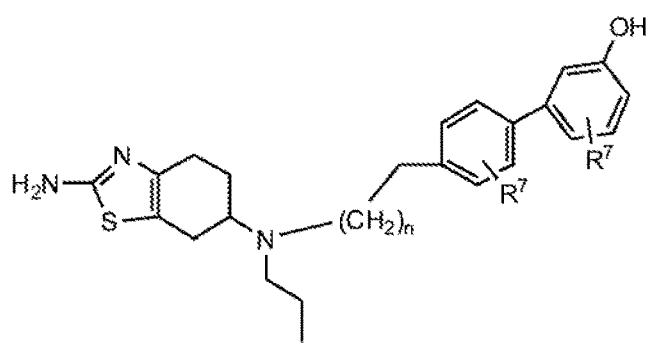
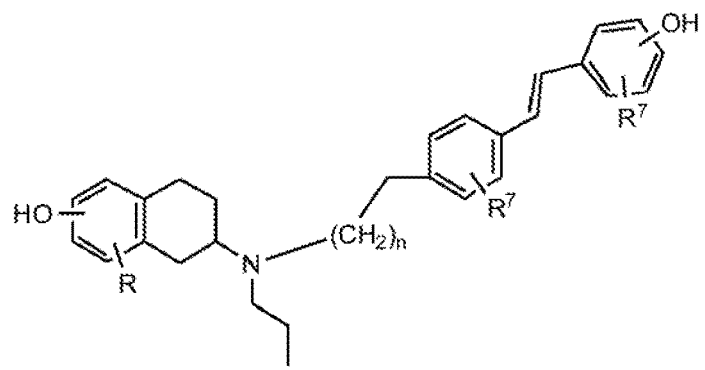
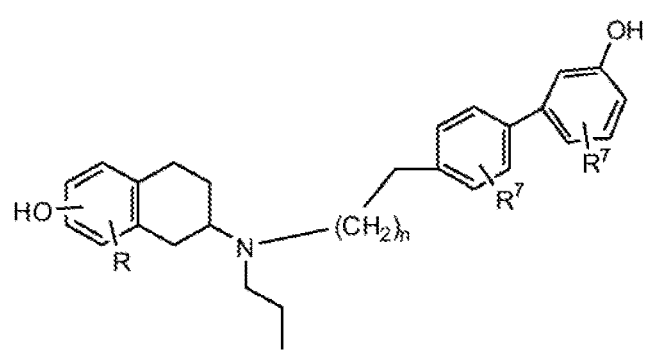
Fig. 9

Reagents and conditions: (a) triisopropylsilyl chloride, NaH, THF; (b) 4, PdCl$_2$[P(o-tol)$_3$]$_2$, NaOtBu, xylenes, reflux; (c) CF$_3$COOH, CH$_2$Cl$_2$; (d) (2-bromo-ethoxyl)-tert-butyl-dimethyl silane, K$_2$CO$_3$, CH$_3$CN, reflex; (e) (Boc)$_2$O, DMAP, THF; (f) n-Bu$_4$NF, THF; (g) (COCl)$_2$, DMSO Et$_3$N, CH$_2$Cl$_2$, -78 °C-rt; (h) (±), (-) or (+)-pramipexole, Na(OAc)$_3$BH, CH$_2$Cl$_2$; (i) CF$_3$COOH, CH$_2$Cl$_2$; (j) 2, Na(OAc)$_3$BH, CH$_2$Cl$_2$; (k) aq. HBr (48%), reflux.

Reaction and Conditions: (a) TPP, toluene, reflux, 16 h, 87%; (b) 1 M NaOH aq., 15 min, 88%; (c) vanillin, CHCl₃, reflux ,5 h, 85%; (d) TBDMSCl, imidazole, DMF, rt, 2 h, 90%; (e) DIBALH, THF, −10 ;æ to rt, 6 h, 94%; (f) MnO₂, DCM, rt, 24 h, 84%; (g) TBAF, THF, 0 ;æ, 1 h, 84%; (h) (±) Pramipexole, NaBH(OAc)₃, DCM, rt, 48 h, 30%.

Table 3. Inhibition constants determined by competition experiments assessing [$^3$H]spiroperidol binding to cloned rat $D_2$ and $D_3$ receptors expressed in HEK-293 cells [a]. cLogP values are calculated by using SwissADME data base and tPSA values are calculated by using ChemDraw.

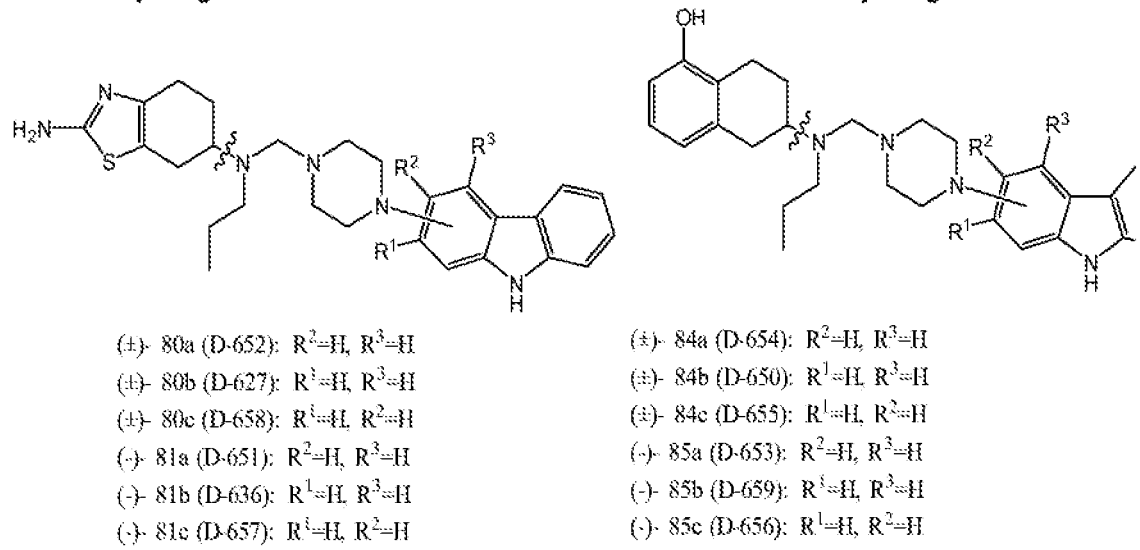

(±)- 80a (D-652): R$^2$=H, R$^3$=H
(±)- 80b (D-627): R$^1$=H, R$^3$=H
(±)- 80c (D-658): R$^1$=H, R$^2$=H
(-)- 81a (D-651): R$^2$=H, R$^3$=H
(-)- 81b (D-636): R$^1$=H, R$^3$=H
(-)- 81c (D-657): R$^1$=H, R$^2$=H (±)- 84a (D-654): R$^2$=H, R$^3$=H
(±)- 84b (D-650): R$^1$=H, R$^3$=H
(±)- 84c (D-655): R$^1$=H, R$^2$=H
(-)- 85a (D-653): R$^2$=H, R$^3$=H
(-)- 85b (D-659): R$^1$=H, R$^3$=H
(-)- 85c (D-656): R$^1$=H, R$^2$=H

| Compound | $K_i$ (nM) $D_{2L}$ [$^3$H]spiroperidol | $K_i$ (nM) $D_3$ [$^3$H]spiroperidol | $D_{2L}/D_3$ | cLogP | tPSA |
|---|---|---|---|---|---|
| (-)-5-OH-DPAT | 153 ± 32 | 2.07 ± 0.38 | 74 | | |
| Pramipexole | 6740 ± 510 | 11.7 ± 2.5 | 576 | | |
| (±)-80a | 902 ± 132 | 6.18 ± 0.91 | 146 | 4.30 | 60.13 |
| (±)-80b | 612 ± 92 | 3.12 ± 0.62 | 196 | 4.28 | 60.13 |
| (±)-80c | 76.9 ± 5.2 | 7.8 ± 1.17 | 9.86 | 4.31 | 60.13 |
| (-)-81a | 504 ± 50 | 3.94 ± 0.62 | 128 | 4.30 | 60.13 |
| (-)-81b | 135 ± 12 | 3.8 ± 0.38 | 35.4 | 4.28 | 60.13 |
| (-)-81c | 92.4 ± 8.5 | 4.18 ± 0.47 | 22.2 | 4.31 | 60.13 |
| (±)-84a | 62.1 ± 7.3 | 2.85 ± 0.62 | 21.8 | 4.89 | 41.98 |
| (±)-84b | 37.8 ± 4.7 | 1.87 ± 0.41 | 20.2 | 4.89 | 41.98 |
| (±)-84c | 29.4 ± 1.3 | 3.61 ± 0.28 | 8.13 | 4.83 | 41.98 |
| (-)-85a | 71.2 ± 9.6 | 0.400 ± 0.038 | 177 | 4.89 | 41.98 |
| (-)-85b | 61.6 ± 3.8 | 1.94 ± 0.18 | 31.8 | 4.89 | 41.98 |
| (-)-85c | 16.9 ± 1.9 | 0.362 ± 0.032 | 46.9 | 4.83 | 41.98 |
| (±)-90 | 435 ± 90 | 6.60 ± 1.13 | 65.9 | 4.41 | |
| (-)-91 | 82.6 ± 13.8 | 7.18 ± 0.86 | 11.5 | 5.11 | |

[a] Results are expressed as means ± SEM for 3-6 experiments each performed in triplicate

Fig. 24

Table 4. Stimulation of [$^{35}$S]GTPγS binding to cloned human $D_2$ and $D_3$ receptors expressed in CHO cells [a]

| Compound | hCHO-$D_2$ | | hCHO-$D_3$ | | $D_2/D_3$ |
| --- | --- | --- | --- | --- | --- |
| | $^{35}$S]GTPγS EC$_{50}$ (nM) | $E_{max}$ (%) | [$^{35}$S]GTPγS EC$_{50}$ (nM) | $E_{max}$ (%) | |
| Dopamine (DA) | 146 ± 24 | 100 | 1.95 ± 0.62 | 100 | 75.0 |
| (-)-5-OH-DPAT | 41 ± 6 | 80 ± 4 | 0.63 ± 0.08 | 75 ± 4 | 65 |
| Pramipexole | 251 ± 16 | 96.6 ± 4.9 | 4.08 ± 1.00 | 96.9 ± 0.8 | |
| (-)-81b | 48.7 ± 6.3 | 87.3 ± 2.1 | 0.96 ± 0.25 | 93.4 ± 4.4 | 50.7 |
| (-)-81c | 22.2 ± 6.9 | 56.7 ± 5.1 | 1.67 ± 0.30 | 82.0 ± 7.0 | 13.3 |
| (-)-85a | 0.87 ± 0.098 | 85.2 ± 4.7 | 0.23 ± 0.02 | 92.2 ± 3.3 | 3.79 |
| (-)-85c | 2.29 ± 0.70 | 73.6 ± 10.1 | 0.22 ± 0.06 | 87.9 ± 3.8 | 10.3 |

[a]EC$_{50}$ is the concentration producing half maximal stimulation. For each compound, maximal stimulation ($E_{max}$) is expressed as a percent of the $E_{max}$ observed with 1 mM ($D_2$) or 100 μM ($D_3$) of the full agonist DA ($E_{max}$, %). Results are the mean ± SEM for 3 – 6 experiments, each performed in triplicate.

Fig. 25

Reagents and conditions: a) Pd(PPh₃)₄, 2M K₂CO₃, THF, 90 °C, 12 h; b) PPh₃, 1,2-dichlorobenzene, 170 °C, 12 h; c) (Boc)₂O, 4-DMAP, THF, rt, overnight; d) 1-[2-(tert-butyl-dimethyl-silanyloxy)-ethyl]-piperazine, Pd(OAc)₂, BINAP, Cs₂CO₃, toluene, reflux, 24 h; e) n-Bu₄NF, THF, 0 °C to rt, 2 h; f) SO₃·py, CH₂Cl₂:DMSO (2:1), Et₃N, 0 °C to rt, 2 h; g) (±) or (-)-pramipexole, NaBH(OAc)₃, CH₂Cl₂, rt, 48 h; h) CF₃COOH, CH₂Cl₂, 0 °C to rt, 3 h.

Reagents and conditions: a) K$_2$CO$_3$, KOH, TBAB, DBE, 50 °C, overnight; b) 1-[2-(*tert*-butyl-dimeth silanyloxy)-ethyl]-piperazine, K$_2$CO3, CH$_3$CN, reflux, 24 h; c) *n*-Bu$_4$NF, THF, 0 °C to rt, 3 h; d) SO$_3$.py, CH$_2$Cl$_2$:DMSO (2:1), Et$_3$N, 0 °C to rt, 2 h; e) (±) or (-)-pramipexole, NaBH(OAc)$_3$, CH$_2$Cl$_2$, rt, 48 h.

Reagents and conditions: a) TBDMSCl, imidazole, CH2Cl2, rt, 20 h; b) K2CO3, CH3CN, reflux, overnight; c) Pd(PPh3)4, K2CO3, toluene, H2O, EtOH, reflux, 3 h; d) Pd(OAc)2, BINAP, Cs2CO3, toluene, reflux, 24 h; e) TBAF (1M in THF), THF, 0 °C to rt, 2 h; f) oxalyl chloride, DMSO, CH2Cl2, TEA, −80 °C to rt, 2 h; g) NaBH(OAc)3, CH2Cl2, rt, 48 h; h) 48% HBr, reflux, 6 h.

NEUROPROTECTIVE AGENTS FOR TREATMENT OF NEURODEGENERATIVE DISEASES

STATEMENT REGARDING FEDERALLY SPONSORED RESEARCH OR DEVELOPMENT

The invention was made with Government support under Contract No. NS047198 awarded by the National Institutes of Health/National Institute of Neurological Disorders and Stroke. The Government has certain rights to the invention.

TECHNICAL FIELD

The present invention relates to compounds for treating neurodegenerative diseases.

BACKGROUND OF THE INVENTION

Dopaminergic receptor systems have been targeted for the development of pharmacotherapeutic agents for a number of CNS related disorders, including drug addiction, schizophrenia, depression, and Parkinson's disease (PD). Dopamine (DA) receptor agonists have been employed more extensively in the treatment of Parkinson's disease than any other type of pharmacotherapy. Levodopa (L-dopa), the immediate precursor to endogenous DA, is the current gold-standard treatment option for PD. DA receptors belong to the family of transmembrane proteins known as G-protein-coupled receptors (GPCRs). DA receptors are widely distributed in the CNS, are also present in the periphery, and are divided into five subtypes. On the basis of the stimulatory action on adenylyl cyclase, D1 and D5 are grouped together as D1 type. D2-D4 receptors are classified as D2 type because of their inhibitory action on adenylyl cyclase activity. Interestingly, the D3 receptor was found to have a distribution in the brain that is somewhat different from that of the D2 receptor. The highest levels of D3 receptor expression were found to be in the limbic region of the brain, while D2 receptor expression is most dense in the striatum of the midbrain. D2 and D3 receptor subtypes occur post- and presynaptically. In the latter location they function as autoreceptors that regulate DA synthesis, metabolism, and release. It is noteworthy that D2 and D3 receptor subtypes share 50% overall amino acid sequence homology and 75-80% in their agonist binding sites. As a result, development of ligands selective for either subtype is a challenging task.

Parkinson's disease (PD) is a progressive, neurodegenerative disorder that results from the death of DA-producing cells in the substantia nigra region of the midbrain. Common symptoms include resting tremor, muscular rigidity, bradykinesia, postural instability, and cognitive psychiatric complications. Although the etiology of PD is not yet clear and may be multifactorial, oxidative stress and mitochondrial dysfunction are thought to play a central role in the pathology of the disease. Recent studies on various genetic mutations have provided new insights into the disease process. Oxidative stress has been strongly implicated in midbrain dopaminergic cell death. Toxicity from endogenous and exogenous origins, caused by oxidative mechanisms, has been implicated as a fundamental process in progressive nigral cell loss. Along with motor fluctuations and wearing off after long-term treatment, side effects associated with L-dopa treatment and the eventual oxidation of DA derived from L-dopa have been speculated to produce further oxidative stress.

In addition, α-synuclein, a presynaptic protein involved in fibrillization, has been implicated in the pathogenesis of PD. A recent report demonstrated that in cultured human dopaminergic neurons, accumulation of α-synuclein induces apoptosis in the presence of DA and reactive oxygen species. Furthermore, an interaction between calcium, cytosolic DA, and α-synuclein has been implicated in the loss of DA neurons in the substantia nigra. In this case, DAdependent neurotoxicity is mediated by a soluble protein complex containing α-synuclein. Therefore, α-synuclein, together with oxidized DA, could have synergistic effects in terms of disease susceptibility and progression.

Accordingly, there is a need for dopamine improved D2/D3 agonist molecules, and in particular, for improved D2/D3 agonist molecules with a capacity to bind to iron.

SUMMARY OF THE INVENTION

In at least one embodiment, the present invention solves one or more problems of the prior art by providing a compound having formula IA for treating a neurodegenerative disease:

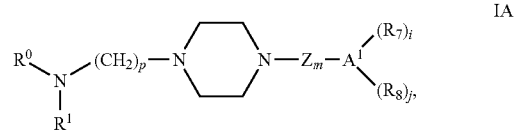

or a pharmaceutically acceptable salt or ester thereof, wherein
$R^0$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{6-10}$ aryl,

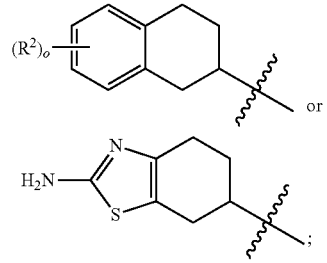

$R^1$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl;
$R^2$ are hydroxyl, $C_{1-4}$ alkyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, $-NR^3{}_q$ or $C_{1-10}$ hydrocarbon groups optionally containing one or more O, N, S, or Se heteroatoms where $R^3$ individually are H or organyl groups and q is 2 or 3, with the proviso that when q is 3, the group bears a positive formal charge;
$R^7$, $R^8$ are each independently, H, hydroxyl, oxo, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or $-NR^4{}_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;
$A^1$ is a $C_{6-12}$ aryl group, $C_{5-12}$ heteroaryl group, substituted 3-hydroxypyridin-4(1H)-one,

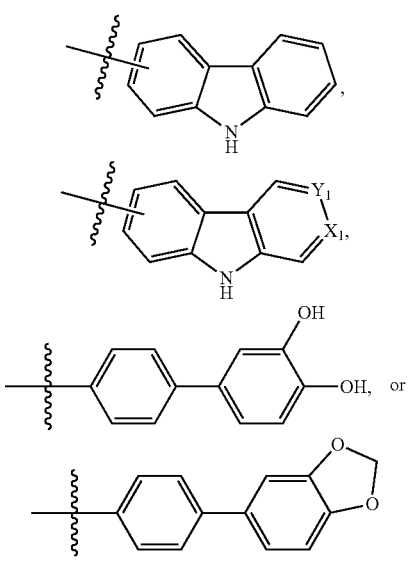

with i hydrogen atoms replaced with $R^7$ and j hydrogen atoms replaced with $R^8$;

p is an integer from 1 to 6;

$X^1$, $Y^1$ are each independently CH or N;

$Z_m$ is absent or a divalent linking moiety in which Z is repeated m times;

m is an integer from 0 to 5;

i, j are each independently 0, 1, 2, or 3; and o is 0, 1, 2, 3, or 4.

BRIEF DESCRIPTION OF THE DRAWINGS

Exemplary embodiments of the present invention will become more fully understood from the detailed description and the accompanying drawings, wherein:

FIGS. 7-10 provide examples of compounds having formula II;

FIG. 24. Table 3. Inhibition constants determined by competition experiments assessing [³H]spiroperidol binding to cloned rat $D_{2L}$ and $D_3$ receptors expressed in HEK-293 cells[a]. cLogP values are calculated by using SwissADME data base and tPSA values are calculated by using ChemDraw.

FIG. 25. Table 4. Stimulation of [³⁵S]GTPγS binding to cloned human $D_2$ and $D_3$ receptors expressed in CHO cells[a];

DETAILED DESCRIPTION OF THE INVENTION

Figure 1:
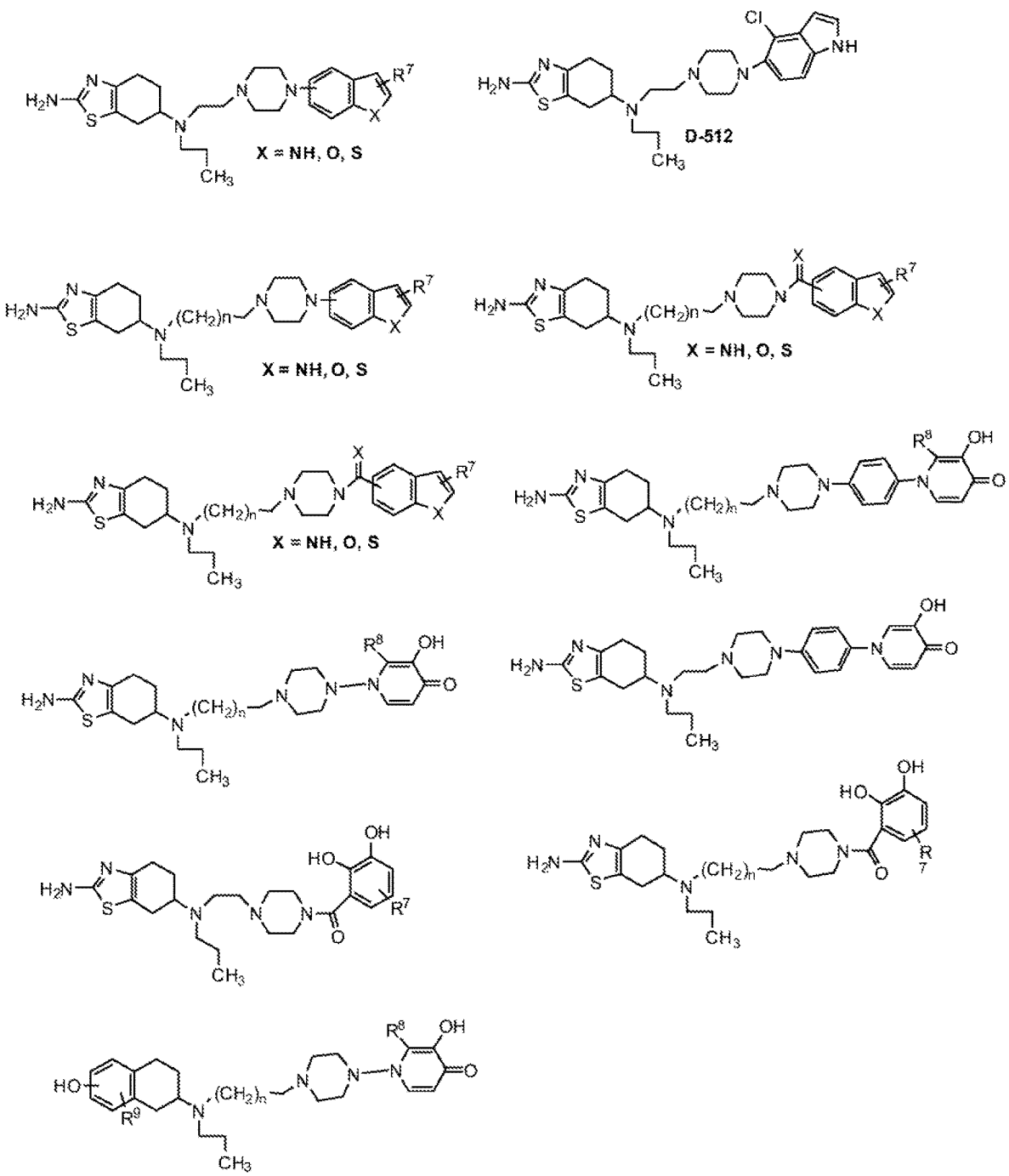
FIGS. 1-6 provide compounds having formula I.

Reference will now be made in detail to presently preferred compositions, embodiments and methods of the present invention, which constitute the best modes of practicing the invention presently known to the inventors. The Figures are not necessarily to scale. However, it is to be understood that the disclosed embodiments are merely exemplary of the invention that may be embodied in various and alternative forms. Therefore, specific details disclosed herein are not to be interpreted as limiting, but merely as a representative basis for any aspect of the invention and/or as a representative basis for teaching one skilled in the art to variously employ the present invention.

Except in the examples, or where otherwise expressly indicated, all numerical quantities in this description indicating amounts of material or conditions of reaction and/or use are to be understood as modified by the word "about" in describing the broadest scope of the invention. Practice within the numerical limits stated is generally preferred. Also, unless expressly stated to the contrary: percent, "parts of," and ratio values are by weight; all R groups and X or Y groups (as a substituent attached to a carbon e.g., replacing a potential C—H bond) include H, $C_{1-10}$ alkyl, $C_{2-10}$ alkenyl, halo, aryl, heteroaryl, and the like; all X, Y, Z symbols are X and Y may be N, CH, NR, O, S, and Se where R is hydrogen, alkyl, or aryl; all lower case letters (e.g., i, j, o, p, etc) are integers 0, 1, 2, 3, 4, 5, or 6; the first use of a symbol carries through to subsequent uses unless defined to the contrary; the description of a group or class of materials as suitable or preferred for a given purpose in connection with the invention implies that mixtures of any two or more of the members of the group or class are equally suitable or preferred; description of constituents in chemical terms refers to the constituents at the time of addition to any combination specified in the description, and does not necessarily preclude chemical interactions among the constituents of a mixture once mixed; the first definition of an acronym or other abbreviation applies to all subsequent uses herein of the same abbreviation; and, unless expressly stated to the contrary, measurement of a property is determined by the same technique as previously or later referenced for the same property.

It is also to be understood that this invention is not limited to the specific embodiments and methods described below, as specific components and/or conditions may, of course, vary. Furthermore, the terminology used herein is used only for the purpose of describing particular embodiments of the present invention and is not intended to be limiting in any way.

It must also be noted that, as used in the specification and the appended claims, the singular form "a," "an," and "the" comprise plural referents unless the context clearly indicates otherwise. For example, reference to a component in the singular is intended to comprise a plurality of components.

Throughout this application, where publications are referenced, the disclosures of these publications in their entireties are hereby incorporated by reference into this application to more fully describe the state of the art to which this invention pertains.

In a variation, the term "organyl group" means any organic substituent group, regardless of functional type, having one free valence at a carbon atom, e.g. methyl, ethyl, propyl, butyl, pyridinyl, 4-pyridylmethyl, and the like.

In a variation, the term "alkyl" means a straight or branched hydrocarbon radical having from 1 to 10 carbon atoms and includes, for example, methyl, ethyl, n-propyl, isopropyl, n-butyl, sec-butyl, isobutyl, tert-butyl, n-pentyl, n-hexyl, n-heptyl, n-octyl, and the like.

In a variation, the term "alkanediyl" means a straight or branched hydrocarbon diradical having from 1 to 10 carbon atoms formed by removing 2 hydrogen atoms from an alkane.

In a variation, the term "alkoxy" and "thioalkoxy" are O-alkyl or S-alkyl of from 1 to 8 carbon atoms as defined above for "alkyl".

In a variation, the term "cycloalkyl" means a saturated hydrocarbon ring having 3 to 8 carbon atoms and includes, for example, cyclopropyl, cyclobutyl, cyclopentyl, cyclohexyl, cycloheptyl, cyclooctyl, and the like.

In a variation, the term "alkenyl" means a straight or branched unsaturated hydrocarbon radical having from 2 to 12 carbon atoms and includes, for example, ethenyl, 2-propenyl, 1-butenyl, 2-butenyl, 1-pentenyl, 2-pentenyl, 3-methyl-3-butenyl, 1-hexenyl, 2-hexenyl, 3-hexenyl, 3-heptenyl, 1-octenyl, 1-nonenyl, 1-decenyl, 1-undecenyl, 1-dodecenyl, and the like.

In a variation, the term "alkenediyl" means a straight or branched hydrocarbon diradical having from 2 to 12 carbon atoms formed by removing 2 hydrogen atoms from a $C_{2-12}$ alkene.

In a variation, the term "alkynyl" means a straight or branched triple bonded unsaturated hydrocarbon radical having from 2 to 12 carbon atoms and includes, for example, ethynyl, 2-propynyl, 3-butynyl, 4-pentynyl, 5-hexynyl, 6-heptynyl, 7-octynyl, 8-nonynyl, 9-decynyl, 10-undecynyl, 11-dodecynyl, and the like.

In a variation, the term "alkynediyl" means a straight or branched hydrocarbon diradical having from 2 to 12 carbon atoms formed by removing 2 hydrogen atoms from a $C_{2-12}$ alkyne.

In a variation, the term "cycloalkylalkyl" means a saturated hydrocarbon ring attached to an alkyl group wherein alkyl is as defined above. The saturated hydrocarbon ring contains from 3 to 12 carbon atoms. Examples of such are cyclopropylmethyl, cyclopentylmethyl, cyclohexylmethyl, adamantylmethyl and the like.

In a variation, the term "heterocycloalkyl" means a saturated hydrocarbon ring having 3 to 8 carbon atoms in which 1 or more carbon atoms are replaced by N, S, O, Se, etc. Examples includes 2- or 3-tetrahydrothieno, 2- or 3-tetrahydrofurano, 2- or 3-pyrrolidino, 2-, 4-, or 5-thiazolidino, 2-, 4-, or 5-oxazolidino, 2-, 3-, or 4-piperidino, N-morpholinyl or N-thiamorpholinyl.

In a variation, the term "aryl" means an aromatic radical such as a phenyl group, a naphthyl group, a phenyl group substituted by 1 to 4 substituents selected from alkyl as defined above, alkoxy as defined above, thioalkoxy as defined above, hydroxy, halogen, trifluoromethyl, amino, alkylamino as defined above for alkyl, dialkylamino as defined for alkyl, N-acetylamino, cyano —$SO_2NH_2$, or nitro, or a naphthyl group substituted by 1 to 4 substituents as defined above for a phenyl group substituted by 1 to 4 substituents. In a refinement, aryl is a $C_{6-14}$ aryl.

In a variation, the term "heteroaryl" means a $C_{5-13}$ heteroaromatic radical such as 2- or 3-thienyl; 2- or 3-furanyl; 1-, 2- or 3-pyrrolyl; 1-, 2-, 4-, or 5-imidazolyl; 1-, 3-, 4-, or 5-pyrazolyl; 2-, 4-, or 5-thiazolyl; 3-, 4-, or 5-isothiazolyl; 2-, 4-, or 5-oxazolyl; 3-, 4-, or 5-isoxazolyl; 1-, 3-, or 5-1,2,4-triazolyl; 1-, 2-, 4-, or 5-1,2,3-triazolyl; 1- or 5-tetrazolyl; 4-, or 5-1,2,3-oxadiazolyl; 3-, or 5-1,2,4-oxadiazolyl; 2-1,3,4-oxadiazolyl; 2-1,3,4-thiadiazoyl; 2-1,3,5-triazinyl; 3-pyridinyl; 3-, 4-, or 5-pyridazinyl; 2-pyrazinyl; 2-, 4-, or 5-pyrimidinyl; unsubstituted or substituted by 1 to 2 substituents selected from NH$_2$, OH, S, halogen as defined hereinafter, alkyl as defined above, or alkoxy as defined above. In a refinement, heteroaryl is a C$_{5-10}$ heteroaryl.

In a variation, the term "halogen" or "halo" means fluorine, chlorine, bromine, or iodine.

It should be appreciated that each C—H bond in the formulae set forth herein can be substituted. For example, each C—H bond can be substituted by halo, cyano, nitro, hydroxyl, C$_{1-10}$ alkyl, C$_{1-8}$ alkoxyl, C$_{6-14}$ aryl, C$_{5-13}$ heteroaryl, NH$_2$SO$_2$R, CF$_3$, arylsulfonyl, arylsulfonamide, o-OCH$_3$, pyridinyl, bipyridinyl, phenyl, chloro, bromo, fluoro, and the like. Such substituted C—H bonds can be symbolized by C—R$^z$ where z is an integer from 1 to 100 that has not already been used as a subscript or subscript for an R group.

It should also be appreciated that integer ranges explicitly include all intervening integers. For example, the integer range 1-10 explicitly includes 1, 2, 3, 4, 5, 6, 7, 8, 9, and 10. Similarly, the range 1 to 100 includes 1, 2, 3, 4 . . . 97, 98, 99, 100.

Abbreviations

"h" is hour;
"s" is seconds;
"rt" is room temperature;
"et" is ethyl;
"me" is methyl;
"BOC" is Di-tert-butyl dicarbonate;
"TBDMS" is tert-butyldimethylsilyl;
"THF" is tetrahydrofuran;
"DMSO" is dimethylsulfoxide;
"DMAP" is 4-dimethylaminopyridine;
"TFA" is trifluoroacetic acid;
"DCE" is 1,2-dichloroethane;
"tol" is tolyl;
"DIBALH" is diisobutylaluminium hydride;
"DCM" is dichloromethan;
"DMF" is dimethylformamide;
"TBAF" is tetra-n-butylammonium fluoride;
"NaHMDS" is sodium bis(trimethylsilyl)amide; and
"PCC" is pyridinium chlorochromate.
"Cs$_2$CO$_3$" means cesium carbonate.
"BINAP" means 2,2'-bis(diphenylphosphino)-1,1'-binaphthyl
"Pd(OAc)2" means palladium(II) acetate.
"TBAF" means tetrabutylammonium fluoride.
"SO$_3$.py" means sulfur trioxide pyridine.
"NaBH(OAc)3" means sodium triacetoxyborohydride.
"GTPγS" means guanosine 5'-O-[gamma-thio]triphosphate.
"5-OH-DPAT" means 5-hydroxy-2-(dipropylamino)tetralin.
"CHO" means chinese hamster ovary.
"HEK" means human embryonic kidney.
"L-DOPA" means (S)-(3,4-dihydroxyphenyl) alanine.
"i.p." means intraperitoneal.
"s.c." means subcutaneous.
"PD: Parkinson's disease.
"DA" means dopamine.

In at least one embodiment, the present invention provides a compound having formula I for treating a neurodegenerative and other related CNS diseases:

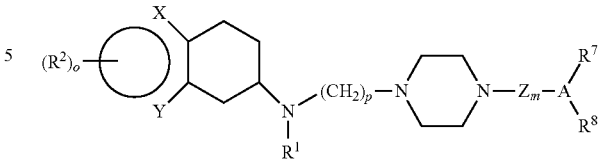

I

R$^1$ is a C$_{1-12}$ organyl group, preferably selected from among optionally substituted C$_{1-8}$ alkyl, C$_{1-8}$ alkoxyl, C$_{2-8}$ alkenyl, C$_{2-8}$ alkynyl, C$_{4-8}$ cycloalkyl, C$_{4-8}$ cycloalkenyl, or C$_{6-10}$ aryl, each of the foregoing alkyl, alkenyl, alkynyl, cycloalkyl, etc. groups optionally halo substituted, preferably fluoro and/or chloro substituted, or substituted by C$_{1-4}$ alkoxy, C$_{1-8}$ alkoxy C$_{1-4}$ acyloxy, C$_{1-4}$ acyl, —C(O)—R$^4$, or —R$^5$—NH—SO$_2$—NR$^4{}_r$, —R$^5$—NH—C(O)—R$^4$, —R$^5$—NR$^4{}_r$, or —R$^5$—Ar where R$^4$ is H or C$_{1-12}$ organyl groups, preferably H, C$_{1-8}$ alkyl, C$_{2-8}$ alkenyl, C$_{4-8}$ cycloalkyl, C$_{4-8}$ cycloalkenyl, or C$_{6-10}$ aryl; and R$^5$ is C$_{1-8}$ alkenyl, and r is 2 or 3, with the proviso that when r is 3, the nitrogen of the NR$^4{}_r$ group will bear a positive formal charge. When there is a formal charge, the compound includes a suitable negatively charged counter ion such as chloride, bromide, and the like. Ar is a C$_{6-10}$ aryl ring system, preferably a C$_{6-10}$ aryl ring system, optionally including one or more heteroatoms or a C$_{5-10}$ C$_{5-12}$ heteroaryl. Preferably Ar is phenyl, thienyl, pyridyl, biphenyl, or naphthyl each optionally substituted with CN, halo, C$_{1-8}$ alkyl, C$_{2-8}$ alkenyl, C$_{4-8}$ cycloalkyl, C$_{4-8}$ cycloalkenyl, or C$_{6-10}$ aryl;

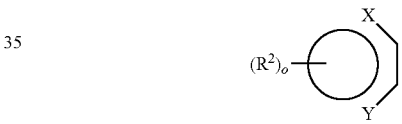

is a C$_{6-12}$ aromatic ring system, C$_{5-12}$ heteroaromatic ring system and/or an optionally heterocyclic ring system containing 5 to 12 ring atoms and up to three heteroatoms individually selected from the group consisting of N, O, S, and Se. When the ring system includes 0 heteroatoms, the ring system is formally a C$_{5-12}$ carbon ring system (e.g., a cycloalkyl). In a refinement, this rings systems are fused to each other or to an aromatic ring. They also are linked together or to an aromatic ring. In another variation, this moiety is an optionally heterocyclic ring system containing 5 or 6 ring atoms and up to three heteroatoms individually selected from the group consisting of N, O, S, and Se. This C$_{6-12}$ aromatic ring system, C$_{5-12}$ heteroaromatic ring system and/or an optionally heterocyclic ring system is optionally substituted by o R$^2$ groups, where o is 0, 1, 2, 3, or 4, the upper limit bounded by the number of available substituent sites. In a variation, X and Y may be N, CH, NR, O, S, and Se where R is hydrogen, alkyl, or aryl;

R$^2$ are C$_{1-12}$ organyl groups, hydroxyl, nitro, or —NR$^4{}_q$ where R$^4$ is H, C$_{1-8}$ alkyl, C$_{2-8}$ alkenyl, C$_{4-8}$ cycloalkyl, C$_{4-8}$ cycloalkenyl, or C$_{6-10}$ aryl. In a variation, R$^2$ are C$_{1-10}$ hydrocarbon groups optionally containing one or more O, N, S, or Se heteroatoms. In another variation, R$^2$ are selected from among C$_{1-4}$ alkyl, C$_{1-4}$ alkoxyl, C$_{1-8}$ alkyl, C$_{2-8}$ alkenyl, C$_{2-8}$ alkynyl, C$_{4-8}$ cycloalkyl, C$_{4-8}$ cycloalkenyl; C$_{6-10}$ aryl, —NR$^3{}_q$ where R$^3$ individually are H or organyl groups. For example, R$^3$ may be H, C$_{1-8}$ alkyl, C$_{1-8}$ alkoxyl, C$_{2-8}$ alkenyl, C$_{2-10}$ alkynyl, C$_{4-8}$ cycloalkyl, C$_{4-8}$ cycloalkenyl, $C_{6-10}$ aryl and q is 2 or 3, with the proviso that when q is 3, the group bears a positive formal charge; —NH—C(O)—$R^3$, —NH—C(O)—$NR^4_2$, and related compounds wherein the hydrocarbon groups in each case may optionally be substituted with —CN, $C_{1-4}$ alkyl, $C_{1-8}$ alkyl, —$OR^3$, —OH, halo, particularly fluoro and/or chloro, —$CF_3$, and the like. Two $R^2$ may also together form an alicyclic or aromatic fused five or six membered ring, optionally containing heteroatoms O, N, S, or Se. $R^3$ may also be arylsulfonyl, preferably 4-chlorophenylsulfonyl, 3,4-dichlorophenylsulfonyl; 4-(trifluoromethyl)phenylsulfonyl; $X^4$—Ar—$SO_2$ where $X^4$ is an electron withdrawing or electron donating substituent and Ar is a $C_{6-10}$ aromatic or $C_{5-10}$ heteroaromatic moiety; or keto, preferably phenylketo, 4-(trifluoromethyl)phenylketo, or aceto;

$R^7$, $R^8$ are each independently, hydrogen (H), hydroxyl, oxo (i.e., carbonyl), $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo (e.g. fluoro or chloro), $C_{1-4}$ aldehyde, or —$NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl and like groups where $R^4$ is H or $C_{1-12}$ organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl. In a variation, $R^7$, $R^8$ are not hydroxyl;

A is a $C_{6-12}$ aryl group, $C_{5-12}$ heteroaryl group, or an optionally substituted 3-hydroxypyridin-4(1H)-one. In one variation, A contains one or more heteroatoms. In another variation, A may be directly bonded to a nitrogen atom of the piperazinyl group. In still another variation, A is an $C_{6-12}$ group consisting of 1 to 4 rings, may contain heterocyclic rings, optionally fused, optionally linked, and optionally substituted by $C_{1-4}$ alkyl, $C_{1-4}$ alkoxyl, $C_{1-4}$ alkyl, $C_{1-8}$ alkoxyl, $C_{2-4}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, —$NR^4_q$ and like groups where $R^4$ is H or organyl groups, preferably H, $C_{1-8}$ alkyl, $C_{2-8}$ alkenyl, $C_{4-8}$ cycloalkyl, $C_{4-8}$ cycloalkenyl, or $C_{6-10}$ aryl; and q is 2 or 3, with the proviso that when q is 3, the group bears a positive formal charge. It should be noted that unsaturated groups such as alkenyl and cycloalkenyl include multiply unsaturated groups such as alkadienyl and cycloalkadienyl. Alkyl and cycloalkyl groups herein also include aryl-substituted alkyl and cycloalkyl groups, while aryl groups also include alkyl and cycloalkyl-substituted aryl groups. In a variation, A is optionally substituted thienyl, pyridyl, bipyridyl, phenyl, biphenylyl, or naphthyl, more preferably phenyl and biphenyl, quinolone, indole, and isoquinoline. Preferred substituents include $C_{1-4}$ alkyl, $C_{1-8}$ alkyl, —CN, halo, $C_{1-8}$ alkoxyl, $C_{1-4}$ alkoxyl, and $NH_2SO_2R^3$, $CF_3$, arylsulfonyl, arylsulfonamide, etc., more preferably o-$OCH_3$, 2,3-dichloro, and p-$NHSO_2CH_3$;

p is an integer from 1 to 6; and $Z_m$ is absent or a divalent linking moiety in which Z is repeated m times. Examples of Z include —$CH_2$—, —CO—, —N—$CH_2$— or —N—CO—, where m is an integer from 0 to 5. In another variation, m is an integer from 0 to 2. In a refinement, m is 0, 1, 2, 3, 4, or 5 and p is 1, 2, 3, 4, 5, or 6. In a refinement, $Z_m$ is $(CH_2)_n$, $(CH_2)_nCO$, $(CH_2)_nNCO(CH_2)_k$, $C_{1-10}$ carboximido, $C_{1-10}$ alkyl (i.e., an $C_{1-10}$ alkanediyl), $C_{2-10}$ alkenyl (i.e., an $C_{2-10}$ alkanediyl), $(CH_2)_nCH=CH(CH_2)_k$, $(CH_2)_nCC(CH_2)_k$, $C_{2-10}$ alkynyl (i.e., an $C_{2-10}$ alkynediyl), where n and k are integers from 0 to 8.

FIGS. 1-6 provide examples of compound falling within the present embodiment. In these Figures, n is 0 to 8 and more particularly, n is 0, 1, 2, 3, 4, 5, or 6. $R^7$, $R^8$ are as set forth above. In particular, $R^7$, $R^8$ and $R^9$ is hydrogen (H), hydroxyl, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, —$NR^4_q$ and like groups where $R^4$ is H or organyl groups, preferably H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl. The present embodiment provides variations of the compounds set forth in U.S. Pat. No. 20120108815, the entire disclosure of which is hereby incorporated by reference.

In a variation, the compound having formula I is described by formula IA:

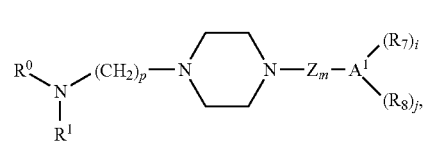

or a pharmaceutically acceptable salt or ester thereof, wherein:

$R^0$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{6-10}$ aryl, or

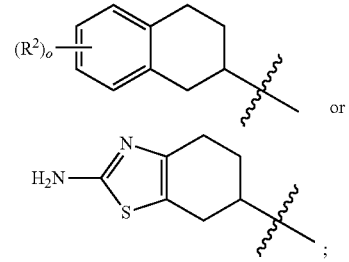

$R^1$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl;

$R^2$ are hydroxyl, $C_{1-4}$ alkyl, $C_{1-4}$ alkoxyl, $C_{1-8}$ alkyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^3_q$ or $C_{1-10}$ hydrocarbon groups optionally containing one or more O, N, S, or Se heteroatoms where $R^3$ individually are H or organyl groups and q is 2 or 3, with the proviso that when q is 3, the group bears a positive formal charge;

$R^7$, $R^8$ are each independently, H, hydroxyl, oxo, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, $C_{1-4}$ aldehyde, or —$NR^4_q$ where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

$A^1$ is a $C_{6-12}$ aryl group, $C_{5-12}$ heteroaryl group, substituted 3-hydroxypyridin-4(1H)-one,

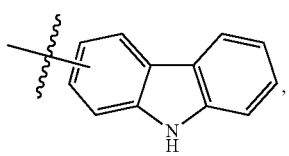

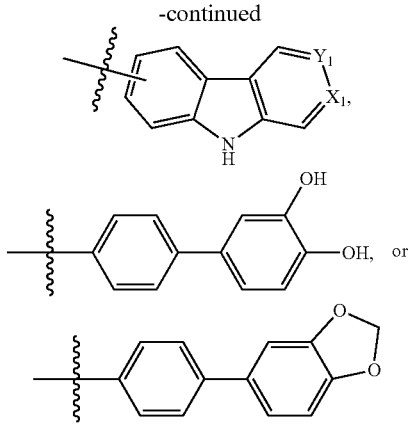

with i hydrogen atoms replaced with $R^7$ and j hydrogen atoms replaced with $R^8$;

p is an integer from 1 to 6;

$X^1$, $Y^1$ are each independently CH or N;

$Z_m$ is absent or a divalent linking moiety in which Z is repeated m times.

m is an integer from 0 to 5;

i, j are each independently 0, 1, 2, or 3; and o is 0, 1, 2, 3, or 4.

In some refinements, $A^1$ is:

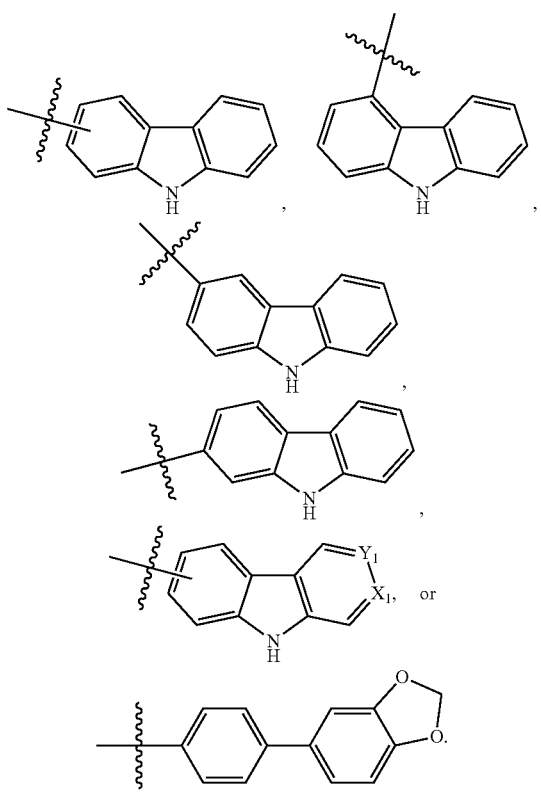

In further refinements, $R^1$ is substituted with a component selected from the group consisting of $C_{1-8}$ alkoxy, $C_{1-4}$ acyloxy, $C_{1-4}$ acyl, —C(O)—$R^4$, and —$R^5$—NH—SO$_2$—N$R^4_r$, where $R^5$—NH—C(O)—$R^4$; —$R^5$—N$R^4_r$, or —$R^5$—Ar where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl; $R^5$ is $C_{2-8}$ alkenyl; r is 2 or 3; and Ar is a $C_{6-10}$ aryl ring system, optionally including one or more heteroatoms or $C_{5-10}$ heteroaryl; with the proviso that when r is 3, the nitrogen of the $NR^4_r$ group will bear a positive formal charge. In a refinement, Ar is an optionally substituted phenyl, thienyl, pyridyl, bipyridyl, biphenylyl, or naphthyl.

In further refinements, $R^2$ are hydroxyl, $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl; $C_{6-10}$ aryl, —$NR^3_q$—NH—C(O)—$R^3$, or —NH—C(O)—$NR^4_2$, where $R^3$ individually are H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl where q is 2 or 3, with the proviso that when q is 3, the group bears a positive formal charge and wherein the hydrocarbon groups in each case are optionally substituted with —CN, $C_{1-8}$ alkyl, —$OR^3$, —OH, halo, or —CF$_3$.

In some variations, $A^1$ is a $C_{6-12}$ aryl group consisting of 1 to 4 rings or a $C_{5-12}$ heteroaryl optionally linked, and optionally substituted by $C_{1-4}$ alkyl, $C_{2-4}$ alkenyl, $C_{2-10}$ alkynyl, $C_{5-7}$ cycloalkyl, $C_{5-7}$ cycloalkenyl, halo, $C_{1-4}$ aldehyde, or —$NR^4_q$, where $R^4$ is $C_{1-8}$ alkyl, OH, $C_{1-8}$ alkoxyl, $C_{2-8}$ alkenyl, $C_{4-8}$ cycloalkyl, $C_{4-8}$ cycloalkenyl, or $C_{6-10}$ aryl; and q is 2 or 3, with the proviso that when q is 3, the group bears a positive formal charge. In a refinement, $A^1$ is an optionally substituted thienyl, pyridinyl, phenyl, biphenyl, naphthyl, quinolone, indole, or isoquinoline. For example, A can be substituted with $C_{1-8}$ alkyl, —CN, halo, OH, $C_{1-8}$ alkoxyl, NH$_2$SO$_2$R$^3$, CF$_3$, arylsulfonyl, arylsulfonamide, o-OCH$_3$, 2,3-dichloro, pyridinyl, bipyridinyl, or p-NHSO$_2$CH$_3$.

In other refinements, $R^1$, $R^2$, $R^7$, $R^8$, Z, $Z_m$, m, o, p, X, Y, and $A^1$ for formula IA are the same as set forth above for formula I with $A^1$ being A.

A variation of the compounds having formula I are described by formula IB and IC:

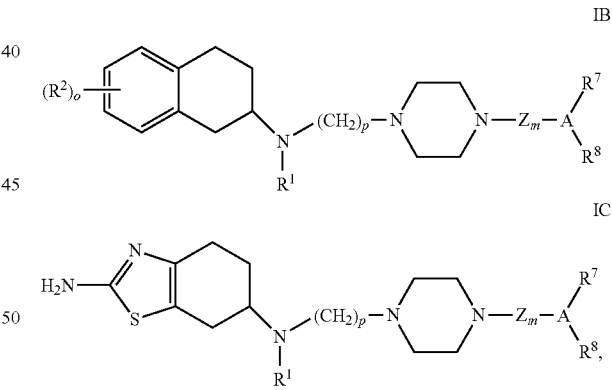

where $R^1$, $R^2$, $R^7$, $R^8$, Z, $Z_m$, m, o, p, X, Y, and A are the same as set forth above for formula I and IA.

In another embodiment, a compound having formula II for treating neurodegenerative and other related CNS diseases is provided:

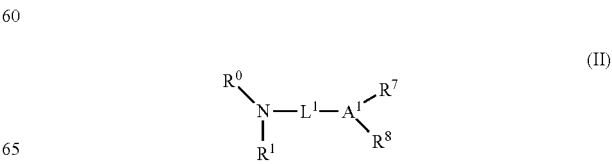

where $R^0$, $R^1$, $R^2$, $R^7$, $R^8$, o, p, i, j, X, Y, and $A^1$ are the same as set forth above. $L^1$ is a linking group. In a refinement, $L^1$ is $(CH_2)_n$, $(CH_2)_nCO$, $(CH_2)_nNCO(CH_2)_k$, $C_{1-10}$ carboximido, $C_{1-10}$ alkyl (i.e., an $C_{1-10}$ alkanediyl), $C_{2-10}$ alkenyl (i.e., an $C_{2-10}$ alkanediyl), $(CH_2)_nCH=CH(CH_2)_k$, $(CH_2)_nCC(CH_2)_k$, $C_{2-10}$ alkynyl (i.e., an $C_2$-10 alkynediyl), where n and k are integers from 0 to 8; and $R^7$, $R^8$ each independently, hydrogen (H), hydroxyl, $C_{1-8}$ alkyl, $C_{2-8}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, $-NR^4_q$ and like groups where $R^4$ is H or organyl groups, preferably H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl. In a refinement, n and k are each independently, 0, 1, 2, 3, 4, 5, 6, 7, and 8.

Figure 11:
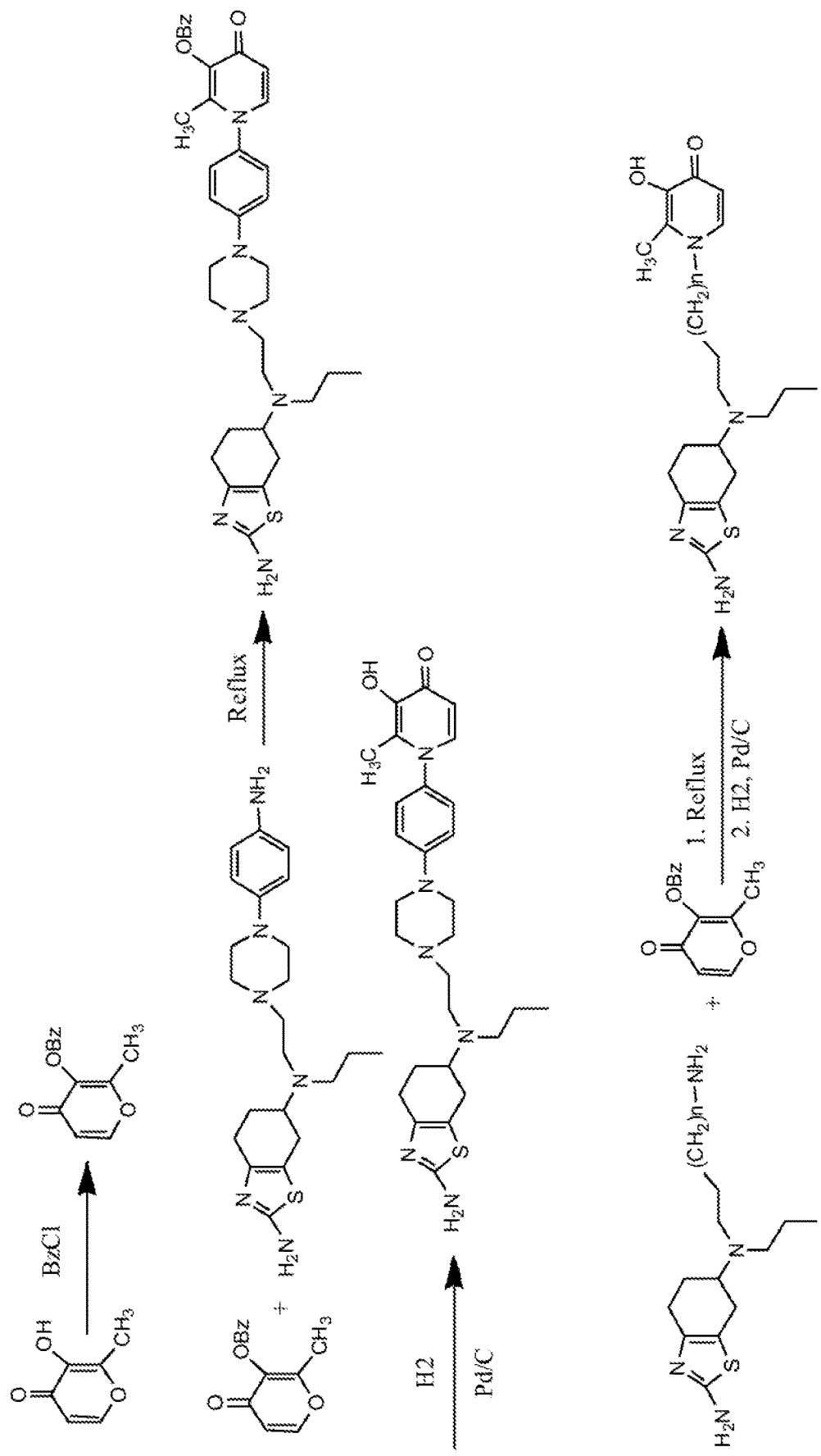
FIG. 11 provides a synthetic scheme for compounds having formula II.

FIGS. 7-10 provide examples of the compounds having formula II while FIG. 11 provides a synthetic scheme. In these Figures, n is 0 to 8 and more particularly, n is 0, 1, 2, 3, 4, 5, or 6. $R^7$, $R^8$ are as set forth above. In particular, $R^7$, $R^8$, $R^9$ is hydrogen (H), hydroxyl, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, halo, preferably fluoro or chloro, $C_{1-4}$ aldehyde, $-NR^4_q$ and like groups where $R^4$ is H or organyl groups, preferably H, $C_{1-8}$ alkyl, $C_{2-8}$ alkenyl, $C_{2-10}$ alkynyl, $C_{4-8}$ cycloalkyl, $C_{4-8}$ cycloalkenyl, or $C_{6-10}$ aryl.

A variation of the compounds having formula II are described by formula IIA and IIB:

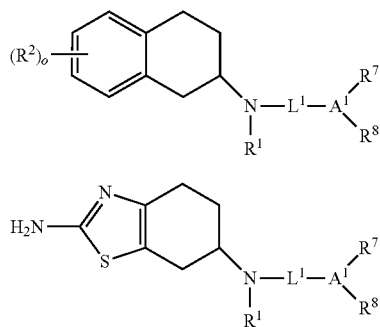

where $R^1$, $R^2$, $R^7$, $R^8$, $L_1$, o, and A are the same as set forth above.

In a refinement of the compounds having formula I, IA, IB, IC, II, IIA, and IIB, A is selected from the group consisting of:

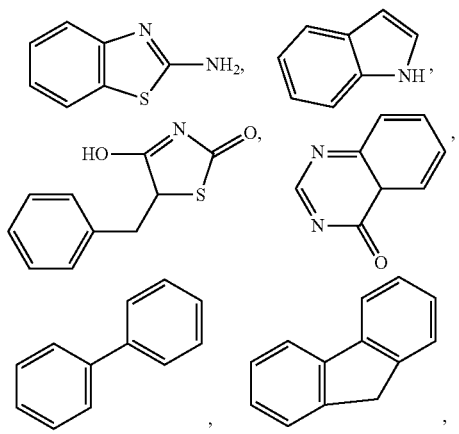

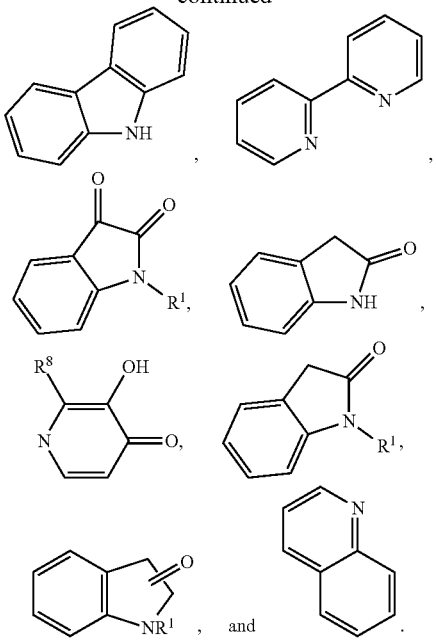

Insert

The compounds set forth herein may be used per se or as pharmaceutically acceptable derivatives. The latter term includes salts, esters, and other derivatives generally considered acceptable by pharmaceutical standards. Useful derivatives, for example, include salts of organic and inorganic acids such as sulfates, phosphates, hydrohalide salts, carboxylate salts, etc., as well as esters of carboxylic acid or hydroxyl substituents, ethers of hydroxyl substituents, amides of amino substituents, as well as carbamates, ureas, etc. Synthesis of these derivatives is conventional, and well known to those skilled in pharmaceutical chemistry. For example, compounds bearing hydroxyl groups may be converted to esters by customary techniques of organic chemistry, such as reaction with an acyl halide, carboxylic acid anhydride, or by esterification with an acid while removing byproduct water. In some cases, derivation may be desired to facilitate compounding of the pharmaceutical into an acceptable form such as tablets, powder, aqueous dispersion, capsule, etc., or may be useful in assisting bioavailability of the drug following administration, for example, by rendering the compound more or less soluble. In many cases, such as, for example, esters, ureas, carbamates, ethers, etc., the derivative may act as "prodrug," which liberates the active form by biological transformation, i.e., by enzymatic hydrolysis of an ester functionality, as is well known to the pharmaceutical chemist.

Typical dosages for mammalian species may vary from 0.001 mg/Kg of body weight to about 100 mg/Kg of body weight, preferably 0.01 mg/Kg to 5 mg/Kg. The actual amount will vary depending upon the particular CNS activity desired to be altered, and the desired degree of alteration. The upper limits may, as with virtually all drugs, be limited by toxicity of the drug or its metabolites, or by the presence of unwanted side effects. The drugs may be administered in any form, but preferably in the form of tablets or capsules with appropriate excipients. Dosages, forms of administration, etc., can be readily determined by those skilled in the art.

Guidelines to the effective dosages in mammalian species are provided by the many known drugs commercially available which bind to CNS monoamine receptor sites, and by comparing the binding affinities of these pharmaceuticals with the target compounds of the subject invention by in vivo and in vitro studies. In addition to the utility of the subject invention compounds in treatment of diseases such as Parkinson's disease, schizophrenia, treatment for addiction such as cocaine addiction, and the like, the subject invention compounds are also useful, particularly in their radio labeled form, for clinical studies directed to distribution of monoamine receptor sites in the brain and the effect which compounds, such as cocaine, have on these sites.

Figure 12:
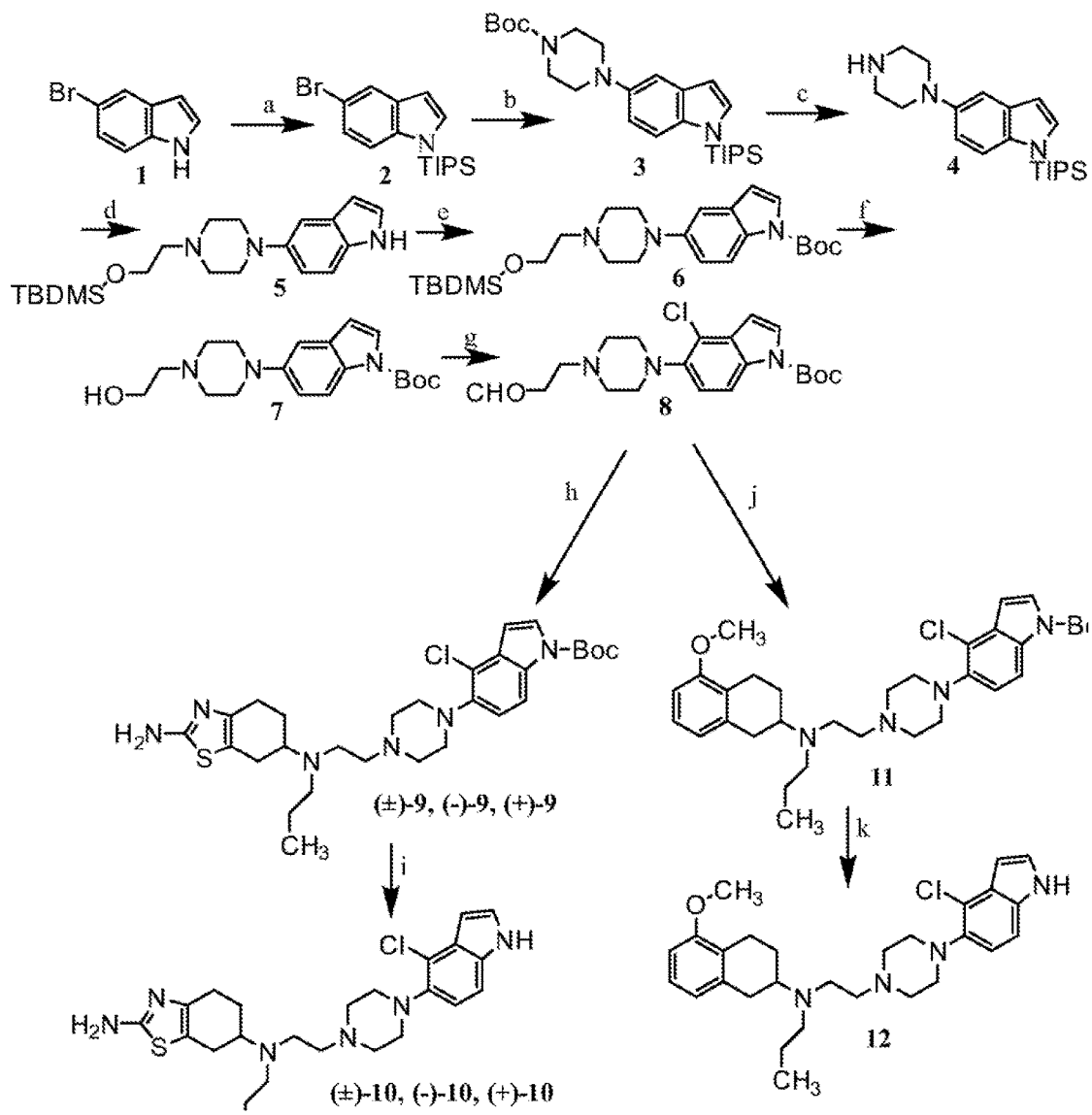
FIG. 12 provides a synthetic scheme for compounds having formula I.

FIG. 12 provides a synthetic scheme for making compounds having formula I. The reaction conditions for this scheme are: (a) trisisopropylsilyl chloride, NaH, THF; (b) 4, $PdCl_2(P(o-tol)_3)_2$, NaOtBu, xylenes, reflux; (c) $CF_3COOH$, $CH_2Cl_2$, (d) (2-bromo-ethoxy)-tert-butyl-dimethyl silane, $K_2CO_3$, $CH_3CN$, reflux; (e) $(Boc)_2O$, DMAP, THF; (f) n-$Bu_4NF$, THF; (g) $(COCl)_2$, DMSO, $Et_3N$, $CH_2Cl_2$, $-78°$ C.-rt; (h)(+/-), (-) or (+)-pramipexole, $Na(OAc)3BH$, $CH_2Cl_2$; (i) $CF_3COOH$, $CH_2Cl_2$; (j) 2, $Na(OAc)3BH$, $CH_2Cl_2$; (k) aq. HBr (48%), reflux.

The following examples illustrate the various embodiments of the present invention. Those skilled in the art will recognize many variations that are within the spirit of the present invention and scope of the claims.

5-Bromo-1-(triisopropylsilyl)-1H-indole (2)

Into a stirring solution of NaH (4.03 g, 170.0 mmol) in dry THF (150 mL), compound 1 (16.44 g, 83.9 mmol) was added portion wise at 0° C. The reaction mixture was allowed to stir at room temperature for 1 h, followed by dropwise addition of triisopropylsilyl chloride (20 g, 103.7 mmol). The reaction mixture was stirred for 12 h and then filtered through celite. The crude residue was purified by column chromatography using hexane as solvent to afford compound 2 (22 g, 75%). $^1$H NMR ($CDCl_3$, 400 MHz): δ 1.23 (s, 18H), 1.74 (heptet, J=7.6 Hz, 3H), 6.64 (d, J=3.2 Hz, 1H), 7.07 (d, J=6 Hz, 1H), 7.14 (s, 1H), 7.31 (d, J=3.2 Hz, 1H), 7.45 (d, J=8.8 Hz, 1H).

tert-Butyl 4-(1-(triisopropylsilyl)-1H-indol-5-yl) piperazine-1-carboxylate (3)

A mixture of compound 2 (22.0 g, 63.0 mmol), tert-butyl piperazine-1-carboxylate (11.71 g, 63.0 mmol), $PdCl_2[P(O-tol)_3]_2$ (2.47 g, 3.1 mmol) and NaOtBu (9.08 g, 94.4 mmol) in xylenes (175 mL) was heated at 110° C. for 12 h. The reaction mixture was filtered through celite and concentrated in vacuo. The crude residue was purified by column chromatography (EtOAc/hexane, 1:20) to afford compound 3 (13.22 g, 46%). $^1$H NMR ($CDCl_3$, 400 MHz): δ 1.19 (s, 18H), 1.55 (s, 9H), 1.74 (heptet, J=6.8 Hz, 3H), 3.14 (bs, 4H), 3.67 (bs, 4H), 6.60 (t, J=6 Hz, 1H), 6.94 (d, J=8.8 Hz, 1H), 7.19 (s, 1H), 7.26 (t, J=2.8 Hz, 1H), 7.47 (d, J=8.8 Hz, 1H).

Procedure C. 5-Piperazin-1-yl-1H-indole (4)

To a stirring solution of compound 3 (7.70 g, 16.8 mmol) in $CH_2Cl_2$ (15 mL), TFA (15 mL) was added slowly at room temperature and the reaction mixture was stirred for 2 h. Unreacted TFA and solvent were removed under reduced pressure and the salt was washed with diethylether. A saturated solution of $NaHCO_3$ was added to the salt, followed by extraction with $CH_2Cl_2$ (3×50 mL). The combined organic layer was dried over $Na_2SO_4$, filtered and evaporated in vacuo to provide compound 4 (2.88 g, 85%). $^1$H NMR ($CDCl_3$, 400 MHz): δ 1.85 (bs, 1H), 2.80-3.28 (m, 8H), 6.85-7.10 (m, 1H), 7.02-7.40 (m, 4H), 8.31 (bs, 1H).

Procedure D. 5-{4-[2-(tert-Butyl-dimethyl-silanyloxy)ethyl]piperazin-1-yl}-1H-indole (5)

A mixture of compound 4 (2.88 g, 14.3 mmol), (2-bromoethoxy)-tert-butyl-dimethylsilane (3.42 g, 14.3 mmol) and $K_2CO_3$ (5.93 g, 42.9 mmol) in $CH_3CN$ (50 mL) was refluxed for 14 hours. After filtration, acetonitrile was evaporated under reduced pressure and the crude material was purified by silica gel column chromatography (EtOAc/hexane, 3:1) to give compound 5 (4.01 g, 78%). $^1$H NMR ($CDCl_3$, 400 MHz): δ 0.02 (s, 6H), 0.83 (s, 9H), 2.30-2.80 (m, 6H), 2.82-3.30 (m, 4H), 3.52-3.82 (m, 2H), 6.25-6.48 (m, 1H), 6.75-7.30 (m, 4H), 8.09 (s, 1H).

5-{4-[2-(tert-Butyl-dimethyl-silanyloxy)ethyl]piperazin-1-yl}indole-1-carboxylic acid tert-butyl ester (6)

Amine 5 (4.0 g, 11.1 mmol) was reacted with $(Boc)_2O$ (2.68 g, 12.2 mmol) and DMAP (1.49 g, 12.2 mmol) in THF (50 mL) at room temperature using procedure G. The crude material was purified by column chromatography over silica gel (EtOAc/hexane, 1:1) to give compound 6 (5.2 g, ~100%). $^1$H NMR ($CDCl_3$, 400 MHz): δ 0.08 (s, 6H), 0.95 (s, 9H), 1.65 (s, 9H), 2.61 (t, J=6.4 Hz, 2H), 2.73 (t, J=4.8 Hz, 4H), 3.19 (t, J=4.8 Hz, 4H), 3.81 (t, J=6.4 Hz, 2H), 6.47 (d, J=3.6 Hz, 1H), 7.01 (dd, J=6.4, 2.4 Hz, 1H), 7.06 (dd, J=6.4, 2.4 Hz, 1H), 7.53 (s, 1H), 8.00 (s, 1H).

Procedure E. 5-[4-(2-Hydroxy-ethyl)piperazin-1-yl] indole-1-carboxylic acid tert-butyl ester (7)

Into a stirring solution of compound 6 (2.0 g, 4.3 mmol) in THF (30 mL), n-tetrabutylammonium fluoride (1.14 g, 4.3 mmol, 1.0 M solution in THF) was added at 0° C. The reaction mixture was then stirred at room temperature for 1 h. THF was evaporated in vacuo, the residue was diluted with $CH_2Cl_2$ (50 mL) and washed with water. The water layer was extracted with $CH_2Cl_2$ (3×75 mL). The combined organic layer was washed with brine, dried over $Na_2SO_4$, and evaporated. The crude product was purified by silica gel column chromatography (EtOAc/MeOH, 20:1) to yield compound 7 (1.49 g, 99%). $^1$H NMR ($CDCl_3$, 400 MHz): δ 1.65 (s, 9H), 2.61 (t, J=5.2 Hz, 2H), 2.70 (t, J=4.8 Hz, 4H), 3.19 (t, J=4.8 Hz, 4H), 3.67 (t, J=5.2 Hz, 2H), 6.47 (d, J=3.6 Hz, 1H), 7.01 (dd, J=6.8, 2 Hz, 1H), 7.06 (d, J=2 Hz, 1H), 7.53 (s, 1H), 8.00 (s, 1H).

tert-butyl 4-chloro-5-(4-(2-oxoethyl)piperazin-1-yl)-1H-indole-1-carboxylate (8)

Compound 7 (1.49 g, 4.3 mmol) was reacted with oxalyl chloride (0.75 mL, 8.6 mmol), DMSO (1.23 mL, 17.3 mmol) and $Et_3N$ (3.6 mL, 25.8 mmol) in $CH_2Cl_2$ (40 mL) using procedure A. The crude residue was purified by column chromatography using ethyl acetate as solvent to afford compound 8 (1.23 g, 83%).

tert-butyl 5-(4-(2-((2-amino-4,5,6,7-tetrahydrobenzo [d]thiazol-6-yl)(propyl)amino)ethyl)piperazin-1-yl)-4-chloro-1H-indole-1-carboxylate [(±)-9]

Compound 8 (175 mg, 0.51 mmol) was reacted with (±)-pramipexole (108 mg, 0.51 mmol) and $NaBH(OAc)_3$ (194 mg, 0.92 mmol) in CH$_2$Cl$_2$ (15 mL) according to procedure B. The crude product was purified by silica gel column chromatography (EtOAc/MeOH, 20:1) to yield compound (±)-9 (150 mg, 55%). $^1$H NMR (CDCl$_3$, 400 MHz): δ 0.91 (t, J=6.8 Hz, 1H), 1.35-1.60 (m, 2H), 1.67 (s, 9H), 1.89-2.10 (m, 1H), 2.30-3.30 (m, 20H), 4.94 (bs, 2H), 6.67 (t, J=3.2 Hz, 1H), 7.09 (dd, J=8.8, 2.8 Hz, 1H), 7.28 (dd, J=3.2 Hz, 1H), 7.59 (s, 1H), 7.97 (d, J=6.4 Hz, 1H).

(S)-tert-butyl 5-(4-(2-((2-amino-4,5,6,7-tetrahydrobenzo[d]thiazol-6-yl)(propyl)amino)ethyl)piperazin-1-yl)-4-chloro-1H-indole-1-carboxylate [(−)-9]

Compound 8 (175 mg, 0.51 mmol) was reacted with S-(−)-pramipexole (108 mg, 0.51 mmol) and NaBH(OAc)$_3$ (194 mg, 0.92 mmol) in CH$_2$Cl$_2$ (15 mL) using procedure B. The crude residue was purified by column chromatography (EtOAc/MeOH, 20:1) to afford compound S-(−)-9 (161 mg, 59%). $^1$H NMR (CDCl$_3$, 400 MHz): δ 0.93 (t, J=6.8 Hz, 1H), 1.35-1.60 (m, 2H), 1.68 (s, 9H), 1.89-2.10 (m, 1H), 2.30-3.30 (m, 20H), 4.94 (bs, 2H), 6.67 (t, J=3.2 Hz, 1H), 7.09 (dd, J=8.8, 2.8 Hz, 1H), 7.28 (dd, J=3.2 Hz, 1H), 7.60 (s, 1H), 7.97 (d, J=6.4 Hz, 1H).

(R)-tert-butyl 5-(4-(2-((2-amino-4,5,6,7-tetrahydrobenzo[d]thiazol-6-yl)(propyl)amino)ethyl)piperazin-1-yl)-4-chloro-1H-indole-1-carboxylate [(+)-9]

Compound 8 (175 mg, 0.51 mmol) was reacted with R-(+)-pramipexole (108 mg, 0.51 mmol) and NaBH(OAc)$_3$ (194 mg, 0.92 mmol) in CH$_2$Cl$_2$ (15 mL) using procedure B. The crude residue was purified by column chromatography using (EtOAc/MeOH, 20:1) to afford compound R-(+)-9 (164 mg, 60%). $^1$H NMR (CDCl$_3$, 400 MHz): δ 0.91 (t, J=6.8 Hz, 1H), 1.37-1.60 (m, 2H), 1.67 (s, 9H), 1.89-2.10 (m, 1H), 2.30-3.30 (m, 20H), 4.94 (bs, 2H), 6.67 (t, J=3.2 Hz, 1H), 7.10 (dd, J=8.8, 2.8 Hz, 1H), 7.28 (dd, J=3.2 Hz, 1H), 7.59 (s, 1H), 7.98 (d, J=6.4 Hz, 1H).

N$^6$-(2-(4-(4-chloro-1H-indol-5-yl)piperazin-1-yl)ethyl)-N$^6$-propyl-4,5,6,7-tetrahydrobenzo[d]thiazole-2,6-diamine [(±)-10]

Compound (±)-9 (150 mg, 0.28 mmol) was reacted with TFA (10 mL) in CH$_2$Cl$_2$ (10 mL) using procedure C. Unreacted TFA and solvent were removed in vacuo and the salt was washed with diethylether and recrystallized from ethanol to afford compound (±)-10 (106 mg, 38%). $^1$H NMR (CD$_3$OD, 400 MHz): δ 0.99 (t, J=7.2 Hz, 3H), 1.52-1.74 (m, 2H), 1.76-2.04 (m, 1H), 2.19 (d, J=9.2 Hz, 1H), 2.52-2.84 (m, 6H), 3.10-3.58 (m, 13H), 6.50 (d, J=3.2 Hz, 1H), 7.05 (d, J=8.8 Hz, 1H), 7.29 (d, J=3.2 Hz, 1H), 7.34 (d, J=8.8 Hz, 2H). $^{13}$C (CD$_3$OD, 100 MHz): δ 12.0, 22.2, 24.0, 25.1, 47.0, 51.1, 54.5, 54.8, 59.2, 101.4, 101.5, 111.8, 115.3, 116.1, 127.8, 129.7, 135.1, 136.0, 140.7, 171.0. M.p. 110-115° C. Anal. calculated for C$_{30}$H$_{40}$F$_9$N$_6$O$_{7.5}$S: C, H, N.

(S)—N$^6$-(2-(4-(4-chloro-1H-indol-5-yl)piperazin-1-yl)ethyl)-N$^6$-propyl-4,5,6,7-tetrahydrobenzo[d]thiazole-2,6-diamine [(−)-10]

Compound (−)-9 (150 mg, 0.28 mmol) was reacted with TFA (10 mL) in CH$_2$Cl$_2$ (10 mL) using procedure C. Unreacted TFA and solvent were removed in vacuo and the salt was washed with diethylether and recrystallized from ethanol to afford compound S-(−)-10 (120 mg, 43%). $^1$H NMR (CD$_3$OD, 400 MHz): δ 0.98 (t, J=7.2 Hz, 3H), 1.54-1.74 (m, 2H), 1.76-2.04 (m, 1H), 2.19 (d, J=9.2 Hz, 1H), 2.52-2.84 (m, 6H), 3.10-3.58 (m, 13H), 6.51 (d, J=3.2 Hz, 1H), 7.05 (d, J=8.8 Hz, 1H), 7.29 (d, J=3.2 Hz, 1H), 7.34 (d, J=8.8 Hz, 2H). $^{13}$C (CD$_3$OD, 100 MHz): δ 12.0, 22.3, 24.0, 25.1, 47.0, 51.1, 54.5, 54.8, 59.2, 101.4, 101.6, 111.8, 115.3, 116.1, 127.8, 129.7, 135.1, 136.0, 140.8, 171.0. [α]$^{25}_D$=−11.0° (c=1.0, CH$_3$OH). M.p. 115-120° C. Anal. calculated for C$_{31}$H$_{37.5}$F$_{10.5}$N$_6$O$_{7}$S: C, H, N.

(R)—N$^6$-(2-(4-(4-chloro-1H-indol-5-yl)piperazin-1-yl)ethyl)-N$^6$-propyl-4,5,6,7-tetrahydrobenzo[d]thiazole-2,6-diamine [(+)-10]

Compound (+)-9 (150 mg, 0.28 mmol) was reacted with TFA (10 mL) in CH$_2$Cl$_2$ (10 mL) using procedure C. Unreacted TFA and solvent were removed in vacuo and the salt was washed with diethylether and recrystallized from ethanol to afford compound R-(+)-10 (140 mg, 50%). $^1$H NMR (CD$_3$OD, 400 MHz): δ 0.98 (t, J=7.2 Hz, 3H), 1.54-1.78 (m, 2H), 1.76-2.04 (m, 1H), 2.20 (d, J=9.2 Hz, 1H), 2.52-2.84 (m, 6H), 3.10-3.58 (m, 13H), 6.51 (d, J=3.2 Hz, 1H), 7.05 (d, J=8.8 Hz, 1H), 7.29 (d, J=3.2 Hz, 1H), 7.34 (d, J=8.8 Hz, 2H). $^{13}$C (CD$_3$OD, 100 MHz): δ 12.2, 22.3, 24.0, 25.1, 47.0, 51.2, 54.5, 54.8, 59.2, 101.4, 101.6, 111.8, 115.3, 116.1, 127.8, 129.7, 135.1, 136.2, 140.8, 171.0. [α]$^{25}_D$=−15.5° (c=1.0, CH$_3$OH). M.p. 115-120° C. Anal. calculated for C$_{31}$H$_{37.9}$F$_{10.5}$N$_6$O$_{7.2}$S: C, H, N.

tert-butyl 4-chloro-5-(4-(2-((5-methoxy-1,2,3,4-tetrahydronaphthalen-2-yl)(propyl)amino)ethyl)piperazin-1-yl)-1H-indole-1-carboxylate (11)

Aldehyde 8 (320 mg, 0.93 mmol) was reacted with 5-methoxy-N-propyl-1,2,3,4-tetrahydronaphthalen-2-amine (204 mg, 0.93 mmol) and NaBH(OAc)$_3$ (355 mg, 1.68 mmol) in CH$_2$Cl$_2$ (20 mL) using procedure B. The crude material was purified by column chromatography over silica gel (EtOAc/hexane, 1:1) to give compound 11 (190 mg, 38%). $^1$H NMR (CDCl$_3$, 400 MHz): δ 0.91 (t, J=7.2 Hz, 3H), 1.33-1.75 (m, 13H), 1.95-2.13 (m, 1H), 2.35-3.23 (m, 18H), 3.81 (s, 3H), 6.55-6.77 (m, 3H), 7.03-7.15 (m, 3H), 7.58 (d, J=2.4 Hz, 1H), 7.96 (d, J=6.8 Hz, 1H).

6-((2-(4-(4-chloro-1H-indol-5-yl)piperazin-1-yl)ethyl)(propyl)amino)-5,6,7,8-tetrahydronaphthalen-1-ol (12)

A mixture of compound 11 (60 mg, 0.11 mmol) and 48% aq. HBr (10 ml) was refluxed for 5 h. The reaction mixture was evaporated to dryness and the residue was washed with diethylether. Finally, the HBr salt was recrystallized from ethanol to furnish compound 12 (50 mg, 60%). $^1$H NMR (CD$_3$OD, 400 MHz): δ 0.95 (t, J=7.2 Hz, 3H), 1.41-1.57 (m, 3H), 2.00-2.22 (m, 1H), 2.58-3.18 (m, 19H), 6.61 (d, J=8 Hz, 1H), 6.75 (d, J=8 Hz, 1H), 7.08 (t, J=7.6 Hz, 1H), 7.19-7.38 (m, 3H), 7.51 (d, J=8 Hz, 1H), 7.90 (d, J=8.2 Hz, 1H), 8.50 (bs, 1H). M.p. 250-260° C. Anal. calculated for C$_{27}$H$_{41.4}$Br$_4$N$_4$O$_{1.7}$: C, H, N.

TABLE 1

Inhibition constants for competition with [$^3$H]spiroperidol binding to cloned rat D2L and D3 receptors expressed in HEK-293 cells.

| Compound | K$_i$ (nM), rD2L [$^3$H]spiroperidol | K$_i$ (nM), rD3 [$^3$H]spiroperidol | D2L/D3 |
|---|---|---|---|
| (±)-10 | 46.7 ± 6.6 | 1.92 ± 0.38 | 24.3 |
| (−)-10 | 39 ± 5 | 2.19 ± 0.39 | 17.8 |

TABLE 1-continued

Inhibition constants for competition with [$^3$H]spiroperidol binding to cloned rat D2L and D3 receptors expressed in HEK-293 cells.

| Compound | $K_i$ (nM), rD2L [$^3$H]spiroperidol | $K_i$ (nM), rD3 [$^3$H]spiroperidol | D2L/D3 |
|---|---|---|---|
| (+)-10 | 134 ± 12 | 15.9 ± 3.6 | 8.46 |
| 12 | 76.4 ± 2.4 | 10.4 ± 1.6 | 7.3 |

Figure 13:
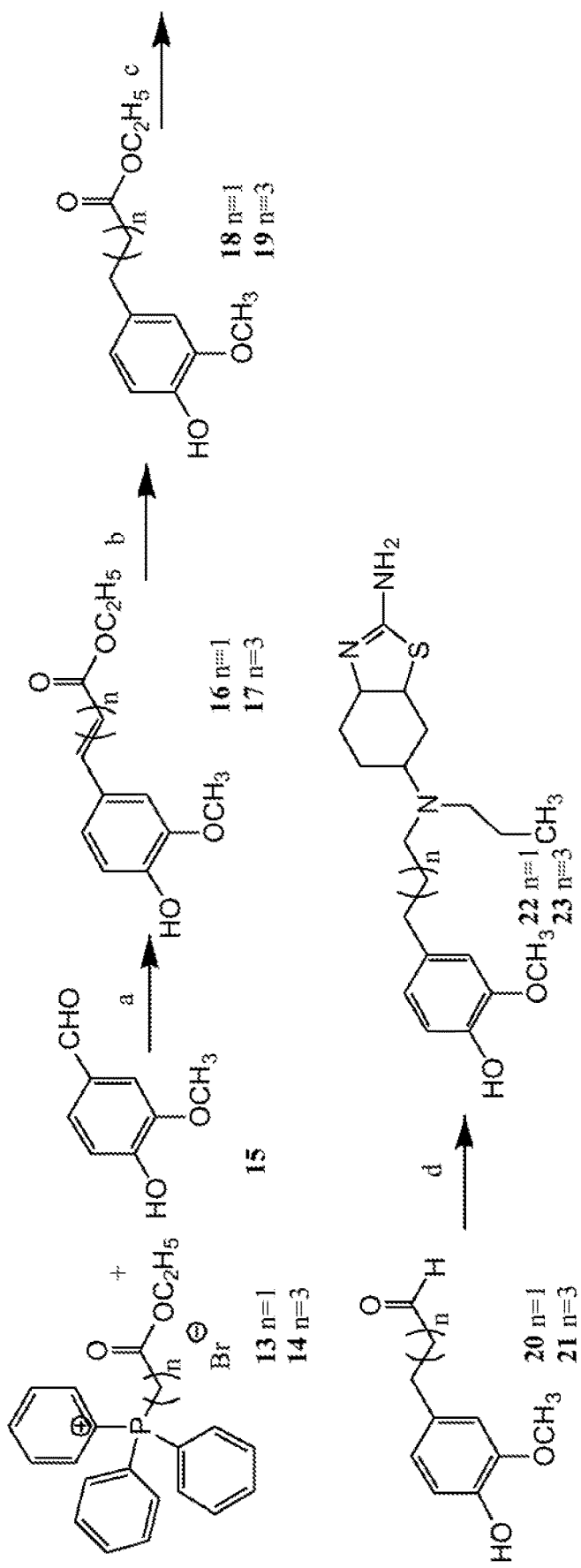
FIG. 13 provides a synthetic scheme for compounds having formula II.

FIG. 13 provides a synthetic scheme for the compounds having formula II. The reaction conditions for this scheme are: (a) NaHMDS, THF, −78° C. to rt, 48 h; (b) 10% pd/C, H$_2$, ethanol, rt, 2 h; (c) DIBALH, toluene, −78° C., 2 h; (d) Pramipexole, NaBH(OAc)$_3$, DCE, rt, 24 h.

Procedure A

Ethyl 3-(4-hydroxy-3-methoxyphenyl)acrylate (16) and Ethyl 5-(4-hydroxy-3-methoxyphenyl)pent-4-enoate (17)

Commercially available (ethoxycarbonylmethyl)triphenylphosphonium bromide 13 (3.10 g, 7.23 mmol) was added to dry THF (8 mL) in an oven-dried round bottom flask. The resulting suspension was cooled to −78° C. Then a solution of NaHMDS (1M in THF, 7.88 mL, 7.88 mmol) was added drop-wise and the reaction mixture stirred at −78° C. for 1 h. Thereafter, a solution of Vanillin 15 (1.0 g, 6.57 mmol) in dry THF (2 mL) was added drop-wise and reaction stirred at −78° C. for 2 h, then warmed to room temperature and stirred for 48 h. The reaction mixture was then extracted with ethyl acetate (2×75 mL) and washed with brine. The combined organic layer was dried over sodium sulfate and concentrated in vacuo. The crude thus obtained was purified by column chromatography (Hexane/ethyl acetate 9:1) to yield compound 16 (1.25 g, 85%) as colorless oil with a preferential Z:E ratio of >20:1: $^1$H NMR (400 MHz, CDCl$_3$) δ ppm 1.33 (t, 3H, J=7.6 Hz, CH$_3$), 3.92 (s, 3H, OCH$_3$), 4.25 (q, 2H, J=7.2 Hz, OCH$_2$), 5.83 (m, 1H, CH), 6.29 (d, 1H, J=15.2 Hz, CH), 6.91 (d, 1H, J=8.0 Hz, ArH), 7.03 (m, 2H, ArH)

Preparation of Starting Material [3-(Ethoxycarbonyl)propyl]triphenylphosphonium bromide (14)

Triphenylphosphine (3.76 g, 14.35 mmol) and ethyl 4-bromobutyrate (2 g, 10.25 mmol) were added to a dried round bottom flask under argon. The reaction mixture was heated to 120° C. under condenser for 16 h after which the reaction was allowed to come to room temperature. DCM (10 mL) was added, followed by diethyl ether until no further precipitation of product was observed. The precipitate was further washed with ether (100 mL) and solvent dried in vacuo to give pure compound 14 as a white solid (4.64 g) in quantitative yields. $^1$H NMR (400 MHz, CDCl$_3$) δ ppm 1.22 (t, 3H, J=7.2 Hz, CH$_3$), 1.88-1.94 (m, 2H, CH$_2$), 2.86-2.89 (m, 2H, CH$_2$), 3.98-4.12 (m, 4H, CH$_2$), 7.67-7.90 (15H, ArH).

Starting material 14 (3.30 g, 7.23 mmol) was reacted with vanillin 15 (1.0 g, 6.57 mmol) according to procedure A and the crude product was purified using column chromatography (Hexane/ethyl acetate 9:1) to yield compound 17 (1.17 g, 71%) as colorless oil with a preferential Z:E ratio of >20:1: $^1$H NMR (400 MHz, CDCl$_3$) δ ppm 1.24 (t, 3H, J=7.2 Hz, CH$_3$), 2.45 (t, 2H, J=8.0 Hz, CH$_2$), 2.63-2.69 (m, 2H, CH$_2$), 3.88 (s, 3H, OCH$_3$), 4.13 (q, 2H, J=7.2 Hz, OCH$_2$), 5.49-5.55 (m, 1H, CH), 5.64 (s, 1H, OH), 6.37 (d, 1H, J=11.2 Hz, CH), 6.79-6.82 (m, 2H, ArH), 6.88 (d, 1H, J=8.2 Hz, ArH)

Procedure B

Ethyl 3-(4-hydroxy-3-methoxyphenyl)propanoate (18) and Ethyl 5-(4-hydroxy-3-methoxyphenyl)pentanoate (19)

Intermediate 16 (1.0 g, 4.45 mmol) was dissolved in ethanol (10 mL) in a round bottom flask and 10% Pd/C (0.10 g, 10 wt %) was added to it. The reaction flask was degassed and then stirred under hydrogen atmosphere for 2 h at room temperature. After the completion of reaction, the mixture was diluted with ethanol (20 mL) and passed through a short bed of celite. The organic layer was concentrated to afford compound 18 (0.95 gm) as colorless oil in quantitative yield which was pure enough for the next step. $^1$H NMR (400 MHz, CDCl$_3$) δ ppm 1.23 (t, 3H, J=7.2 Hz, CH$_3$), 2.58 (t, 2H, J=8.0 Hz, CH$_2$), 2.87 (t, 2H, J=7.6 Hz, CH$_2$), 3.84 (s, 3H, OCH$_3$), 4.12 (q, 2H, J=7.2 Hz, OCH$_2$), 6.68 (m, 2H, ArH), 6.82 (d, 1H, J=7.2 Hz, ArH).

Intermediate 17 (1.0 g, 3.96 mmol) was stirred under hydrogen atmosphere following procedure B to yield compound 19 (0.98 g) in quantitative yield which was taken to the next step without further purification. $^1$H NMR (400 MHz, CDCl$_3$) δ ppm 1.24 (t, 3H, J=7.2 Hz, CH$_3$), 1.58-1.70 (m, 4H, CH$_2$), 2.31 (t, 2H, J=7.2 Hz, CH$_2$), 2.55 (t, 2H, J=7.2 Hz, CH$_2$), 3.87 (s, 3H, OCH$_3$), 4.12 (q, 2H, J=7.2 Hz, OCH$_2$), 6.65-6.67 (m, 2H, ArH), 6.82 (d, 1H, J=8.0 Hz, ArH)

Procedure C

3-(4-Hydroxy-3-methoxyphenyl)propanal (20) and 5-(4-Hydroxy-3-methoxyphenyl)pentanal (21)

To a solution of compound 18 (0.60 g, 2.67 mmol) in dry toluene (10 mL) under argon was added DIBALH solution (1M in hexane, 2.93 mL, 2.93 mmol) at −78° C. The reaction mixture was stirred at −78° C. for 2 h. Methanol (0.20 mL) was added to the reaction mixture and reaction allowed to come to 0° C. The reaction mixture was then added to a separating funnel containing HCl (1N, 10 ml) and extracted with ethyl acetate (3×30 mL). The combined organic layer was washed with brine, dried over sodium sulfate, and evaporated under reduced pressure. The crude was purified by column chromatography (Hexane/ethyl acetate 7:1) to give compound 20 (0.22 gm, 45.6%) as yellow oil. $^1$H NMR (400 MHz, CDCl$_3$) δ ppm 2.75 (t, 2H, J=8.0 Hz, CH$_2$), 2.89 (t, 2H, J=7.6 Hz, CH$_2$), 3.87 (s, 3H, OCH$_3$), 6.68 (m, 2H, ArH), 6.83 (d, 1H, J=7.2 Hz, ArH), 9.81 (t, 1H, J=1.6 Hz, CHO)

Intermediate 19 (0.50 g, 1.96 mmol) was reduced with DIBALH solution (1M in hexane, 2.16 mL, 2.16 mmol) in dry toluene using procedure C. The crude was purified by column chromatography (Hexane/ethyl acetate 8:1) to yield compound 21 (0.196 g, 48%) as colorless oil. $^1$H NMR (400 MHz, CDCl$_3$) δ ppm 1.59-1.68 (m, 4H, CH$_2$), 2.44 (td, 2H, J$_1$=6.40 Hz, J$_2$=1.60 Hz CH$_2$), 2.56 (t, 2H, J=7.2 Hz, CH$_2$), 3.87 (s, 3H, OCH$_3$), 6.65 (m, 2H, ArH), 6.82 (d, 1H, J=8.0 Hz, ArH), 9.75 (t, 1H, J=1.6 Hz, CHO).

Procedure D

4-(3-((2-Amino-4,5,6,7-tetrahydrobenzo[d]thiazol-6-yl)(propyl)amino)propyl)-2-methoxyphenol (22) and 4-(5-((2-Amino-4,5,6,7-tetrahydrobenzo[d]thiazol-6-yl)(propyl)amino)pentyl)-2-methoxyphenol (23)

Into a stirring solution of (±) Pramipexole (0.123 g, 0.58 mmol) in DCE (15 mL) was added aldehyde 20 (0.10 g, 0.55 mmol) and the mixture stirred for 1 h. NaBH(OAC)$_3$ (0.235 g 1.10 mmol) was then added portion-wise and the reaction stirred for 24 h at room temperature. The reaction mixture was quenched with a saturated NaHCO$_3$ solution at 0° C. and extracted with ethyl acetate (3×25 mL). The combined organic layer was dried over sodium sulfate and solvent was removed under reduced pressure. The crude product was purified by column chromatography (ethyl acetate/methanol 20:1) to give compound 22 (0.079 g, 38%). $^1$H NMR (400 MHz, CD$_3$OD) δ ppm 0.95 (t, 3H, J=7.2 Hz, CH$_3$), 1.59 (m, 2H, CH$_2$), 1.81-1.92 (m, 3H, CH$_2$), 2.05-2.12 (m, 1H, CH$_2$), 2.57-2.67 (m, 6H, CH$_2$), 2.73-2.89 (m, 5H, CH$_2$, CH), 3.82 (s, 3H, OCH$_3$), 6.64 (d, 1H, J=8.0 Hz, ArH), 6.71 (d, 1H, J=8.0 Hz, ArH), 6.79 (s, 1H, ArH). The free base was converted into its corresponding hydrochloride salt. Mp 220-222° C. Anal. (C$_{20}$H$_{32}$Cl$_2$N$_3$O$_{2.5}$S) C, H, N.

Aldehyde 21 (0.10 g, 0.48 mmol) and (±) Pramipexole (0.106 g, 0.50 mmol) in DCE (15 mL) were reacted using procedure D and the resulting crude was purified by column chromatography (ethyl acetate/methanol 21:1) to give compound 23 (0.068 g, 35%). $^1$H NMR (400 MHz, DMSO-d$_6$) δ ppm 0.89 (t, 3H, J=7.2 Hz, CH$_3$), 1.28-1.36 (m, 3H, CH$_2$), 1.48-1.53 (m, 4H, CH$_2$), 1.59-1.70 (m, 3H, CH$_2$), 2.57-2.67 (m, 1H, CH$_2$), 2.503-2.65 (m, 9H, CH$_2$), 3.05 (bs, 1H, CH$_2$), 3.82 (s, 3H, OCH$_3$), 6.58 (d, 1H, J=8.4 Hz, ArH), 6.64-6.72 (m, 2H, ArH). The free base was converted into its corresponding hydrochloride salt. Mp 224-226° C. Anal. (C$_{23.6}$H$_{37.8}$N$_3$O$_{2.8}$S$_{1.22}$) C, H, N.

Elemental Analysis Report of Compounds 22 and 23

| Compound | Calculated | | | Found | | |
|---|---|---|---|---|---|---|
| | C | H | N | C | H | N |
| 22•2HCl•0.5H$_2$O | 52.51 | 7.05 | 9.19 | 52.12 | 7.19 | 8.83 |
| 23•2HCl•0.58C$_2$H$_5$OH•0.22CH$_3$SOCH$_3$ | 54.47 | 7.71 | 8.07 | 54.86 | 7.31 | 7.60 |

Figure 14:
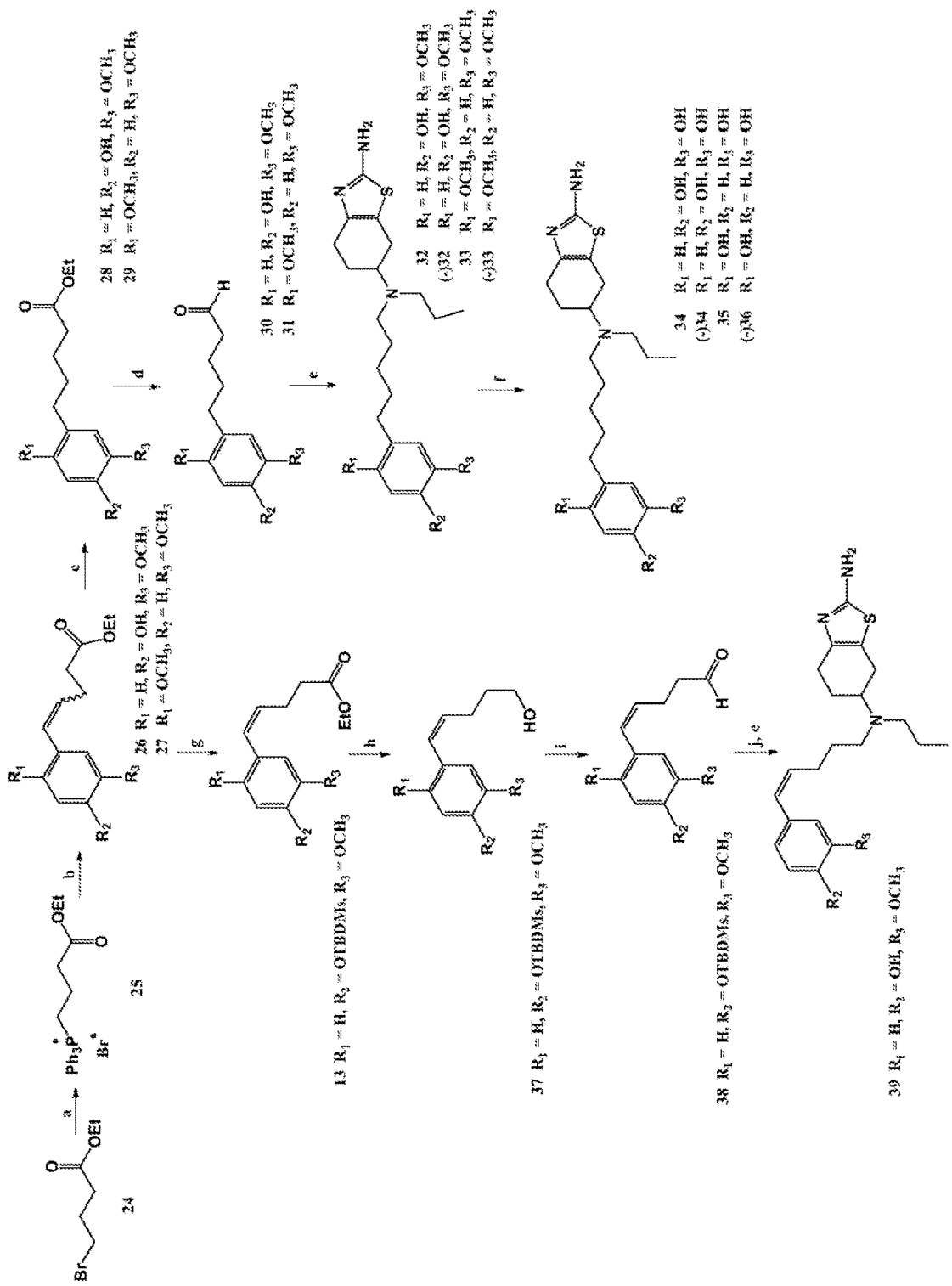
FIG. 14 provides a synthetic scheme for compounds having formula II.

FIG. 14 provides a synthetic scheme for the compounds having formula II, specifically compounds 34, 35, and 35. The reaction conditions for this scheme are (a) TPP, toluene, reflux, 16 h, qunat. yield; (b) Aldehyde, NaHMDS, THF, −78° C. to rt, 48 h; 35-43%; (c) 10% pd/C, H$_2$, ethanol, rt, 2 h, 96%; (d) DIBALH, toluene, −78° C., 2 h, 48-80%; (e) Pramipexole, NaBH(OAc)$_3$, DCM, rt, 36 h, 53-69%; (f) BBr$_3$, DCM, −78° C. to rt, 6 h, 62-80%; (g) TBDMSCl, imidazole, DMF, rt, 2 h, qunat. yield; (h) DIBALH, THF, −10° C. to rt, 6 h, 87%; (i) PCC, DCM, ° C. to rt, 9 h, 45%; (j) TBAF, THF, 0° C., 1.5 h.

[3-(Ethoxycarbonyl)propyl]triphenylphosphonium bromide (25)

Procedure A'. (4-ethoxy-4-oxobutyl)triphenylphosphonium bromide

Triphenylphosphine (3.76 g, 14.35 mmol) and ethyl 4-bromobutyrate (2 g, 10.25 mmol) was added to a dried round bottom flask under argon. The reaction mixture was heated to 120° C. under condenser for 16 h after which the reaction was allowed to come to room temperature. DCM (10 mL) was added, followed by diethyl ether until no further precipitation of product was observed. The precipitate was further washed with ether (100 mL) and solvent dried in vacuo to give pure compound 25 as a white solid (4.64 g) in quantitative yields. $^1$H NMR (400 MHz, CDCl$_3$) δ ppm 7.67-7.90 (m, 15H), 3.98-4.12 (m, 4H), 2.86-2.89 (m, 2H), 1.88-1.94 (m, 2H), 1.22 (t, J=7.2 Hz, 3H).

Procedure B'. Ethyl 5-(4-hydroxy-3-methoxyphenyl)pent-4-enoate (26)

Starting material 2 (6.61 g, 14.46 mmol) was added to dry THF (15 mL) in an oven-dried round bottom flask. The resulting suspension was cooled to −78° C. Then a solution of NaHMDS (1M in THF, 15.77 mL, 15.77 mmol) was added drop-wise and the reaction mixture stirred at −78° C. for 1 h. Thereafter, a solution of Vanillin (2.0 g, 13.14 mmol) in dry THF (5 mL) was added drop-wise and reaction stirred at −78° C. for 2 h, then warmed to room temperature and stirred for 48 h. The reaction mixture was then extracted with ethyl acetate (2×100 mL) and washed with brine. The combined organic layer was dried over sodium sulfate and concentrated in vacuo. The crude thus obtained was purified by column chromatography using 10% ethyl acetate in hexane to yield compound 26 (1.17 g, 35.6%) as colorless oil with a preferential Z:E ratio of >20:1: $^1$H NMR (400 MHz, CDCl$_3$) δ ppm 6.88 (d, J=8.2 Hz, 1H), 6.79-6.82 (m, 2H), 6.37 (d, J=11.2 Hz, 1H), 5.64 (s, 1H), 5.49-5.55 (m, 1H), 4.13 (q, J=7.2 Hz, 2H), 3.88 (s, 3H), 2.63-2.69 (m, 2H), 2.45 (t, J=8.0 Hz, 2H), 1.24 (t, J=7.2 Hz, 3H).

Ethyl 5-(2,5-dimethoxyphenyl)pentanoate (27)

Starting material 25 (7.56 g, 16.57 mmol) was reacted with 2,5-dimethoxy benzaldehyde (2.5 g, 15.07 mmol) in presence of NaHMDS 1M in THF (18.05 mmol, 18.05 mL) according to Procedure A'. the crude was purified by column chromatography using 7-10% ethyl acetate in hexanes to give compound 27 (1.71 g, 43%). $^1$H NMR (400 MHz, CDCl$_3$) δ ppm 6.82 (d, J=2.4 Hz, 1H), 6.74-6.79 (m, 2H), 6.52 (d, J=11.2 Hz, 1H), 5.65-5.72 (m, 1H), 4.12 (q, J=7.2 Hz, 2H), 3.78 (s, 3H), 3.77 (s, 3H), 2.55-2.60 (m, 2H), 2.41 (t, J=7.2 Hz, 2H), 1.23 (t, J=7.2 Hz, 3H).

Procedure C'. Ethyl 5-(4-hydroxy-3-methoxyphenyl)pentanoate (5)

Intermediate 26 (1.0 g, 3.96 mmol) dissolved in ethanol (10 mL) in a round bottom flask and 10% Pd/C (0.10 g, 10 wt %) was added to it. The reaction flask was degassed and then stirred under hydrogen atmosphere for 2 h at room temperature. After the completion of reaction, the mixture was diluted with ethanol (20 mL) and passed through a short bed of celite. The organic layer was concentrated to afford compound 5 (0.98 gm) in quantitative yield which was pure enough for the next step. $^1$H NMR (400 MHz, CDCl$_3$) δ ppm 6.82 (d, J=8.0 Hz, 1H), 6.65-6.67 (m, 2H), 4.12 (q, J=7.2 Hz, 2H), 2.55 (t, J=7.2 Hz, 2H), 3.87 (s, 3H), 2.31 (t, J=7.2 Hz, 2H), 1.58-1.70 (m, 4H), 1.24 (t, J=7.2 Hz, 3H).

Ethyl 5-(2,5-dimethoxyphenyl)pentanoate (29)

Intermediate 27 (1.0 g, mmol) dissolved in ethanol (10 mL) and reacted with 10% Pd/C (0.1 g, 10 wt %) according to Procedure C' to afford compound 6 (0.96 g, 96%) which was used without further purification. $^1$H NMR (400 MHz, CDCl$_3$) δ ppm 6.75 (d, J=8.8 Hz, 1H), 8.72 (d, J=3.2 Hz, 1H), 6.68 (dd, J=8.4, 2.4 Hz, 1H), 4.12 (q, J=7.2 Hz, 2H), 3.76 (s, 3H), 3.75 (s, 3H), 2.60 (t, J=7.4 Hz, 2H), 2.33 (t, J=7.2 Hz, 2H), 1.56-1.70 (m, 4H), 1.24 (t, J=7.2 Hz, 3H).

Procedure D'.
5-(4-Hydroxy-3-methoxyphenyl)pentanal (30)

To a solution of compound 5 (0.50 g, 1.96 mmol) in dry toluene (10 mL) under argon was added DIBALH solution (1M in hexane, 2.16 mL, 2.16 mmol) at −78° C. The reaction mixture was stirred at −78 C for 2 h. Methanol (0.20 mL) was added to the reaction mixture and reaction allowed to come to 0° C. The reaction mixture was then added to a separating funnel containing HCl (1N, 10 ml) and extracted with ethyl acetate (3×30 mL). The combined organic layer was washed with brine, dried over sodium sulfate, and evaporated under reduced pressure. The crude was purified by column chromatography using 11-15% ethyl acetate in hexanes to yield compound 30 (0.196 g, 48%) as colorless oil. $^1$H NMR (400 MHz, CDCl$_3$) δ ppm 9.75 (t, J=1.6 Hz, 1H), 6.82 (d, J=8.0 Hz, 1H), 6.65 (m, 2H), 3.87 (s, 3H), 2.56 (t, J=7.2 Hz, 2H), 2.44 (td, J$_1$=6.40 Hz, J$_2$=1.60 Hz 2H), 1.59-1.68 (m, 4H).

5-(2,5-dimethoxyphenyl)pentanal (31)

Intermediate 29 (0.6 g, 2.25 mmol) was reduced with DIBALH solution (1M in hexane, 2.47 mL, 2.47 mmol) in dry toluene (10 mL) using procedure D'. The crude was purified by column chromatography using 11-15% ethyl acetate in hexanes to give compound 8 (0.4 gm, 80%) as yellow oil. $^1$H NMR (400 MHz, CDCl$_3$) δ ppm 9.74 (d, J=1.6 Hz, 1H), 6.76 (d, J=8.8 Hz, 1H), 6.67-6.71 (m, 2H), 3.76 (s, 3H), 3.75 (s, 3H), 2.60 (t, J=6.4 Hz, 2H), 2.44 (t, J=6.8 Hz, 2H), 1.58-1.37 (m, 4H).

Procedure E'. 4-(5-((2-Amino-4,5,6,7-tetrahydrobenzo[d]thiazol-6-yl)(propyl)amino)pentyl)-2-methoxyphenol (32)

Into a stirring solution of (±) Pramipexole (015 g, 0.71 mmol) in DCM (8 mL) was added aldehyde 30 (0.148 g, 0.71 mmol) and the mixture stirred for 1 h. NaBH(OAc)$_3$ (0.27 g, 1.27 mmol) was then added portion-wise followed by MeOH (0.8 mL). The reaction was stirred for 36 h at room temperature. The reaction mixture was quenched with a saturated NaHCO$_3$ solution at 0° C. and extracted with DCM (3×25 mL). The combined organic layer was dried over sodium sulfate and solvent was removed under reduced pressure. The crude product was purified by column chromatography using 5-7% MeOH in DCM to give compound 32 (0.2 g, 69%). $^1$H NMR (400 MHz, DMSO-d$_6$) δ ppm 6.64-6.72 (m, 2H), 6.58 (d, J=8.4 Hz, 1H), 3.82 (s, 3H), 3.05 (bs, 1H), 2.50-2.67 (m, 10H), 1.59-1.70 (m, 3H), 1.48-1.53 (m, 4H), 1.28-1.36 (m, 3H), 0.89 (t, J=7.2 Hz, 3H). The free base was converted into its corresponding hydrochloride salt. Mp 224-226° C. Anal. (C$_{23.6}$H$_{37.8}$N$_3$O$_{2.8}$S$_{1.22}$) C, H, N.

(R)-4-(5-((2-Amino-4,5,6,7-tetrahydrobenzo[d]thiazol-6-yl)(propyl)amino)pentyl)-2-methoxyphenol (−32)

Aldehyde 30 (0.148 g, 0.71 mmol), (−) Pramipexole (0.15 g, 0.71 mmol), and NaBH(OAc)$_3$ (0.27 g, 1.27 mmol) in DCM (8 mL) and MeOH (0.8 mL) were reacted using procedure D' and the resulting crude was purified by column chromatography using 5-7% MeOH in DCM to give compound (−32) (0.19 g, 66%). $^1$H NMR (400 MHz, DMSO-d$_6$) δ ppm 6.64-6.72 (m, 2H), 6.58 (d, J=8.4 Hz, 1H), 3.82 (s, 3H), 3.05 (bs, 1H), 2.65-2.67 (m, 1H), 2.50-2.65 (m, 9H), 1.59-1.70 (m, 3H), 1.48-1.53 (m, 4H), 1.28-1.36 (m, 3H), 0.90 (t, J=7.2 Hz, 3H). The free base was converted into its corresponding hydrochloride salt. Mp 196-198° C. Anal. (C$_{22}$H$_{37}$N$_3$Cl$_2$O$_3$S) C, H, N.

N$^6$-(5-(2,5-dimethoxyphenyl)pentyl)-N$^6$-propyl-4,5,6,7-tetrahydrobenzo[d]thiazole-2,6-diamine (33)

Aldehyde 31 (0.157 g, 0.706 mmol), (±) Pramipexole (0.15 g, 0.709 mmol), and NaBH(OAc)$_3$ (0.27 g, 1.27 mmol) in DCM (9 mL) and MeOH (0.8 mL) were reacted using procedure D' and the resulting crude was purified by column chromatography using 5-7% MeOH in DCM to give compound (0.17 g, 57%). $^1$H NMR (400 MHz, CDCl$_3$) δ ppm 6.75 (d, J=8.8 Hz, 1H), 6.70 (d, J=2.4 Hz, 1H), 6.66 (dd, J=8.8, 2.1 Hz, 1H), 3.75 (s, 3H), 3.74 (s, 3H), 3.07 (bs, 1H), 2.69 (dd, J=12.0, 4.04 Hz, 2H), 2.47-2.58 (m, 8H), 1.99-2.03 (m, 1H), 1.68-1.78 (m, 1H), 1.40-1.61 (m, 6H), 1.31-1.37 (m, 2H), 0.89 (t, J=7.2 Hz, 3H).

(R)—N$^6$-(5-(2,5-dimethoxyphenyl)pentyl)-N$^6$-propyl-4,5,6,7-tetrahydrobenzo[d]thiazole-2,6-diamine (−33)

Aldehyde 31 (0.105 g, 0.473 mmol), (−) Pramipexole (0.10 g, 0.473 mmol), and NaBH(OAc)$_3$ (0.27 g, 0.849 mmol) in DCM (7 mL) and MeOH (0.6 mL) were reacted using procedure D' and the resulting crude was purified by column chromatography using 5-7% MeOH in DCM to give compound (0.105 g, 53%). $^1$H NMR (600 MHz, CDCl$_3$) δ ppm 6.76 (d, J=8.4 Hz, 1H), 6.71 (d, J=1.8 Hz, 1H), 6.67 (dd, J=8.4, 3.0 Hz, 1H), 4.71 (bs, 2H), 3.77 (s, 3H), 3.76 (s, 3H), 3.04 (bs, 1H), 2.69 (d, J=7.2 Hz, 2H), 2.4-2.6 (m, 8H), 2.0 (bs, 1H), 1.62-1.72 (m, 2H), 1.55-1.61 (m, 2H), 1.41-1.52 (m, 3H), 1.33-1.37 (m, 2H), 0.88 (t, J=7.2 Hz, 3H).

Procedure F'. 4-(5-((2-Amino-4,5,6,7-tetrahydrobenzo[d]thiazol-6-yl)(propyl)amino)pentyl)benzene-1,2-diol (34)

BBr$_3$ 1M in DCM (2.66 mL, 2.66 mmol) was added to a solution of compound 32 (0.2 g, 0.532 mmol) in DCM (20 mL) at −78° C. and stirred for 2 h. The reaction mixture was allowed to come to room temperature and stirred for another 4 h. The reaction was then quenched by methanol (20 mL) at 0° C. and the solvent was concentrated in vacuo, and MeOH (20 mL) was added to the residue and again evaporated. This process was repeated three times. The residue obtained was purified by column chromatography using 10-15% methanol in DCM to give pure compound 34 (123 mg, 64%). $^1$H NMR (400 MHz, CD$_3$OD) δ ppm 6.64 (d, J=8.0 Hz, 1H), 6.60 (d, J=2.4 Hz, 1H), 6.47 (dd, J=8.0, 2.4 Hz, 1H), 3.35-3.40 (m, 1H), 2.75-2.85 (m, 5H), 2.62-2.71 (m, 2H), 2.55-2.57 (m, 1H), 2.47 (t, J=7.2 Hz, 2H), 2.09-2.14 (m, 1H), 1.79-1.89 (m, 1H), 1.57-1.64 (m, 6H), 1.31-1.38 (m, 2H), 0.95 (t, J=7.6 Hz, 3H). The free base was converted into its corresponding hydrochloride salt. Mp 196-198° C. Anal. ($C_{21}H_{34}N_3Cl_3O_2S$) C, H, N.

(R)-4-(5-((2-Amino-4,5,6,7-tetrahydrobenzo[d]thiazol-6-yl)(propyl)amino)pentyl)benzene-1,2-diol (−34)

BBr$_3$ 1M in DCM (1.61 mL, 1.61 mmol) was reacted with compound −32 (0.132 g, 0.327 mmol) in DCM (10 mL) according to Procedure F' to afford crude which was purified by column chromatography using 10-15% MeOH in DCM to give compound −11 (0.09 g, 70%). $^1$H NMR (600 MHz, CD$_3$OD) δ ppm 6.63 (d, J=7.8 Hz, 1H), 6.58 (d, J=1.8 Hz, 1H), 6.45 (dd, J=7.8, 1.8 Hz, 1H), 2.97-3.02 (m, 1H), 2.42-2.62 (m, 10H), 1.95-1.97 (m, 1H), 1.60-1.73 (m, 1H), 1.53-1.58 (quintet, J=7.8 Hz, 2H), 1.42-1.48 (septet, J=7.2 Hz, 4H), 1.26-1.31 (quintet, J=7.2 Hz, 2H), 0.88 (t, J=7.2 Hz, 3H). The free base was converted into its corresponding hydrochloride salt. Mp 211-212° C. Anal. ($C_{21}H_{35}N_3Cl_2O_2S$) C, H, N.

2-(5-((2-Amino-4,5,6,7-tetrahydrobenzo[d]thiazol-6-yl)(propyl)amino)pentyl)benzene-1,4-diol (35)

BBr$_3$ 1M in DCM (2.27 mL, 2.27 mmol) was reacted with compound 33 (0.16 g, 0.383 mmol) according to Procedure F' to afford crude which was purified by column chromatography using 10-15% MeOH in DCM to afford compound 35 (0.12 g, 80%). $^1$H NMR (600 MHz, CD$_3$OD) δ ppm 6.55 (d, J=8.4 Hz, 1H), 6.51 (d, J=3.0 Hz, 1H), 6.41 (dd, J=8.4, 3.0 Hz, 1H), 3.0 (m, 1H), 2.44-2.63 61 (m, 10H), 1.98 (d, J=10.2 Hz, 1H), 1.65-1.68 (m, 1H), 1.56-1.61 (m, 2H), 1.44-1.52 (m, 4H), 1.32-1.36 (m, 2H), 0.88 (t, J=7.2 Hz, 3H). The free base was converted into its corresponding hydrochloride salt. Mp 217-219° C. Anal. ($C_{21}H_{35.8}N_3Cl_3O_{2.9}S$) C, H, N.

(R)-2-(5-((2-Amino-4,5,6,7-tetrahydrobenzo[d]thiazol-6-yl)(propyl)amino)pentyl)benzene-1,4-diol (−35)

BBr$_3$ 1M in DCM (1.33 mL, 1.33 mmol) was reacted with compound (0.093 g, 0.222 mmol) in DCM (6 mL) according to Procedure F' to afford crude which was purified by column chromatography using 10-15% MeOH in DCM to give compound −35 (62 g, 72%). $^1$H NMR (600 MHz, CD$_3$OD) δ ppm 6.56 (dd, J=8.4, 1.8 Hz, 1H), 6.52 (d, J=2.4 Hz, 1H), 6.43 (dt, J=8.4, 1.80 Hz, 1H), 2.98-3.03 (m, 1H), 2.44-2.64 (m, 10H), 1.99-2.00 (m, 1H), 1.63-1.71 (m, 1H), 1.57-1.62 (m, 2H), 1.46-1.52 (m, 4H), 1.32-1.37 (m, 2H), 0.90 (t, J=7.2 Hz, 3H). The free base was converted into its corresponding hydrochloride salt. Mp 222-224° C. Anal. ($C_{21}H_{34}N_3Cl_3O_2S$) C, H, N.

Procedure G'. (Z)-ethyl 5-(4-((tert-butyldimethylsilyl)oxy)-3-methoxyphenyl)pent-4-enoate (36)

Imidazole (0.411 g, 6.03 mmol) was added to a solution of intermediate 26 (0.61 g, 2.41 mmol) and tert-butyldimethylsilyl chloride (0.437 g, 2.89 mmol) in DMF (5 mL). The solution was stirred at room temperature for 2 h. After the completion of reaction, saturated aq NaHCO$_3$ (10 mL) was added and stirred for another 30 min. The reaction mixture was extracted with DCM (2×50 mL). The combined organic layer was dried over sodium sulfate and concentrated in vacuo. The crude thus obtained was purified by column chromatography using 5% ethyl acetate in hexanes to afford compound (0.88 g) in quantitative yield. $^1$H NMR (400 MHz, CD$_3$OD) δ ppm 6.85 (s, 1H), 6.79 (d, J=8.0 Hz, 1H), 6.73 (d, J=8.4 Hz, 1H), 4.37 (d, J=11.2 Hz, 1H), 5.47-5.55 (m, 1H), 4.10 (m, J=7.2 Hz, 2H), 3.78 (s, 3H), 2.63 (q, J=7.2 Hz, 2H), 2.44 (t, J=7.2 Hz, 2H), 1.20 (t, J=7.2 Hz, 3H), 0.99 (s, 9H), 0.13 (s, 6H).

Procedure H'. (Z)-5-(4-((tert-butyldimethylsilyl)oxy)-3-methoxyphenyl)pent-4-en-1-ol (37)

Into a stirring solution of compound (0.86 g, 2.34 mmol) in anhydrous THF (15 mL) was added DIBAL-H solution 1 M in THF (11.8 mL, 11.8 mmol) dropwise at −10° C. The reaction mixture was stirred at room temperature for 6 h and was quenched with methanol (1 mL). The mixture was acidified to neural with 1N HCl (15 mL) solution. The organic layer was separated and the aqueous layer was extracted with ethyl acetate (2×100 mL). The combined organic layer was dried over sodium sulfate and concentrated in vacuo. The crude product was purified by column chromatography using 11-15% ethyl acetate in hexanes to give compound (0.63 g, 87%). $^1$H NMR (CDCl$_3$, 400 MHz) δ ppm 6.74-6.85 (m, 3H), 6.37 (d, J=11.2 Hz, 1H), 5.48-5.53 (m, 1H), 3.80 (s, 3H), 2.67 (q, J=7.2 Hz, 2H), 2.43 (t, J=7.2 Hz, 2H), 1.22 (t, J=7.2 Hz, 2H), 1.06 (s, 9H), 0.15 (s, 6H).

Procedure I'. (Z)-5-(4-((tert-butyldimethylsilyl)oxy)-3-methoxyphenyl)pent-4-enal (38)

Alcohol (0.9 g, 2.46 mmol) was slowly added to a ice cooled suspension of PCC (0.707 g, 3.28 mmol) in DCM (90 mL) and the mixture was stirred at rt for 9 h. The reaction mixture was then filtered over celite and solvent was evaporated to get residue which was purified by column chromatography using 10-15% of ethyl acetate in hexanes to give compound 15 (0.358 g, 45%). $^1$H NMR (CDCl$_3$, 400 MHz) δ ppm 9.78 (s, 1H), 6.74-6.85 (m, 3H), 6.37 (d, J=11.2 Hz, 1H), 5.49-5.52 (m, 1H), 3.80 (s, 3H), 2.56-2.68 (m, 4H), 0.99 (s, 9H), 0.16 (s, 6H).

(Z)-4-(5-((2-amino-4,5,6,7-tetrahydrobenzo[d]thiazol-6-yl)(propyl)amino)pent-1-en-1-yl)-2-methoxyphenol (39)

Compound 38 (0.315 g, 0.982 mmol) was dissolved in THF (5 mL) and cooled to 0° C. TBAF 1M in THF (1.02 mL, 1.02 mmol) was added and reaction stirred in ice for 1.5 h. After reaction was complete, 10% NaHCO$_3$ solution (10 mL) was added and reaction mixture was extracted with DCM (3×50 mL) to obtain aldehyde which was immediately taken to the next step without further purification. Aldehyde (0.195 g, 0.945 mmol), (±) Pramipexole (0.20 g, 0.946 mmol), and NaBH(OAC)$_3$ (0.36 g, 1.69 mmol) in DCM (7 mL) and MeOH (1.0 mL) were reacted using procedure D' and the resulting crude was purified by column chromatography using 5-7% MeOH in DCM to give compound 39 (0.148 g, 39%). $^1$H NMR (400 MHz, CD$_3$OD) δ ppm 6.86 (d, J=8.0 Hz, 1H), 6.76-6.82 (m, 2H), 6.35 (d, J=12.4 Hz, 1H), 5.49-5.56 (m, 1H), 4.98 (bs, 1H), 3.86 (s, 3H), 3.1 (bs, 1H), 2.50-2.71 (m, 8H), 2.37 (q, J=7.2 Hz, 2H), 2.03 (bs, 1H), 1.44-1.70 (m, 5H), 0.88 (t, J=7.2 Hz, 3H). The free base was converted into its corresponding hydrochloride salt. Mp 212-214° C. Anal. ($C_{22}H_{34.4}N_3Cl_3O_{2.2}S$) C, H, N.

Figure 15:
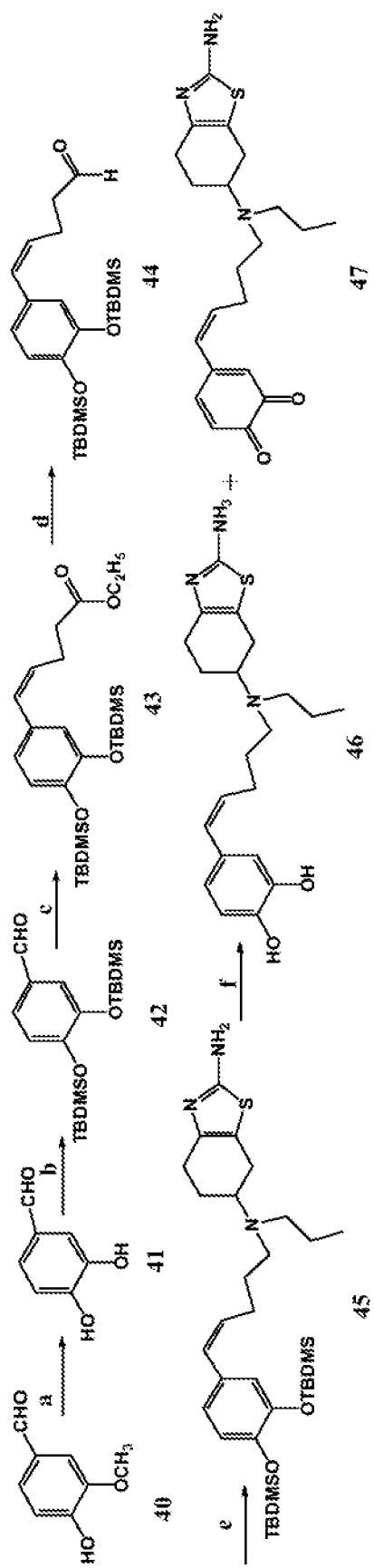
FIG. 15 provides a synthetic scheme for compounds having formula II.

FIG. 15 provides a synthetic scheme for the compounds having formula II, specifically for compound 47. The reaction conditions for this scheme are: (a) BBr$_3$, DCM, −78° C. to rt, 6 h, 87%; (b) TBDMSCl, imidazole, DMF, rt, 2 h, 67%;

(c) Phosphonium bromide 2, THF, −78° C. to rt, 48 h; 39%; (d) DIBALH, toluene, −78° C., 2 h, 45%; (e) Pramipexole, NaBH(OAc)$_3$, DCM, rt, 36 h, 50%; (f) TBAF, THF, 0° C., 1.5 h, 72%.

3,4-dihydroxybenzaldehyde (41)

Vanillin 40 (3.0 g, 18.0 mmol) was reacted with BBr$_3$ 1M in DCM (36.1 mL, 36.1 mmol) in DCM (20 mL) following Procedure F'. The crude obtained was purified by column chromatography using 20-25% ethyl acetate in hexanes to afford compound 41 (2.18 g, 87%). $^1$H NMR (400 MHz, CDCl$_3$) δ ppm 9.67 (s, 1H, CHO), 7.29 (m, 2H), 6.89 (d, J=9.2 Hz, 1H).

3,4-bis((tert-butyldimethylsilyl)oxy)benzaldehyde (42)

Imidazole (5.69 g, 83.5 mmol) was added to a solution of intermediate 41 (2.31 g, 16.7 mmol) and tert-butyldimethylsilyl chloride (6.30 g, 41.8 mmol) in DMF (20 mL). The solution was reacted using Procedure G'. The crude thus obtained was purified by column chromatography using 5% ethyl acetate in hexanes to afford compound 42 (4.10 g, 67%). $^1$H NMR (400 MHz, CDCl$_3$) δ ppm 9.80 (s, 1H, CHO), 7.36 (m, 2H), 6.93 (d, J=8.8 Hz, 1H), 0.99 (s, 9H), 0.98 (s, 9H), 0.24 (s, 6H), 0.22 (s, 6H).

(Z)-ethyl 5-(3,4-bis((tert-butyldimethylsilyl)oxyphenyl)pent-4-enoate (43)

Starting material 25 (5.48 g, 11.98 mmol) was reacted with compound 42 (4.0 g, 10.90 mmol) in presence of NaHMDS 1M in THF (13.07 mmol, 13.07 mL) according to Procedure A'. The crude was purified by column chromatography using 5% ethyl acetate in hexanes to give compound 20 (2.0 g, 39%). $^1$H NMR (400 MHz, CDCl$_3$) δ ppm 6.81 (m, 2H), 6.73 (d, J=8.4 Hz, 1H), 6.30 (d, J=11.4 Hz, 1H), 5.46-5.50 (m, 1H), 4.12 (q, J=7.3 Hz, 2H), 2.64 (q, J=7.2 Hz, 2H), 2.41 (t, J=7.2 Hz, 2H), 1.24 (t, J=7.2 Hz, 3H), 0.97 (s, 18H), 0.19 (s, 6H), 0.18 (s, 6H).

(Z)-ethyl 5-(3,4-bis((tert-butyldimethylsilyl)oxyphenyl)pent-4-enal (44)

Intermediate 43 (1.0 g, 2.15 mmol) was reduced with DIBALH solution 1M in hexane (2.16 mL, 2.16 mmol) in dry toluene (15 mL) using procedure D'. The crude was purified by column chromatography using 10% ethyl acetate in hexane to give compound 44 (0.41 gm, 45%) as yellow oil. $^1$H NMR (600 MHz, CDCl$_3$) δ ppm 9.76 (s, 1H), 6.77-6.79 (m, 2H), 6.73 (td, J=7.2, 2.4 Hz, 1H), 6.33 (d, J=11.4 Hz, 1H), 5.45-5.50 (m, 1H), 2.65 (q, J=7.2 Hz, 2H), 2.56 (t, J=7.2 Hz, 2H), 0.98 (s, 18H), 0.20 (s, 12H).

(Z)—N$^6$-(5-(3,4-bis((tert-butyldimethylsilyl)oxy)phenyl)pent-4-en-1-yl)-N$^6$-propyl-4,5,6,7-tetrahydrobenzo[d]thiazole-2,6-diamine (45)

Aldehyde 44 (0.3 g, 0.71 mmol), (±) Pramipexole (0.15 g, 0.71 mmol), and NaBH(OAc)$_3$ (0.27 g, 1.27 mmol) in DCM (10 mL) and MeOH (0.8 mL) were reacted using procedure E' and the resulting crude was purified by column chromatography using 5% MeOH in DCM to give compound 45 (0.22 g, 50%). $^1$H NMR (600 MHz, CD$_3$OD) δ ppm 6.79 (m, 2H), 6.73 (d, J=7.8 Hz, 1H), 6.29 (d, J=11.4 Hz, 1H), 5.52 (m, 1H), 3.09 (bs, 1H), 2.44-2.66 (m, 8H), 2.34-2.37 (m, 2H), 1.96-1.99 (m, 1H), 1.60-1.72 (m, 3H), 1.44-1.51 (m, 2H), 0.97 (s, 18H), 0.87 (t, J=7.2 Hz, 3H), 0.18 (s, 12H).

Procedure J'. (Z)-4-(5-((2-amino-4,5,6,7-tetrahydrobenzo[d]thiazol-6-yl)(propyl)amino)pent-1-en-1-yl)benzene-1,2-diol and 4-(5-((2-amino-4,5,6,7-tetrahydrobenzo[d]thiazol-6-yl)(propyl)amino)pent-1-enyl)-[1,2]benzoquinone (mixture of 46 and 47)

Compound (0.21 g, 0.34 mmol) was dissolved in THF (5 mL) and cooled to 0° C. TBAF 1M in THF (1.02 mL, 1.02 mmol) was added and reaction stirred in ice for 1.5 h. After reaction was complete, 10% NaHCO$_3$ solution (10 mL) was added and reaction mixture was extracted with DCM (3×50 mL). The combined organic layer was dried over sodium sulfate and concentrated in vacuo. The crude was purified by column chromatography using 15-20% MeOH in DCM (0.095 g, 72%). $^1$H NMR (600 MHz, CD$_3$OD) δ ppm 6.79 (s, 1H), 6.73 (s, 1H), 6.70 (d, J=7.8 Hz, 1H), 6.63 (m, 2H), 6.59 (d, J=8.4 Hz, 1H), 6.20-6.25 (m, 2H), 6.59 (dt, J=15.6, 7.2 Hz, 1H), 5.46 (m, 1H), 3.0 (bs, 2H), 2.40-2.63 (m, 16H), 2.32 (m, 2H), 2.16 (m, 2H), 1.95 (m, 2H), 1.56-1.70 (m, 6H), 1.41-1.51 (m, 4H), 0.85-0.90 (m, 6H). The free base was converted into its corresponding hydrochloride salt. Mp 212-214° C. Anal. (C$_{22}$H$_{34.4}$N$_3$Cl$_3$O$_{2.2}$S) C, H, N.

Figure 16:
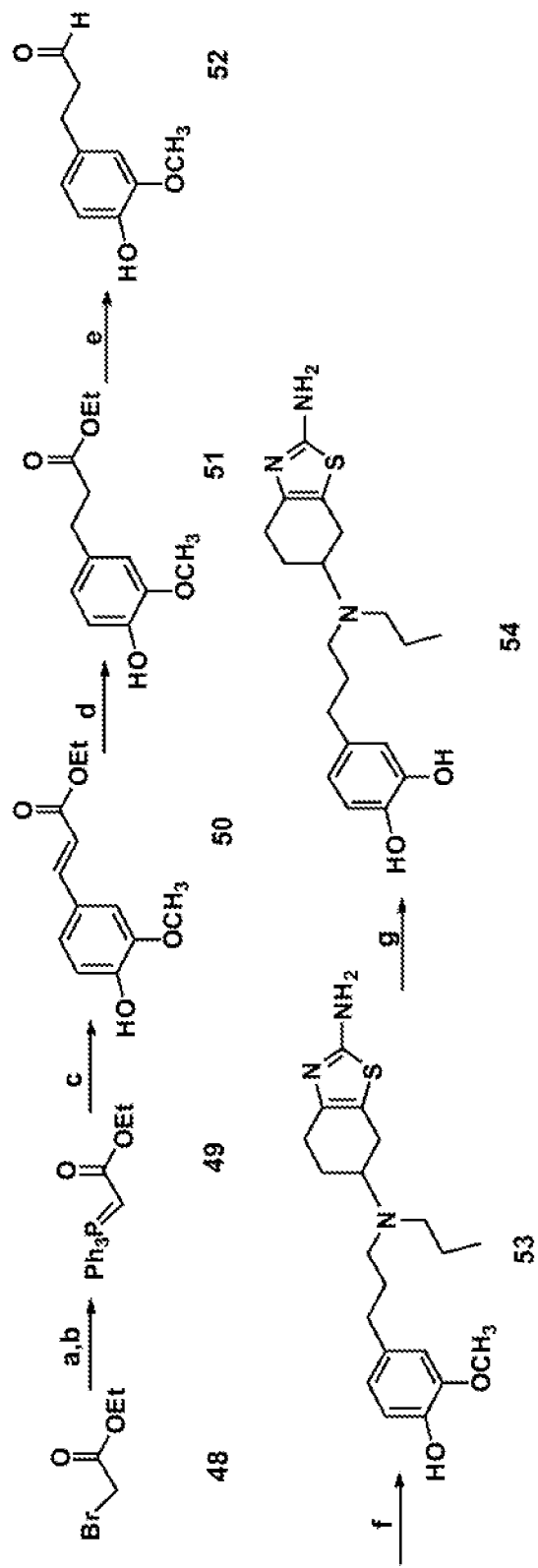
FIG. 16 provides a synthetic scheme for compounds having formula II.

FIG. 16 provides a synthetic scheme for the compounds having formula II, specifically for compound 54. The reaction conditions for this scheme are: (a) TPP, toluene, reflux, 16 h, 87%; (b) 1 M NaOH aq., 15 min, 88%; (c) Vanillin, DCM, reflux, 5 h, 85% (d) 10% pd/C, H$_2$, ethanol, rt, 2 h, quant. yield; (d) DIBALH, toluene, −78° C., 2 h, 45%; (e) Pramipexole, NaBH(OAc)$_3$, DCM, rt, 36 h, 46%; (f) BBr$_3$, DCM 0° C.-rt, 6 h, 63%.

(ethyl 2-(triphenylphosphoranylidene)acetate (49)

Ethyl bromoacetate (1.98 mL, 17.90 mmol) was slowly added to a stirring solution of triphenylphosphine (5.64 g, 21.50 mmol) in toluene (20 mL). The reaction mixture was refluxed for 16 h and filtered. The filter cake was washed with ethyl acetate (3×20 mL) to give phosphonium bromide (6.69 g, 87%). Into a solution of phosphonium bromide (6 g, 13.98 mmol) in DCM (50 mL) was added an aqueous solution of NaOH (1.0 M, 50 mL). The mixture was vigorously stirred for 15 min and the layers were separated. The aqueous layer was extracted with DCM (3×15 mL). The combined organic phase was dried over Na$_2$SO$_4$ and concentrated to give compound 49 (4.28 g, 88%). $^1$H NMR (CDCl$_3$, 400 MHz): δ (0.65, minor+1.21, major) (t, J=7.2 Hz, 3H), (2.70, minor+2.92, major) (d, J=22 Hz, 1H), (3.80, minor+4.01, major) (q, J=7.2 Hz, 2H), 7.40-7.77 (m, 15H).

Ethyl 3-(4-hydroxy-3-methoxyphenyl)acrylate (50)

Intermediate 49 (3.10 g, 7.23 mmol) was reacted with NaHMDS (1M in THF, 7.88 mL, 7.88 mmol) and Vanillin (1.0 g, 6.57 mmol) in anhydrous THF (8 mL) according to Procedure B' The crude thus obtained was purified by column chromatography using 7-10% ethyl acetate in hexanes to yield compound 50 (1.25 g, 85%) as colorless oil with a preferential Z:E ratio of >20:1: $^1$H NMR (400 MHz, CDCl$_3$) δ ppm 7.03 (m, ArH, 2H), 6.91 (d, J=8.0 Hz, ArH, 1H), 6.29 (d, J=15.2 Hz, 1H), 5.83 (m, 1H), 4.25 (q, J=7.2 Hz, OCH$_2$, 2H), 3.92 (s, OCH$_3$, 3H), 1.33 (t, J=7.6 Hz, 3H).

Ethyl 3-(4-hydroxy-3-methoxyphenyl)propanoate (51)

Intermediate 50 (1.0 g, 4.45 mmol) was dissolved in ethanol (10 mL) in a round bottom flask and 10% Pd/C (0.10 g, 10 wt %) was added to it. The reaction was continued using Procedure C'. After the completion of reaction, the mixture was diluted with ethanol (20 mL) and passed through a short bed of celite. The organic layer was concentrated to afford compound 51 (0.95 gm) as colorless oil in quantitative yield which was pure enough for the next step. $^1$H NMR (400 MHz, CDCl$_3$) δ ppm 6.82 (d, J=7.2 Hz, 1H), 6.68 (m, 2H), 4.12 (q, J=7.2 Hz, 2H), 3.84 (s, 3H), 2.87 (t, J=7.6 Hz, 2H), 2.58 (t, J=8.0 Hz, 2H), 1.23 (t, J=7.2 Hz, 3H).

3-(4-Hydroxy-3-methoxyphenyl)propanal (52)

Intermediate 51 (0.60 g, 2.67 mmol) was reduced with DIBALH solution (1M in hexane, 2.93 mL, 2.93 mmol) in dry toluene (10 mL) using procedure D'. The crude was purified by column chromatography using 12-15% ethyl acetate in hexanes to give compound 52 (0.22 gm, 45%) as yellow oil. $^1$H NMR (400 MHz, CDCl$_3$) δ ppm 9.81 (t, J=1.6 Hz, 1H), 6.83 (d, J=7.2 Hz, 1H), 6.68 (m, 2H), 3.87 (s, 3H), 2.89 (t, J=7.6 Hz, 2H), 2.75 (t, J=8.0 Hz, 2H).

4-(3-((2-Amino-4,5,6,7-tetrahydrobenzo[d]thiazol-6-yl)(propyl)amino)propyl)-2-methoxyphenol (53)

Aldehyde 52 (0.30 g, 1.66 mmol), (±) Pramipexole (0.369 g, 1.74 mmol), and NaBH(OAc)$_3$ (0.633 g, 2.98 mmol) in DCM (10 mL) and MeOH (1 mL) were reacted using procedure E' and the resulting crude was purified by column chromatography using 5-7% MeOH in DCM to give compound 53 (0.2 g, 46%). $^1$H NMR (400 MHz, CD$_3$OD) δ ppm 6.79 (s, 1H), 6.71 (d, J=8.0 Hz, 1H), 6.64 (d, J=8.0 Hz, 1H), 3.82 (s, 3H), 2.73-2.89 (m, 5H), 2.57-2.67 (m, 6H), 2.05-2.12 (m, 1H), 1.81-1.92 (m, 3H), 1.59 (m, 2H), 0.95 (t, J=7.2 Hz, 3H). The free base was converted into its corresponding hydrochloride salt. Mp 220-222° C. Anal. (C$_{20}$H$_{32}$Cl$_2$N$_3$O$_{2.5}$S) C, H, N.

4-(3-((2-Amino-4,5,6,7-tetrahydrobenzo[d]thiazol-6-yl)(propyl)amino)propyl)-benzene-1,4-diol (54)

BBr$_3$ 1M in DCM (2.66 mL, 2.66 mmol) was reacted with compound 53 (0.2 g, 0.532 mmol) according to Procedure F' to afford crude which was purified by column chromatography using 15-20% MeOH in DCM to provide compound 54 (0.12 g, 63%) $^1$H NMR (400 MHz, CD$_3$OD) δ ppm 6.57 (d, J=8.4 Hz, 1H), 6.53 (s, 1H), 6.41 (d, J=8.4 Hz, 1H), 3.13 (bs, 1H), 2.39-2.66 (m, 10H), 1.95 (m, 1H), 1.61-1.75 (m, 3H), 1.41-1.47 (m, 2H), 0.82 (t, J=7.2 Hz, 3H). The free base was converted into its corresponding hydrochloride salt. Mp 192-194° C. Anal. (C$_{19}$H$_{30.6}$N$_3$Cl$_3$O$_{2.3}$S) C, H, N.

Elemental Analysis Report of Final Compounds

Figure 17:
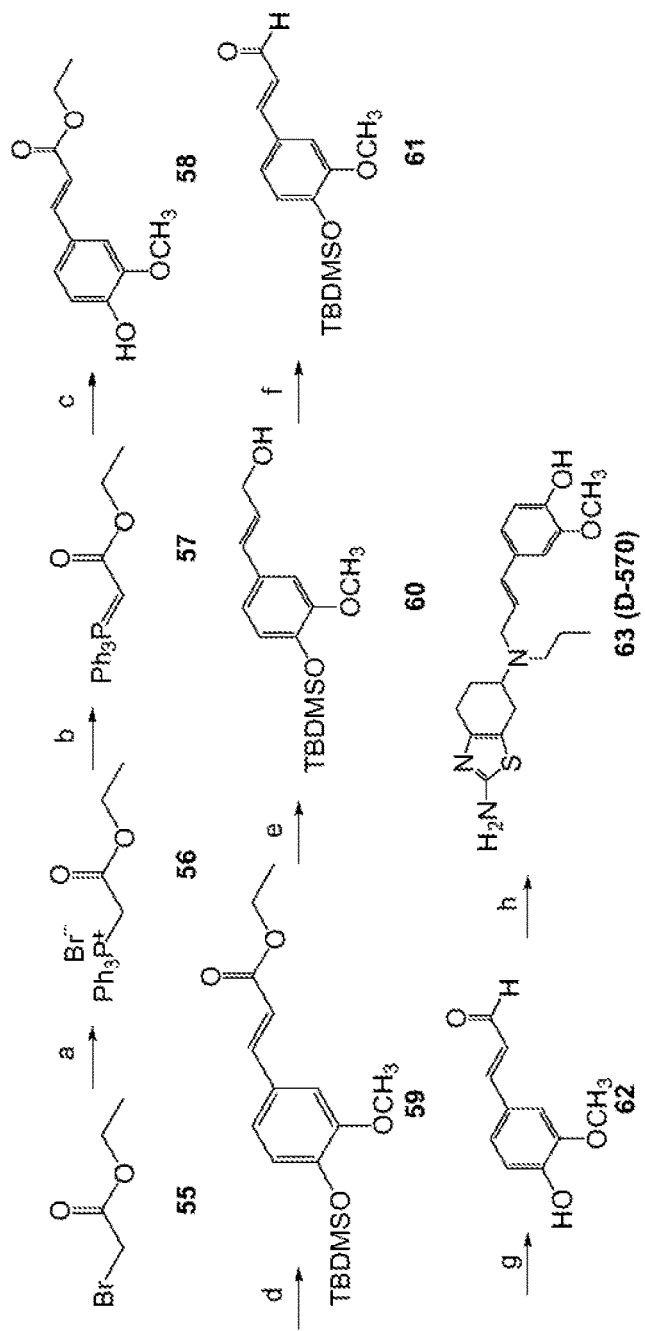
FIG. 17 provides a synthetic scheme for compounds having formula II.

FIG. 17 provides a synthetic scheme for the compounds having formula II, specifically for compound 63. The conditions for this scheme are: (a) TPP, toluene, reflux, 16 h, 87%; (b) 1 M NaOH aq., 15 min, 88%; (c) vanillin, CHCl$_3$, reflux, 5 h, 85%; (d) TBDMSCl, imidazole, DMF, rt, 2 h, 90%; (e) DIBALH, THF, −10° C. to rt, 6 h, 94%; (f) MnO$_2$, DCM, rt, 24 h, 84%; (g) TBAF, THF, 0° C., 1 h, 84%; (h) (±) Pramipexole, NaBH(OAc)$_3$, DCM, rt, 48 h, 30%.

(2-ethoxy-2-oxoethyl)triphenylphosphonium bromide (56)

Ethyl bromoacetate (1.98 mL, 17.90 mmol) was slowly added to a stirring solution of triphenylphosphine (5.64 g, 21.50 mmol) in toluene (20 mL). The reaction mixture was refluxed for 16 h and filtered. The filter cake was washed with ethyl acetate (3×20 mL) to give compound 2 (6.69 g, 87%). $^1$H NMR (CDCl$_3$, 400 MHz): δ 1.04 (t, J=7.2 Hz, 3H), 4.01 (q, J=7.2 Hz, 2H), 5.54 (d, J=13.6 Hz, 2H), 7.64-7.91 (m, 15H).

ethyl 2-(triphenylphosphoranylidene)acetate (57)

Into a solution of phosphonium bromide 54 (6 g, 13.98 mmol) in DCM (50 mL) was added an aqueous solution of NaOH (1.0 M, 50 mL). The mixture was vigorously stirred for 15 min and the layers were separated. The aqueous layer was extracted with DCM (3×15 mL). The combined organic phase was dried over Na$_2$SO$_4$ and concentrated to give compound 57 (4.28 g, 88%). $^1$H NMR (CDCl$_3$, 400 MHz): δ (0.65, minor+1.21, major) (t, J=7.2 Hz, 3H), (2.70, minor+2.92, major) (d, J=22 Hz, 1H), (3.80, minor+4.01, major) (q, J=7.2 Hz, 2H), 7.40-7.77 (m, 15H).

(E)-ethyl 3-(4-hydroxy-3-methoxyphenyl)acrylate (58)

A mixture of vanillin (1.65 g, 10.84 mmol) and phosphonium ylide 57 (4.08 g, 11.71 mmol) was refluxed in chloroform (30 mL) for 5 h. The solvent was removed and the crude product was purified by column chromatography (17% ethyl acetate in Hexane) to give compound 58 (2.05 g, 85%). $^1$H NMR (CDCl$_3$, 400 MHz): δ 1.19 (t, J=7.2 Hz, 3H), 3.70 (s, 3H), 4.13 (q, J=7.0 Hz, 2H), 6.17 (d, J=15.7 Hz, 1H), 6.75-6.92 (m, 3H), 7.49 (d, J=15.9 Hz, 1H).

(E)-ethyl 3-(4-((tert-butyldimethylsilyl)oxy)-3-methoxyphenyl)acrylate (59)

A solution of compound 58 (1.78 g, 8.01 mmol), tert-butyldimethylsilyl chloride (1.45 g, 9.62 mmol), and Imidazole (1.36 g, 19.98 mmol) in DMF (6 mL) was stirred at

| Compound | Calculated | | | Found | | |
| --- | --- | --- | --- | --- | --- | --- |
| | C | H | N | C | H | N |
| (9)•2HCl•0.58C$_2$H$_5$OH•0.22CH$_3$SOCH$_3$ (D-548) | 4.47 | 7.71 | 8.07 | 4.86 | 7.31 | 7.60 |
| (−9)•2HCl•H$_2$O | 53.43 | 7.34 | 8.75 | 51.97 | 7.25 | 4.41 |
| (11)•3HCl (D-585) | 50.55 | 6.87 | 8.42 | 50.33 | 7.01 | 8.53 |
| (−11)•2HCl•H$_2$O | 52.49 | 7.34 | 8.75 | 51.97 | 7.25 | 8.41 |
| (12)•3HCl•0.9H$_2$O (D-594) | 48.96 | 7.00 | 8.16 | 49.35 | 6.76 | 7.75 |
| (−12)•3HCl (D-601) | 50.55 | 6.87 | 8.42 | 50.26 | 7.14 | 8.23 |
| (16)•3HCl•0.2H$_2$O (D-567) | 51.35 | 6.74 | 8.17 | 51.65 | 7.16 | 7.63 |
| (23)•3HCl | 50.76 | 6.49 | 8.46 | 50.07 | 7.33 | 7.97 |
| (30)•2HCl•0.5H$_2$O (D-547) | 52.51 | 7.05 | 9.19 | 52.12 | 7.19 | 8.83 |
| (31)•3HCl•0.3H2O (D-583) | 47.91 | 6.48 | 8.82 | 47.86 | 6.87 | 9.23 | room temperature for 2 h. Then the mixture was extracted with water and diethyl ether. The organic phase was washed with brine and dried over $Na_2SO_4$. Then it was concentrated to give compound 5 (2.42 g, 90%). $^1$H NMR ($CDCl_3$, 400 MHz): δ 0.17 (s, 6H), 0.99 (s, 9H), 1.33 (t, J=7.2 Hz, 3H), 3.83 (s, 3H), 4.25 (q, J=7.1 Hz, 2H), 6.30 (d, J=16.0 Hz, 1H), 6.84 (d, J=8.8 Hz, 1H), 6.99-7.03 (m, 2H), 7.62 (d, J=15.2 Hz, 1H).

(E)-3-(4-((tert-butyldimethylsilyl)oxy)-3-methoxyphenyl)prop-2-en-1-ol (60)

Into a stirring solution of compound 59 (2.4 g, 7.13 mmol) in anhydrous THF (30 mL) was added DIBAL-H solution (1 M in THF, 35.7 mL, 35.7 mmol) dropwise at −10° C. The reaction mixture was stirred at room temperature for 6 h and was quenched with methanol (1 mL). The mixture was acidified to neural with 1N HCl solution. The organic layer was separated and the aqueous layer was extracted with ethyl acetate (2×20 mL). The combined organic phase was dried over $Na_2SO_4$ and concentrated. The crude product was purified by column chromatography (25% ethyl acetate in Hexane) to give compound 60 (1.97 g, 94%). $^1$H NMR ($CDCl_3$, 400 MHz): δ 0.15 (s, 6H), 0.99 (s, 9H), 3.81 (s, 3H), 4.28 (d, J=5.6 Hz, 2H), 6.22 (dt, J=16.0, 6.0 Hz, 1H), 6.52 (d, J=15.6 Hz, 1H), 6.79 (d, J=8.0 Hz, 1H), 6.84 (dd, J=8.0, 1.6 Hz, 1H), 6.90 (d, J=1.6 Hz, 1H).

(E)-3-(4-((tert-butyldimethylsilyl)oxy)-3-methoxyphenyl)acrylaldehyde (61)

$MnO_2$ (3.54 g, 40.72 mmol) was added into a solution of compound 60 (0.8 g, 2.72 mmol) in DCM (15 mL). The mixture was stirred at room temperature for 24 h and was filtered through celite. The filter cake was washed with ethyl acetate and the filtrate was concentrated to give compound 61 (0.67 g, 84%). $^1$H NMR ($CDCl_3$, 400 MHz): δ 0.18 (s, 6H), 1.00 (s, 9H), 3.85 (s, 3H), 6.60 (dd, J=15.6, 7.6 Hz, 1H), 6.88 (d, J=7.2 Hz, 1H), 7.05-7.08 (m, 2H), 7.40 (d, J=16.0 Hz, 1H), 9.65 (d, J=7.2 Hz, 1H).

(E)-3-(4-hydroxy-3-methoxyphenyl)acrylaldehyde (62)

Into a stirring solution of compound 7 (0.67 g, 2.29 mmol) in THF (10 mL) at 0° C., TBAF solution (1 M in THF, 2.52 mL, 2.52 mmol) was added dropwise. The mixture was stirred for 1 h and was quenched with a saturated solution of $NaHCO_3$ (stirred for 30 min). The organic layer was separated and the aqueous layer was extracted with DCM (3×15 mL). The organic layer was dried over $Na_2SO_4$ and concentrated. The crude product was purified by column chromatography (35% ethyl acetate in Hexane) to give compound 62 (0.343 g, 84%). It was immediately taken to the next step.

(E)-4-(3-((2-amino-4,5,6,7-tetrahydrobenzo[d]thiazol-6-yl)(propyl)amino)prop-1-en-1-yl)-2-methoxyphenol (63)

A mixture of aldehyde 62 (0.334 g, 1.87 mmol) and (±) pramipexole (0.395 g, 1.87 mmol) in DCM (10 mL) was stirred for 1 h, and followed by the portionwise addition of $NaBH(OAc)_3$ (0.710 g, 3.35 mmol). Then the mixture was kept for stirring for 48 h at room temperature and was quenched with a saturated solution of $NaHCO_3$ afterwards at 0° C. The organic layer was separated and the aqueous layer was extracted with ethyl acetate (3×10 mL). The combined organic phase was dried over $Na_2SO_4$. The concentrated crude product was purified by column chromatography (15% methanol in DCM) to give compound 63 (0.21 g, 30%). $^1$H NMR ($CD_3OD$, 400 MHz): δ 1.03 (t, J=7.2 Hz, 3H), 1.72 (q, J=7.1 Hz, 2H), 1.81-2.00 (m, 2H), 2.23-2.33 (m, 1H), 2.58-2.67 (m, 1H), 2.79-2.90 (m, 3H), 2.99 (t, J=7.1 Hz, 2H), 3.25 (dd, J=15.6, 5.2 Hz, 1H), 3.46 (s, 1H), 3.89 (s, 3H), 6.81 (d, J=8.4 Hz, 1H), 6.92 (dd, J=15.2, 7.6 Hz, 1H), 7.10 (d, J=8.0 Hz, 1H), 7.20 (s, 1H), 7.36 (d, J=16.4 Hz, 1H). The free base was converted into its corresponding hydrochloride salt. Mp 205-207° C. Anal. ($C_{20}H_{32}Cl_3N_3O_3S$) C, H, N.

| Compound | Calculated | | | Found | | |
|---|---|---|---|---|---|---|
| | C | H | N | C | H | N |
| 9•3HCl•1H$_2$O | 47.96 | 6.44 | 8.39 | 48.24 | 6.35 | 8.29 |

Figure 18:
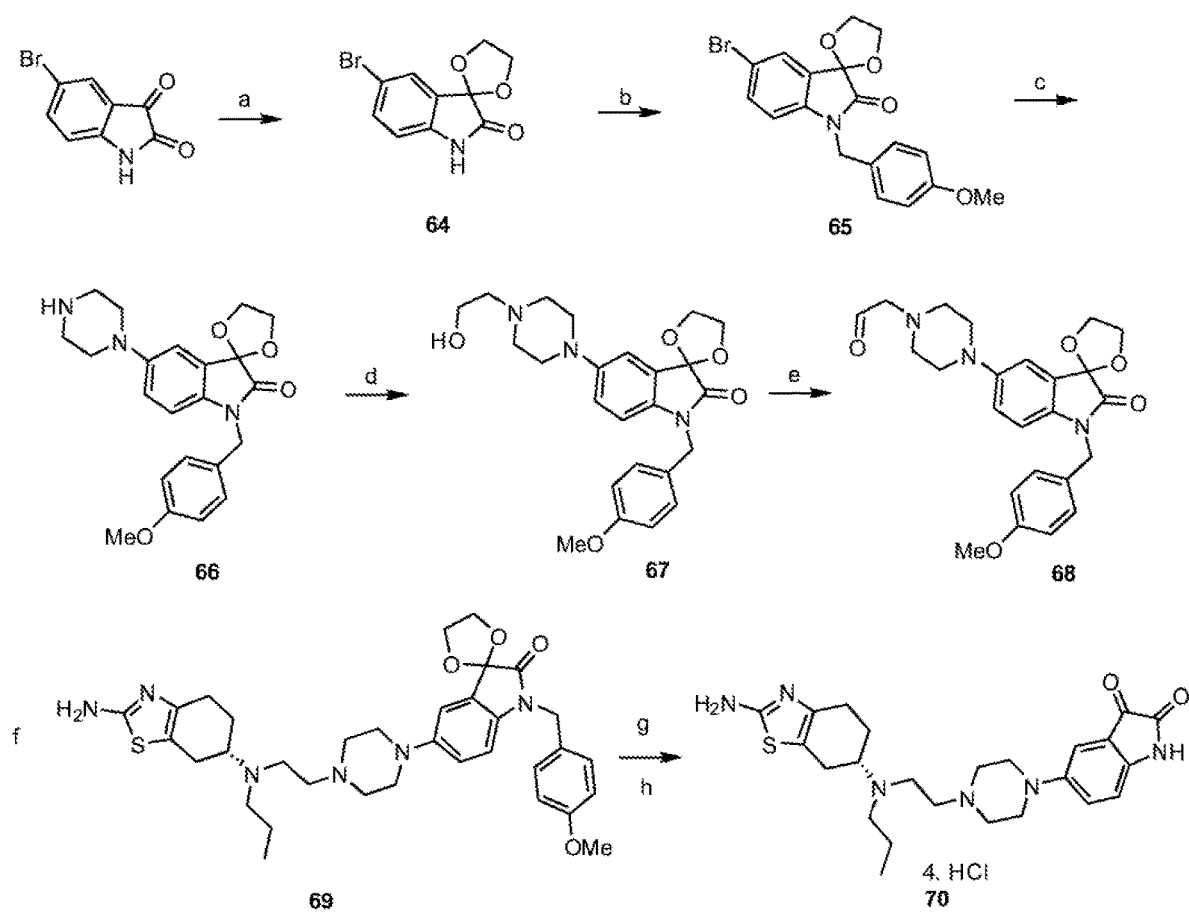
FIG. 18 provides a synthetic scheme for compounds having formula I.
Figure 19:
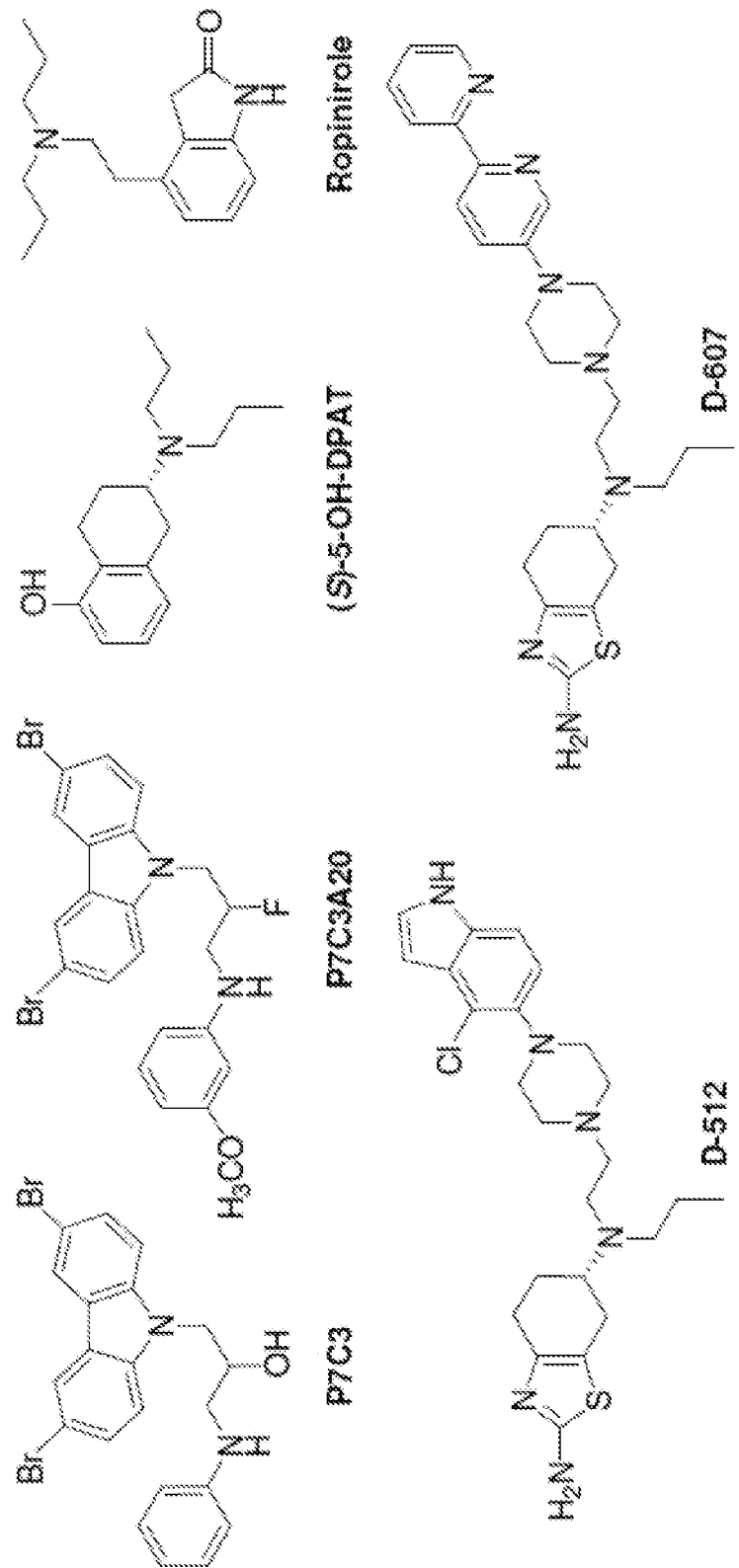
FIG. 19. Structures of carbazole compounds and D2/D3 receptor agonists.
Figure 20:
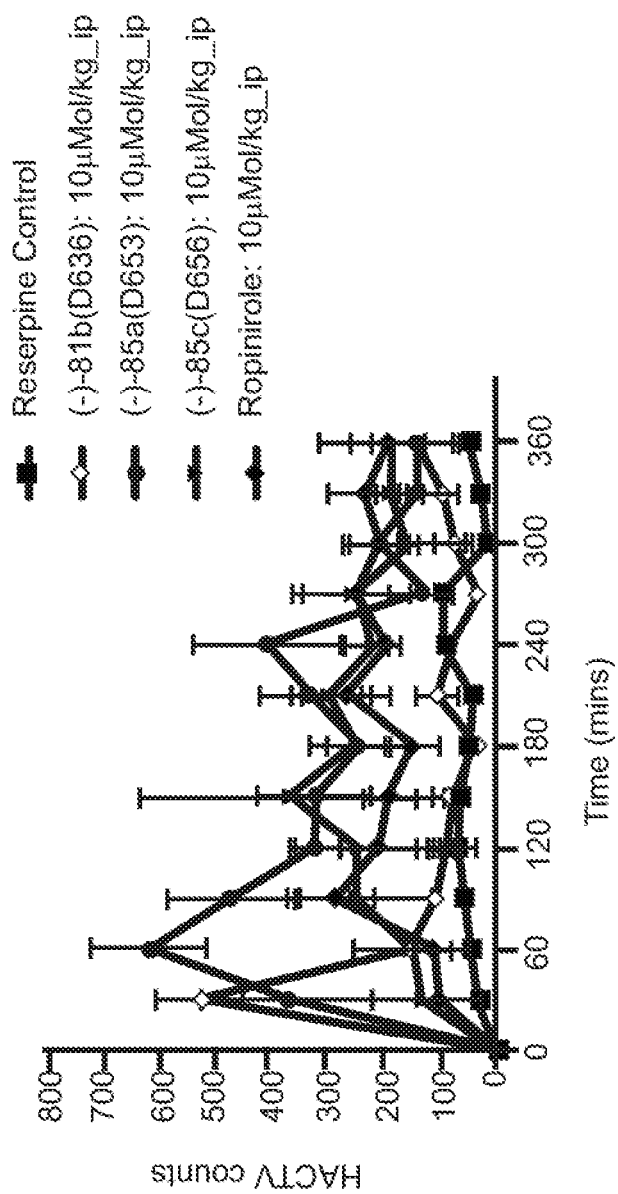
FIG. 20. Effects of different drugs upon reserpine (5.0 mg/kg, sc, 18 h pretreatment) induced hypolocomotion in rats. Each point represents the mean±SEM for three rats. Horizontal activity was measured as described in Experimental Section. Representation of horizontal locomotor activity is at discrete 30 min intervals after the administration of (−)-91b (D-636) (10 μMol/kg), (−)-95a (D-653) (10 μMol/kg), (−)-95c (D-656) (10 μMol/kg), and ropinirole (10 μMol/kg) compared to control rats, 18 h after reserpine treatment. Differences among treatments were significant by one-way ANOVA analysis (F (4, 60)=8.861; (P<0.0001)). Dunnett's analysis following ANOVA revealed that the effect of the compounds (−)-91b, (−)-95a and (−)-95c (p<0.0001) was significantly different when compared to reserpine control.
Figure 21A:
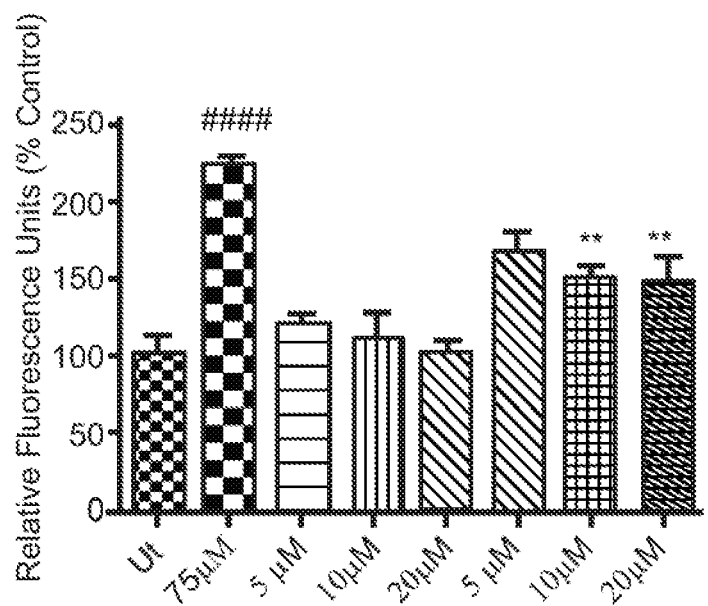
FIG. 21A-C. Detection of intracellular ROS using DCFDA-based fluorescence assay: PC12 cells were pre-treated with different doses of (−)-91b (D-636) (A), (−)-95a (D-653) (B), and (−)-95c (D-656) (C) for 24 h followed by treatment with DCFDA (20 μM, 2% serum) for 30 min. The DCFDA containing media was removed, and replaced with fresh media, followed by treatment with 75 μM 6-OHDA, and incubated for 1 h. Data represents mean±SDs of three independent experiments in four to six replicates. One-Way ANOVA analysis followed by Tukey's multiple comparison post hoc test was performed. (*P<0.05, P<0.01, *P<0.001, and ****P<0.0001 compared to the 6-OHDA, #####P<0.0001 compared to the control)
Figure 21B:
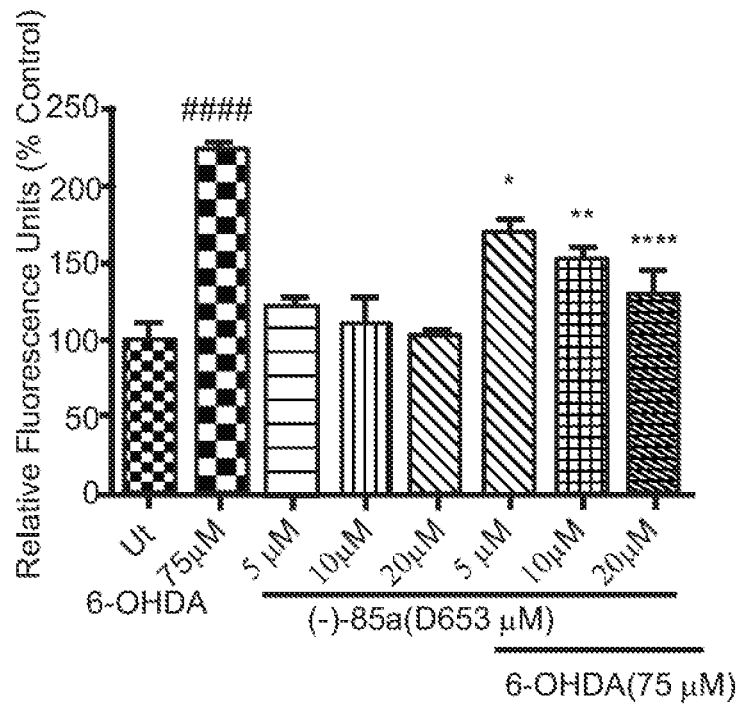
Figure 21C:
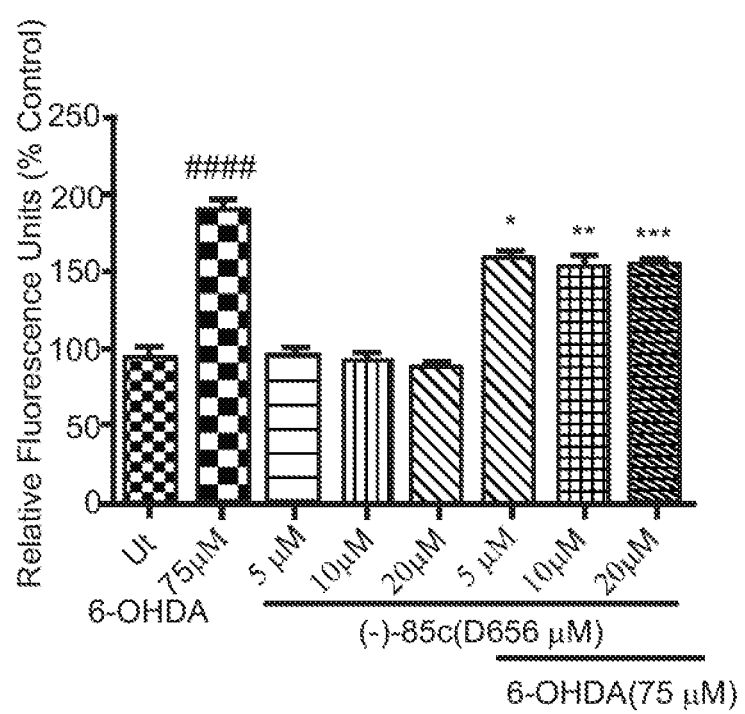
Figure 22A:
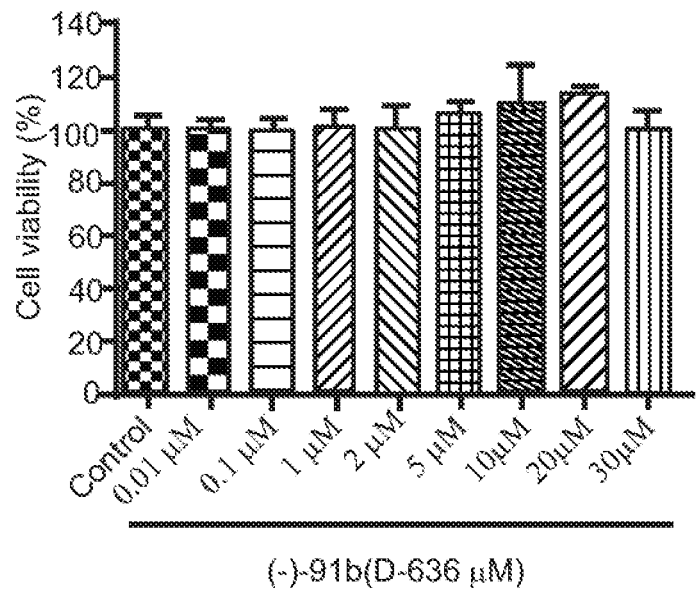
FIG. 22A-F. Dose-dependent effect on the viability of PC12 cells by 24 h pretreatment of compounds (−)-91b (D-636), (−)-95a (D-653), and (−)-95c (D-656) at various concentrations followed by single treatment of 75 μM 6-OHDA. (a, c and e) Dose-dependent effect of (−)-91b, (−)-95a, and (−)-95c on cell viability, respectively. (b, d and f) PC12 cells were pretreated with varying concentrations of (−)-91b, (−)-95a, and (−)-95c, respectively for 24 h followed by treatment with 75 M 6-OHDA for another 24 h. The results shown are mean±SEM of three independent experiments performed in seven to eight replicates. One way ANOVA analysis F (7, 54)=21.64, p<0.0001 for (−)-91b; F (7, 56)=167.5, p<0.0001 for (−)-95a; and F (7, 56)=39.78, p<0.0001 for (−)-95c. ANOVA was followed by Tukey's multiple comparison post hoc test (**p<0.0001, *p<0.001, **p<0.01 compared to control)
Figure 22B:
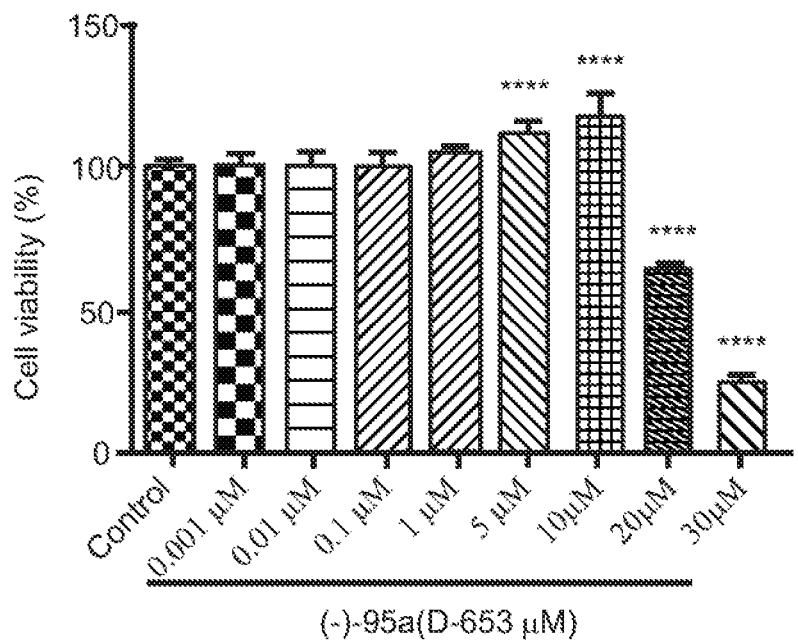
Figure 22C:
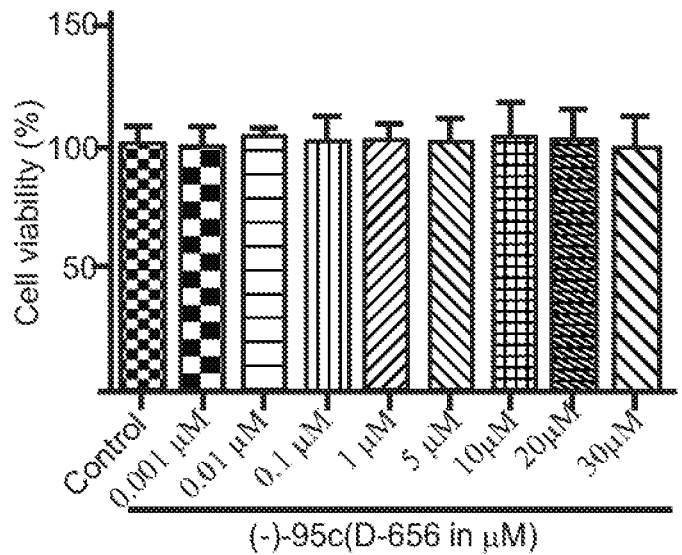
Figure 22D:
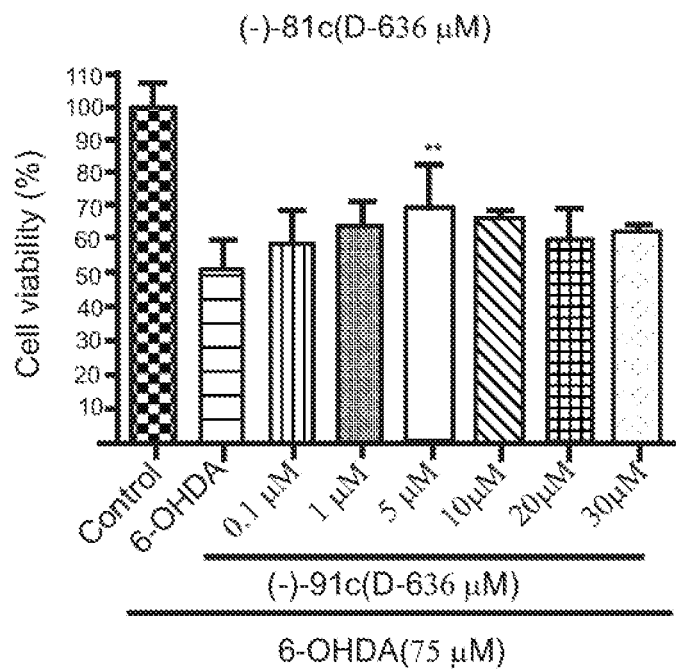
Figure 22E:
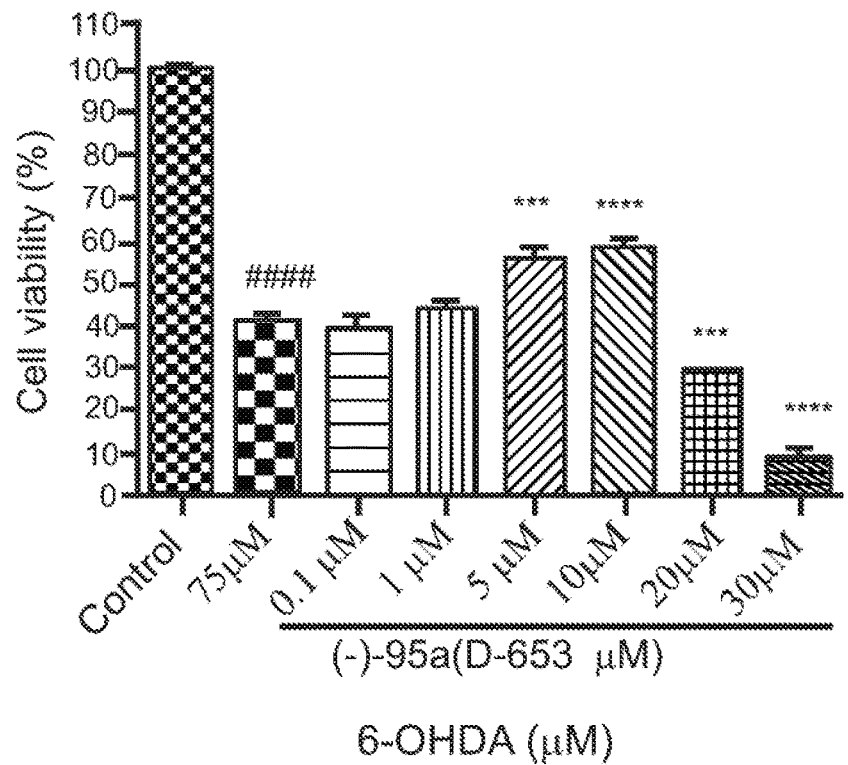
Figure 22F:
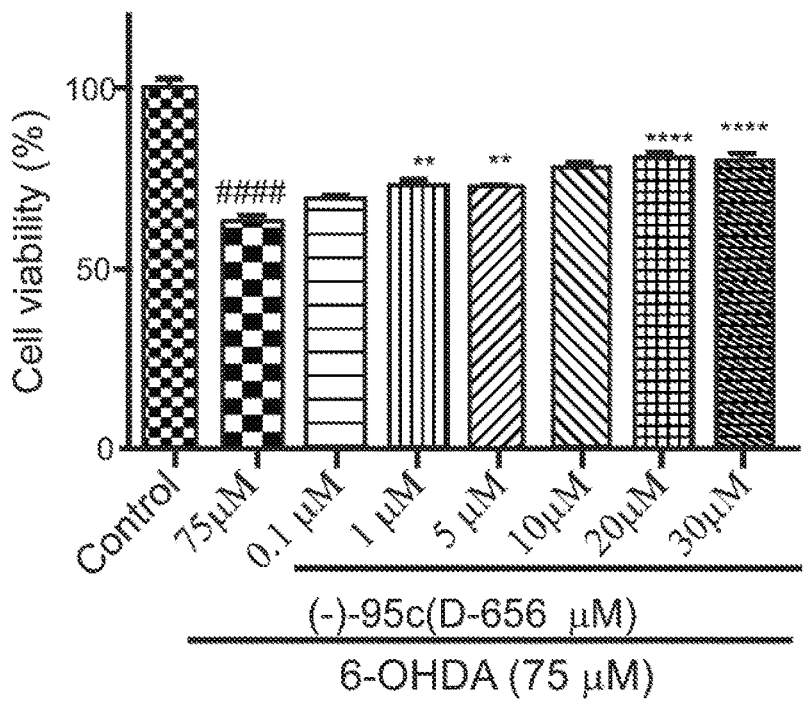
Figure 23A:
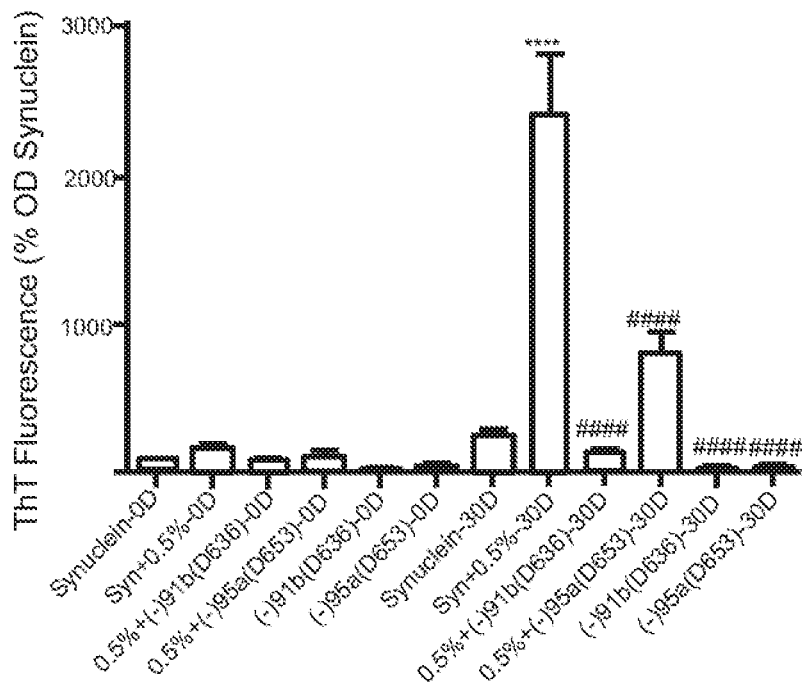
FIG. 23A-B. Effect of 91b (D-636) and 95a (D-653) on the aggregation of α-syn induced by seeding with 0.5% PFFs: 1.25 mg/mL α-syn was incubated with 0.5% PFFs for a period of 30D without shaking in the presence of 91b or 95a at a concentration of 172.9 μM. Fibrillation was measured by ThT assay at 30D (A). Values are represented in terms of % 0D Synuclein. Viability of PC12 cells was measured by MTT assay after 24 h treatment with α-syn seeded samples collected at 30D (B). Values are represented in terms of % control. Data values shown are means±SD of three independent experiments. One-way ANOVA analysis followed by Tukey's multiple comparison post hoc test was performed, p≤0.01, **p≤0.0001 compared to Syn +0.5%-0D; ####p<0.0001 compared to Syn +0.5%-30D.
Figure 23B:
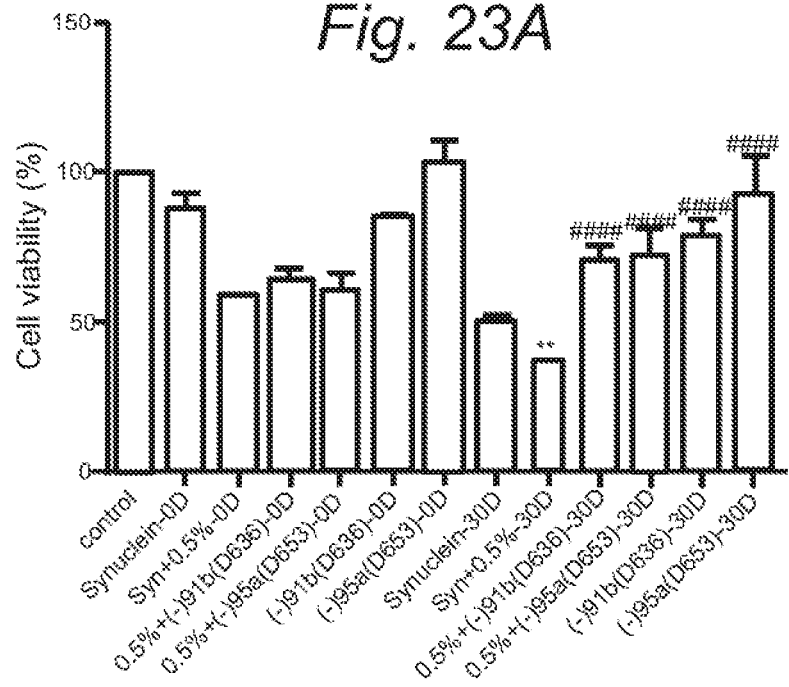

FIG. 18 provides a synthetic scheme for the compounds having formula I, specifically for compound 70.

Reagent and condition: (a) Ethylene glycol, Toluene, PTSA, reflux, 12 h; (b) 4-Methoxybenzylbromide, $K_2CO_3$, DMF, TBAI, rt, 12 h; (c) Piperazine, $Pd(OAc)_2$, BINAP, $Cs_2CO_3$, Toluene, reflux; (d) Bromoethanol, $K_2CO_3$, $CH_3CN$, reflux, 12 h; (e) $(COCl)_2$, DMSO, $Et_3N$, $CH_2Cl_2$, −78° C. to rt; (f) (±) (−) Pramipexole, $Na(OAc)_3BH$, $CH_2Cl_2$, 48 h; (g) 1:1 Conc. HCl, MeOH, sealed tube reflux, 12 h; (h) 2M HCl in ether, $CH_2Cl_2$.

5'-bromospiro[[1,3]dioxolane-2,3'-indolin]-2'-one (64)

To a solution of 5-bromoisatin (1 g, 4.42 mmol) in toluene (40 mL), ethylene glycol (4.9 mL, 84.48 mmol) and p-toluenesulphonic acid (38.1 mg, 0.22 mmol) were added. The reaction mixture was refluxed for 5 h and then evaporated to dryness. The residue was diluted with dichlormethane and washed with saturated sodium bicarbonate solution. The aqueous layer was extracted with dichloromethane three times. The combined organic extracts were dried over anhydrous sodium sulfate, filtered, and evaporated. The crude mixture was purified using column chromatography to yield 64. Yield: 99%. (C. H. Wang, A. R. White, S. N. Schwartz, S. Alluri, T. M. Cattabiani, L. K. Zhang, T. M. Chan, A. V. Buevich, A. K. Ganguly Tetrahedron 2012, 68, 9750-9762.)

5'-bromo-1'-(4-methoxybenzyl)spiro[[1,3]dioxolane-2,3'-indolin]-2'-one (65)

A mixture of compound 55 (1.75 g, 6.38 mmol), (4-Methoxybenzylbromide) (1.3 mL, 9.5 mmol), pinch of tetrabutylammonium iodide and $K_2CO_3$ (2.64 g g, 19.1 mmol) in DMF (15 mL) was stirred for 12 h. Quench the reaction mixture with ice cold water and extract with ethylacetate, dried over sodium sulfate and evaporated the crude material was purified by silica gel column chromatography (EtOAc/hexane, 3:1) to give compound 65 (2.25 g, 90%) $^1$H NMR (400 MHz, $CDCl_3$): δ 7.47 (d, J=1.6 Hz, 1H), 7.35 (dd, J$_1$=8.4 Hz, J$_2$=1.6 Hz, 1H), 7.18 (d, J=8.8 Hz, 2H), 7.35 (dd, J$_1$=8.4 Hz, J$_2$=1.6 Hz, 1H), 6.54 (d, J=8.0 Hz, 1H), 4.74 (s, 2H), 4.62-4.59 (m, 2H), 4.35-4.32 (m, 2H), 3.77 (s, 3H); $^{13}$C NMR (100 MHz, $CDCl_3$): δ 172.8, 159.2, 142.8, 134.2, 128.5 (2C), 128.1, 126.7, 115.8, 114.3 (2C), 111.2, 66.0, 55.2, 43.0.

1'-(4-methoxybenzyl)-5'-(piperazin-1-yl)spiro[[1,3]dioxolane-2,3'-indolin]-2'-one (66)

A mixture of 2 (1.2 g, 3.0 mmol), Piparazine (0.78 g, 9.1 mmol), Pd(OAc)$_2$ (0.034 g, 0.15 mmol), BINAP (0.142 g, 0.22 mmol) and Cs$_2$CO$_3$ (2.96 g, 9.2 mmol) in toluene (12 mL) was heated at 110° C. for 12 h. The reaction mixture was filtered through Celite, wash with dichloromethane and concentrated in vacuo. The crude residue was dissolved in ethylacetate and washed with water and evaporated to afford compound 66 (0.755 g, 62%). The crude residue was used for next step without purification. $^1$H NMR (400 MHz, CDCl$_3$): δ 7.19 (d, J=8.4 Hz, 2H), 7.01 (d, J=2.4 Hz, 1H), 6.81 (d, J=8.4 Hz, 2H), 6.77 (dd, J$_1$=8 Hz, J$_2$=2.4 Hz, 1H), 6.55 (d, J=8.8 Hz, 1H), 4.70 (s, 2H), 4.63-4.60 (m, 2H), 4.33-4.30 (m, 2H), 3.75 (s, 3H), 3.01 (d, J=5.6 Hz, 8H); 13C NMR (100 MHz, CDCl$_3$): δ 173.2, 159.0, 148.7, 136.8, 128.5 (2C), 127.4, 124.6, 119.4, 114.5 (2C), 110.1, 102.5, 65.8, 55.2, 51.1 (2C), 45.8 (2C), 42.9.

5'-(4-(2-hydroxyethyl)piperazin-1-yl)-1'-(4-methoxybenzyl)spiro[[1,3]dioxolane-2,3'-indolin]-2'-one (67)

A mixture of compound 57 (0.74 g, 1.86 mmol), (2-bromoethanol (0.26 mL, 3.7 mmol), and K$_2$CO$_3$ (0.76 g, 5.55 mmol) in CH$_3$CN (15 mL) was refluxed for 12 h. After filtration, acetonitrile was evaporated under reduced pressure and the crude material was purified by silica gel column chromatography (EtOAc/hexane, 3:1) to give compound 67 (0.631 g, 77%). $^1$H NMR (400 MHz, CDCl$_3$): δ 7.19 (d, J=9.2 Hz, 2H), 7.01 (d, J=2.4 Hz, 1H), 6.82 (d, J=9.2 Hz, 2H), 6.77 (dd, J$_1$=8 Hz, J$_2$=2.4 Hz, 1H), 6.56 (d, J=8 Hz, 1H), 4.71 (s, 2H), 4.63-4.60 (m, 2H), 4.34-4.31 (m, 2H), 3.75 (s, 3H), 3.76 (t, J=5.6 Hz, 2H), 3.53 (bs, 1H), 3.11 (t, J=4.8 Hz, 4H), 2.69 (t, J=4.8 Hz, 4H), 2.62 (t, J=5.6 Hz, 2H); 13C NMR (100 MHz, CDCl$_3$): δ 173.2, 159.0, 148.0, 136.9, 128.5 (2C), 127.3, 124.7, 119.3, 114.5, 114.1 (2C), 110.2, 102.5, 65.8 (2C), 59.3, 57.6, 55.2, 52.8 (2C), 49.9 (2C), 42.9.

2-(4-(1'-(4-methoxybenzyl)-2'-oxospiro[[1,3]dioxolane-2,3'-indolin]-5'-yl)piperazin-1-yl)acetaldehyde (68)

Into a stirring solution of oxalyl chloride (0.094 mL, 1.1 mmol) in CH$_2$Cl$_2$ (7 mL) at −78° C. was added DMSO (0.141 mL, 1.99 mmol). The reaction mixture was stirred for 0.5 h, followed by addition of compound 67 (0.25 g, 0.55 mmol, in 5 mL of CH$_2$Cl$_2$. The reaction mixture was stirred at the same temperature for 0.5 h, followed by addition of Et$_3$N (0.615 mL, 4.4 mmol), and stirring was continued for 1.5 h while allowing the reaction mixture to reach room temperature. The reaction mixture was quenched by addition of a saturated solution of NaHCO$_3$ and extracted with CH$_2$Cl$_2$ (3×100 mL). The combined organic layer was dried using Na$_2$SO$_4$, and the solvent was removed under reduced pressure. The crude product was purified by silica gel column chromatography (EtOAc/MeOH, 20:1) to give compound 68 (0.24 g, 99%). $^1$H NMR (600 MHz, CDCl$_3$): δ 9.71 (d, J=1.2 Hz, 1H), 7.19 (d, J=9.0 Hz, 2H), 7.01 (d, J=2.4 Hz, 1H), 6.81 (dd, J$_1$=6.6 Hz, J$_2$=1.8 Hz, 2H), 6.77 (dd, J$_1$=8.4 Hz, J$_2$=2.4 Hz, 1H), 6.55 (d, J=8.4 Hz, 1H), 4.71 (s, 2H), 4.63-4.61 (m, 2H), 4.33-4.31 (m, 2H), 3.75 (s, 3H), 3.22 (d, J=1.2 Hz, 2H), 3.13 (t, J=4.8 Hz, 4H), 2.65 (t, J=4.8 Hz, 4H).

5'-(4-(2-((2-amino-4,5,6,7-tetrahydrobenzo[d]thiazol-6-yl)(propyl)amino)ethyl) piperazin-1-yl)-1'-(4-methoxybenzyl)spiro[[1,3]dioxolane-2,3'-indolin]-2'-one (69)

Into a stirring solution of Pramipexole (0.112 g, 5.3 mmol) in CH$_2$Cl$_2$ (50 mL) was added aldehyde 68 (0.24 g, 5.3 mmol). After the mixture was stirred for 1 h, NaBH(OAc)$_3$ (0.23 g, 1.1 mmol) was added portion wise and the mixture was stirred for 48 h at room temperature. The reaction mixture was quenched with a saturated solution of NaHCO$_3$ at 0° C. and extracted with dichloromethane (3×100 mL). The combined organic layer was dried over Na$_2$SO$_4$, and the solvent was removed under reduced pressure. Crude product was purified by column chromatography (EtOAc/MeOH, 20:1) to give compound 69 (0.234 g, 66%). $^1$H NMR (400 MHz, CDCl$_3$): δ 7.20 (d, J=8.4 Hz, 2H), 7.01 (d, J=2.4 Hz, 1H), 6.82 (d, J=8 Hz, 2H), 6.76 (dd, J$_1$=8 Hz, J$_2$=2.4 Hz, 1H), 6.55 (d, J=8.0 Hz, 1H), 4.81 (bs, —NH$_2$, 2H), 4.71 (s, 2H), 4.62 (t, J$_1$=6.4 Hz, 2H), 4.32 (t, J$_1$=6.8 Hz, 2H), 3.75 (s, 3H), 3.08-3.06 (m, 5H), 2.69-2.44 (m, 14H), 1.99-1.96 (m, 1H), 1.72-1.68 (m, 1H), 1.48-1.43 (m, 2H), 0.87 (t, J=7.2 Hz, 3H); $^{13}$C NMR (100 MHz, CDCl$_3$): δ 173.2, 165.5, 159.0, 148.2, 144.9, 136.6, 128.5, 127.4, 124.6, 119.0, 117.3, 114.2, 114.1, 110.1, 102.6, 65.8, 58.5, 58.0, 55.2, 53.6, 53.5, 49.9, 48.3, 42.9, 26.5, 25.7, 25.0, 22.2, 11.8.

(S)-5-(4-(4-(2-((2-amino-4,5,6,7-tetrahydrobenzo[d]thiazol-6-yl)(propyl)amino)ethyl) piperazin-1-yl)phenyl)indoline-2,3-dione (70)

To a solution of 69 (0.05 g, 0.079 mmol) in 1:1 mixture of Conc. HCl and methanol (6 mL) was taken in a sealed tube. After that, the mixture was heated to 110° C. for 12 h. The reaction mixture was quenched with a saturated solution of NaHCO$_3$ at 0° C. and extracted with dichloromethane (3×100 mL). The combined organic layer was dried over Na$_2$SO$_4$, and the solvent was removed under reduced pressure. Crude product was purified by column chromatography (CH$_2$Cl$_2$/MeOH, 20:1) to give compound 70 (0.03 g, 69%). The pure amine was dissolved in 20:1 mixture of CH$_2$Cl$_2$:MeOH (0.5 mL), then added 2 M HCl (5 mL) at room temperature and stirred for 10 min. Evaporate the solvent using N$_2$ and then wash with ether followed by vaccume dry to form HCl salt of 70. Free amine: $^1$H NMR (400 MHz, CDCl$_3$): δ 8.56 (s, —NH, 1H), 7.16-7.12 (m, 2H), 6.80 (d, J=8.8 Hz, 1H), 4.99 (bs, —NH$_2$, 2H), 3.13-3.10 (m, 4H), 3.04-3.01 (m, 1H), 2.72-2.44 (m, 14H), 1.99-1.96 (m, 1H), 1.73-1.69 (m, 1H), 1.49-1.43 (m, 2H), 0.88 (t, J=7.2 Hz, 3H); $^{13}$C NMR (100 MHz, CDCl$_3$): δ 183.7, 165.9, 148.5, 144.7, 142.5, 135.4, 126.6, 118.5, 117.1, 113.0, 112.7, 58.5, 58.0, 53.46, 49.6, 48.3, 41.3, 29.6, 26.4, 25.8, 25.0, 22.3, 11.8. LRMS (ESI) m/z [M+H]$^+$: calcd. for C$_{24}$H$_{33}$N$_6$O$_2$S: 469.2386, found: 469.4826. The product was converted into corresponding hydrochloride salt. Mp: 312-314° C.; Anal. (C$_{24}$H$_{32}$N$_6$O$_2$S.4HCl.2H$_2$O.

The following table provides inhibition constants for displacing [3H]spiperone binding to the cloned D$_{2L}$ and D$_3$ receptors expressed in HEK cells. Results are means±SEM for 3 experiments each performed in triplicate. NR=Not repeated.

TABLE 2

Inhibition constants

| Compound | $K_i$, (nM), D2L [$^3$H]Spiperone | $K_i$, (nM), D3 [$^3$H]Spiperone |
|---|---|---|
| 22 (D-547) | 2,404 ± 29 | 15.8 ± 2.0 |
| 23 (D-548) | 175 ± 8 | 3.62 (4) ± 0.78 |
| (−)-23 (D-591) | 68.3 ± 12.0 | 1.57 ± 0.41 |
| 34 (D-575) | 116 ± 8 | 2.59 ± 0.31 |
| (−)-34 (D-593) | 65.7 ± 11.7 | 1.42 ± 0.14 |
| 35 (D-584) | 117 ± 17 | 1.01 ± 0.28 |
| (−)-36 (D-601) | 112 ± 8 | 0.78 ± 0.2 |
| 39 (D-567) | 233 ± 8 | 23.3 ± 4.0 |
| 46, 47 (D-592) | 121 ± 21 | 25.0 ± 1.96 |
| 54 (D-573) | 499 ± 16 | 11.9 ± 1.9 |
| 63 (D-570) | 4,634 ± 325 | 39.1 ± 5.4 |
| 70 (D-588) | 162 ± 7 | 14.2 ± 3.8 |

Compounds Having Carbazole Functionality

Figure 26:
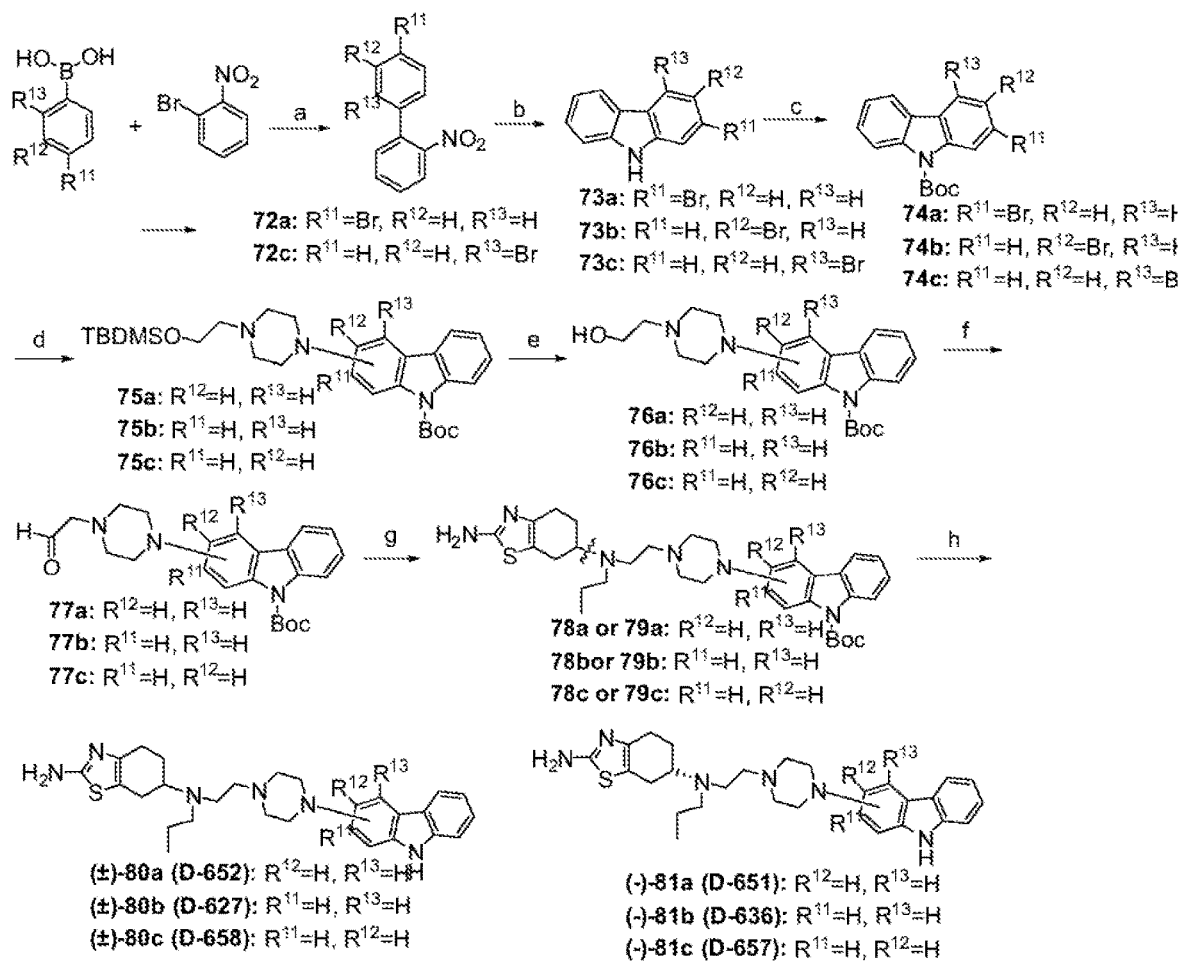
FIG. 26 provides a synthetic scheme for compounds having formula I.
Figure 27:
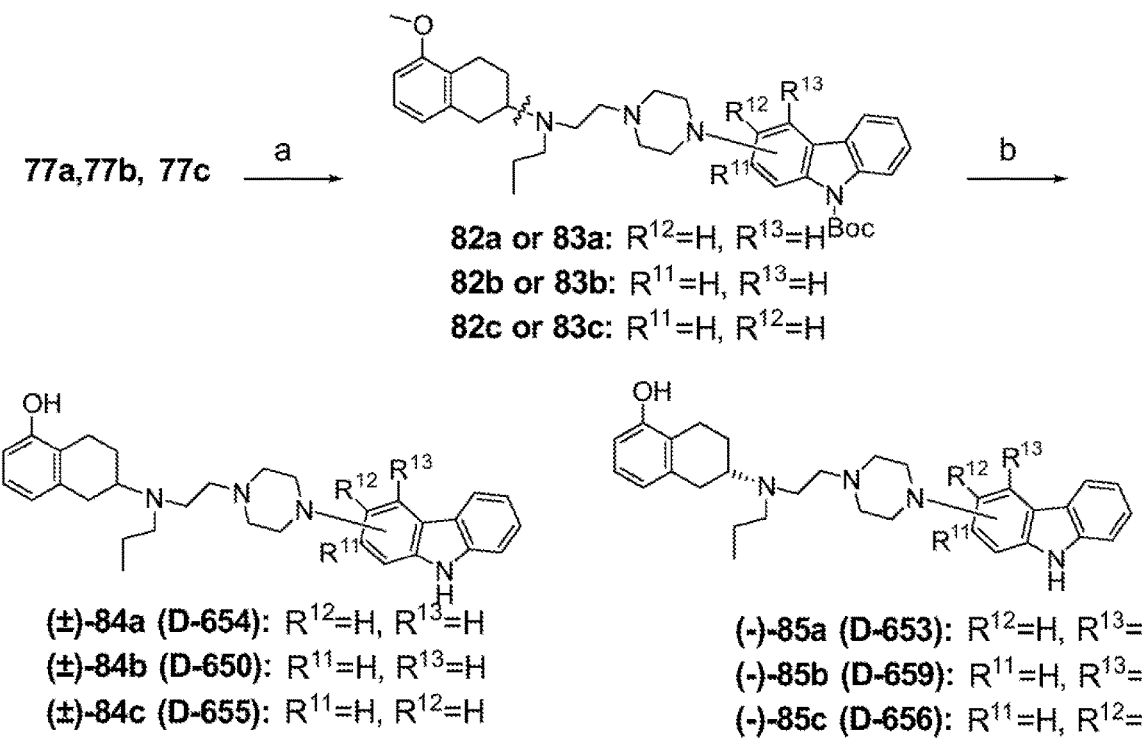
FIG. 27 provides a synthetic scheme for compounds having formula I.
Figure 28:
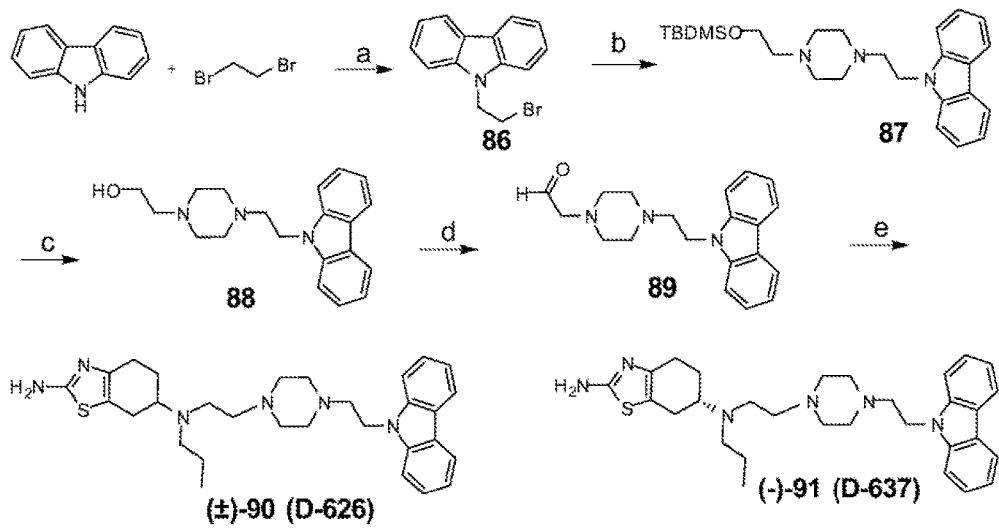
FIG. 28 provides a synthetic scheme for compounds having formula I.
Figure 29:
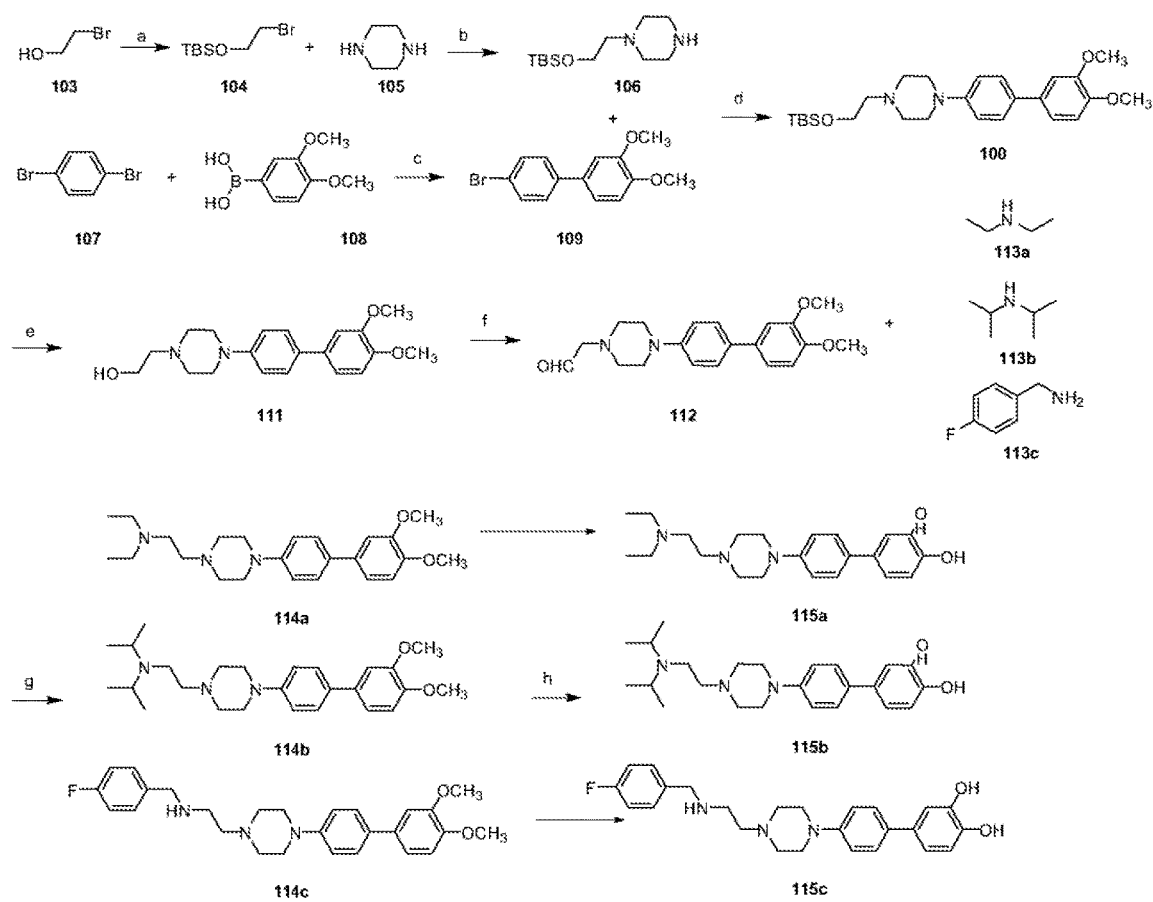
FIG. 29 provides a synthetic scheme for compounds having formula I.

A series of compounds were synthesized by incorporating the aminotetralin or bioisosteric equivalent agonist head group with carbazole functionality via ethylpiperazine linker (schemes of FIGS. 26, 27, 28). The scheme of FIG. 26 describes the syntheses of final compounds (±)-80a, (±)-80b, (±)-80c and (−)-81a, (−)-81b, (−)-81c. A palladium catalyzed coupling of (4-bromophenyl)boronic acid and 1-bromo-2-nitrobenzene afforded 4'-bromo-2-nitro-1,1'-biphenyl (82a). This compound was then cyclized in the presence of PPh$_3$ to produce 2-bromo-9H-carbazole (83a) which then underwent N-protection using di-tert-butyl dicarbonate in the presence of 4-dimethylaminopyridine (4-DMAP) to yield 84a. Palladium-catalyzed mediated cross coupling of 84a with 1-(2-((tert-butyldimethylsilyl)oxy)-ethyl)piperazine under refluxing conditions in the presence of Cs$_2$CO$_3$ and BINAP in toluene produced intermediate 85a. Treatment with n-Bu$_4$NF (TBAF) in THF removed the silyl protecting group of compound 85a to produce the alcohol 86a, which in the presence of pyridine-sulfur trioxide was oxidized to yield the corresponding aldehyde 87a. Reductive amination of the aldehyde with either (±) or (−)-pramipexole in the presence of NaBH(OAc)$_3$ afforded compounds 88a and 89a, respectively. In the final step, the amine protecting t-Boc groups were removed by treatment with trifluoroacetic acid to produce the final compounds (±)-90a and (−)-91a as TFA salts. The other final compounds (±)-90b, (±)-90c, (−)-91b and (−)-91c were also synthesized in the similar fashion as described above, where 3-Bromo-9H-carbazole and 4-Bromo-9H-carbazole were used as the starting materials, respectively.

The syntheses of the final compounds (±)-94a, (±)-94b, (±)-94c and (−)-95a, (−)-95b, (−)-95c is shown in the scheme of FIG. 27. To prepare these compounds, we employed (I) and (±)-(5-methoxy-1,2,3,4-tetrahydro-naphthalen-2-yl)-propyl-amine and reductively alkylated with intermediate aldehydes 7a-7c in the presence of NaBH(OAc)$_3$ to produce compounds (±)-92a, (±)-92b, (±)-92c, (−)-93a, (−)-93b, and (−)-93c. Finally, demethylation and removal of the protecting t-Boc groups were carried out in one step by refluxing with aq. HBr to give the final compounds (±)-94a, (±)-94b, (±)-94c, (−)-95a, (−)-95b, and (−)-95c as HBr salts.

The syntheses of two more target compounds (±)-100 and (−)-101 are illustrated in the scheme of FIG. 28. N-alkylation was first performed by refluxing carbazole with dibromoethane in presence of a mixture of K$_2$CO$_3$, KOH and TBAB to afford 9-(2-bromoethyl)-9H-carbazole 96. Base-catalyzed condensation of 1-(2-((tert-butyldimethylsilyl)oxy)ethyl)piperazine with intermediate 96 yielded compound 97, which on TBDMS deprotection in the presence of TBAF in THF afforded alcohol 98 in excellent yield. Pyridine-sulfur trioxide was used to oxidize alcohol 98 next to yield the corresponding aldehyde 99, which was then underwent reductive amination with either (±) or (−)-pramipexole in the presence of NaBH(OAc)$_3$ to produce the final compounds (±)-100 and (−)-101. These two molecules were converted to their corresponding HCl salts by treatment with ethereal HCl. All the final compounds were characterized by $^1$H and $^{13}$C NMR as well as elemental analysis.

A well established radioligand competition assay was carried out to evaluate binding affinity of the test compounds and were compared with that of the reference agent (S)-5-OH-DPAT (Table 3). Binding affinity to rat DA D$_2$ and D$_3$ receptors expressed in HEK-293 cells was determined as described by us previously. Table 3 lists the binding data of new compounds. Compounds (±)-90a-c, which incorporate racemic 2-aminothiazole head group and a piperazine ring connected to the different positions of the carbazole ring, exhibited high affinity for D$_3$ and low to moderate affinity for D$_2$ receptors. When the positions of attachment are at carbon 2 and 3 of the carbazole moiety for compounds 90a and 90b, respectively, both the compounds displayed low affinity for D$_2$ and high affinity for the D$_3$ receptors with high selectivity (K$_i$, D$_2$=902 nM, D$_3$=6.18 nM, D$_2$/D$_3$=146 and D$_2$=612 nM, D$_3$=3.12 nM, D$_2$/D$_3$=196 for 90a and 90b, respectively). Interestingly, covalent attachment at position 4 of the carbazole ring dramatically improved the affinity for D$_2$ while that for D$_3$ receptor remained the same (K$_i$, D$_2$=76.9 nM, D$_3$=7.8 nM, D$_2$/D$_3$=9.86 for 90c). This indicated highest tolerance of the 4-substituted carbazole derivative for interaction with the D2 and D3 receptors. As expected, we observed a 2-4-fold improvement in binding affinity when enantiomerically pure aminothiazole moiety was attached to the carbazole as in (−)-91a and (−)-91b compared to their racemic counterparts (K$_i$, D$_2$=504 nM, D$_3$=3.94 nM, D$_2$/D$_3$=128 and D$_2$=135 nM, D$_3$=3.80 nM, D$_2$/D$_3$=35 for (−)-91a and (−)-91b respectively). However, for (−)-91c we did not observe much difference from its racemic version.

Next, the effect of bioisosteric replacement of the aminothiazole moiety with aminotetraline functionality on the receptor binding of target compounds was evaluated. In corroboration with our previous results, aminotetraline substituted compounds (±)-94a-c and (−)-95a-c exhibited high affinity at both D$_2$ and D$_3$ receptors. For instance, the aminotetraline analogue (−)-95a has been found to have very high affinity for D$_2$ while displaying subnanomolar affinity for D$_3$ receptor compared to the corresponding thiazolidium counterpart (−)-91a (K$_i$, D$_2$=71.2 nM, D$_3$=0.40 nM, D$_2$/D$_3$=177 for (−)-95a vs D$_2$=504 nM, D$_3$=3.94 nM, D$_2$/D$_3$=128 for (−)-91a). Among the three enantiomerically pure isomers (−)-95a-c, which differ only in the substitution positions at the carbazole moiety, positions 2, 3 and 4, showed variable binding affinity at both D$_2$ and D$_3$ receptors (K$_i$, D$_2$=71.2 nM, D$_3$=0.40 nM for (−)-95a (D$_2$=61.6 nM, D$_3$=1.94 nM for (−)-95b and D$_2$=16.9 nM, D$_3$=0.36 nM for (−)-95c). As discussed before, substitution at the 4-position of the carbazole aromatic ring resulted in compounds 90c, (−)-91c, 94c and (−)-95c with better D$_2$/D$_3$ binding affinities in comparison to other isomeric analogues with compound (−)-95c exhibiting the highest affinity among all the molecules, underscoring the importance of positional attachment to the carbazole ring. Finally, the binding affinities were evaluated for another series of compounds in which the piperazine ring of the agonist fragment was appended directly to the carbazole nitrogen atom through a methylene linker. As shown in Table 3, enantiomeric compound (−)-101 displayed relatively higher binding affinity at $D_2$ and comparable affinity at $D_3$ receptor with moderate selectivity compared to the racemic compound (±)-100 ($K_i$, $D_2$=435 nM, $D_3$=6.60 nM, $D_2/D_3$=65.9 and $D_2$=82.6 nM, $D_3$=7.18 nM, $D_2/D_3$=12 for 100 and (−)-101, respectively). This structural modification suggests no significant differences in DA receptor interaction between compounds where the carbazole moiety is attached either at the ⅔ positions of the aromatic ring or through the nitrogen atom; however, a prominent difference exists for compounds where the carbazole nitrogen is sterically free to probably participate in additional receptor interaction (e.g. (−)-95c vs (−)-95b and (−)-101).

Based on binding data, functional activities of the selected optically active lead compounds for human DA $D_2$ and $D_3$ receptors expressed in CHO cells were measured by using [$^{35}$S]GTPγS binding assay. Agonist or partial agonist activity was judged by comparing with the maximum stimulation ($E_{max}$), produced by the full agonist DA. As shown in Table 4, aminothiazole containing compounds (−)-91b and (−)-91c demonstrated moderate potency at both $D_2$ and $D_3$ receptors ($EC_{50}$ (GTPγS); $D_2$=48.7, $D_3$=0.96 nM and $D_2$=22.2, $D_3$=1.67 nM, respectively), correlating well with binding data. While (−)-91b showed full agonist activity at both $D_2$ and $D_3$ receptors ($E_{max}$=87-93%), compound (−)-91c revealed partial agonist activity at $D_2$ and full agonism at $D_3$ receptor ($E_{max}$=57% vs 82%, respectively for $D_2$ and $D_3$). On the other hand, aminotetraline compound (−)-95a displayed very high functional potency ($EC_{50}$ (GTPγS); $D_2$=0.87 and $D_3$=0.23 nM) and full agonism ($E_{max}$=85-92%) at both the receptors. Compound (−)-95c was also found to be highly potent and efficacious in stimulating both receptors ($EC_{50}$ (GTPγS); $D_2$=2.29 and $D_3$=0.22 nM; $E_{max}$=74-88%). Neither compounds exhibited appreciable selectivity for $D_3$ over $D_2$ (Table 4) and their selectivity for $D_3$ receptor was much less when compared to the binding data (Table 3). The values for the ClogP and tPSA for all the compounds were calculated as shown in Table 3. In general, these values predict that these compounds should cross the blood brain barrier to produce in vivo CNS efficacy which we observed in case of (−)-91b, (−)-95a and (−)-95c (see below). Therefore, our SAR results of a series of carbazole compounds show that the affinity and selectivity for the $D_2/D_3$ receptors are governed by the nature of covalent attachment to the carbazole moiety and the structure of agonist binding head group in the hybrid molecule.

Figure 2:
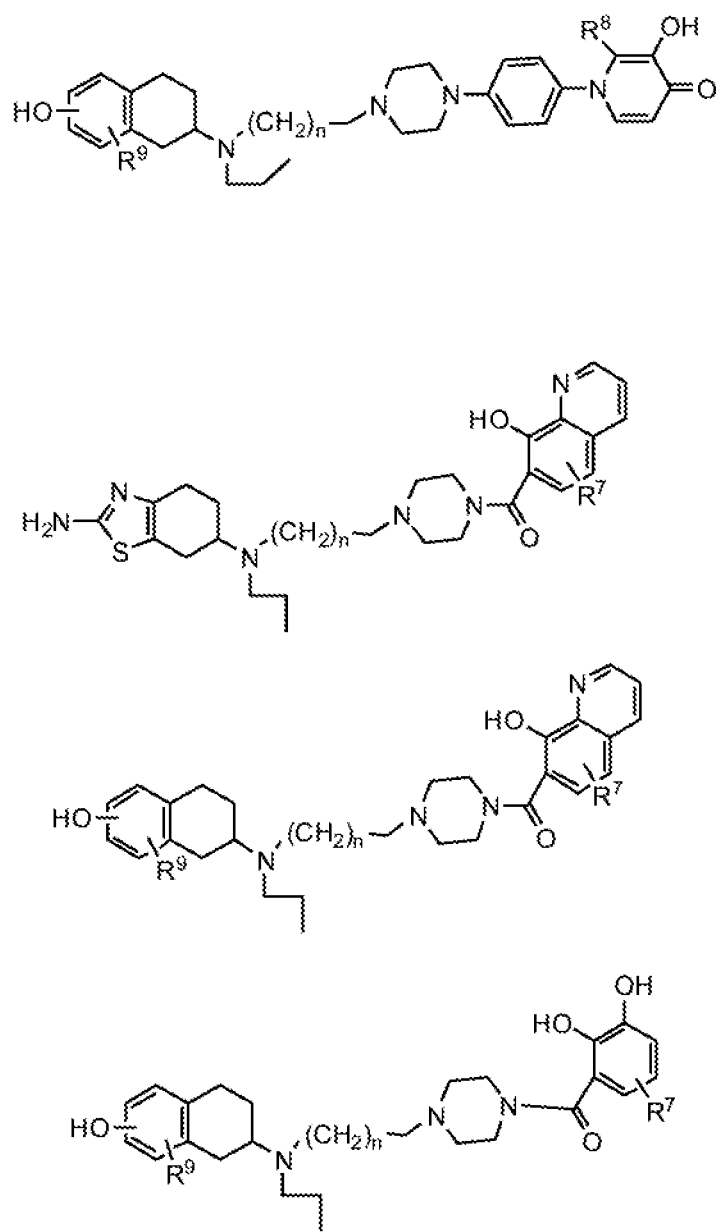

In vivo evaluation of the compounds (−)-91b, (−)-95a and (−)-95c in a reserpine-based PD animal model was performed next. In this model depletion of catecholamines by reserpine results in catalepsy in rats. This is a well-established animal model for PD. Reserpine produced a significant inhibition of locomotion in rats 18 h after the administration of the drug (5 mg/kg, sc), which indicated the development of akinesia (FIG. 2). Compounds (−)-91b, (−)-95a and (−)-95c at the dose of 10 μMol/kg, ip, significantly reversed akinesia in rats compared to reserpine treatment alone. The compounds also demonstrated significant enhancement of locomotion for the duration of the study of 6 h. Among the molecules tested, (−)-95a was found to have the highest in vivo activity and this finding correlates with in vitro functional assay where the compound exhibited subnanomolar potency for stimulation of $D_2/D_3$ receptors along with full agonist property. On the other hand, the reference drug ropinirole at 10 μMol/kg, ip, produced a fast onset of activation of locomotion compared to the control but had a shorter duration of action compared to the test compounds. It has been shown that the locomotor stimulation in this reserpine model is mediated by postsynaptic $D_2/D_3$ receptor activation by the compounds.

Antioxidant Activity

Figure 3:
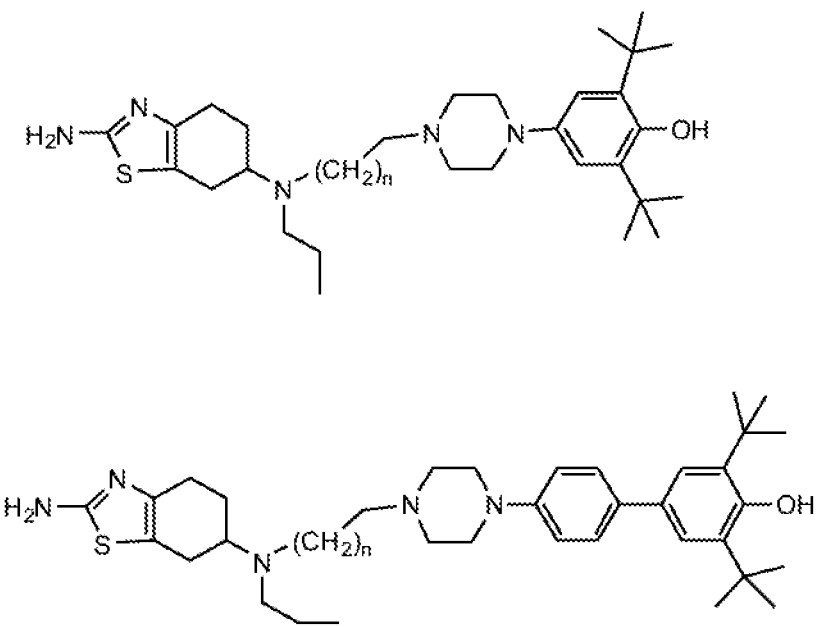
Figure 4:
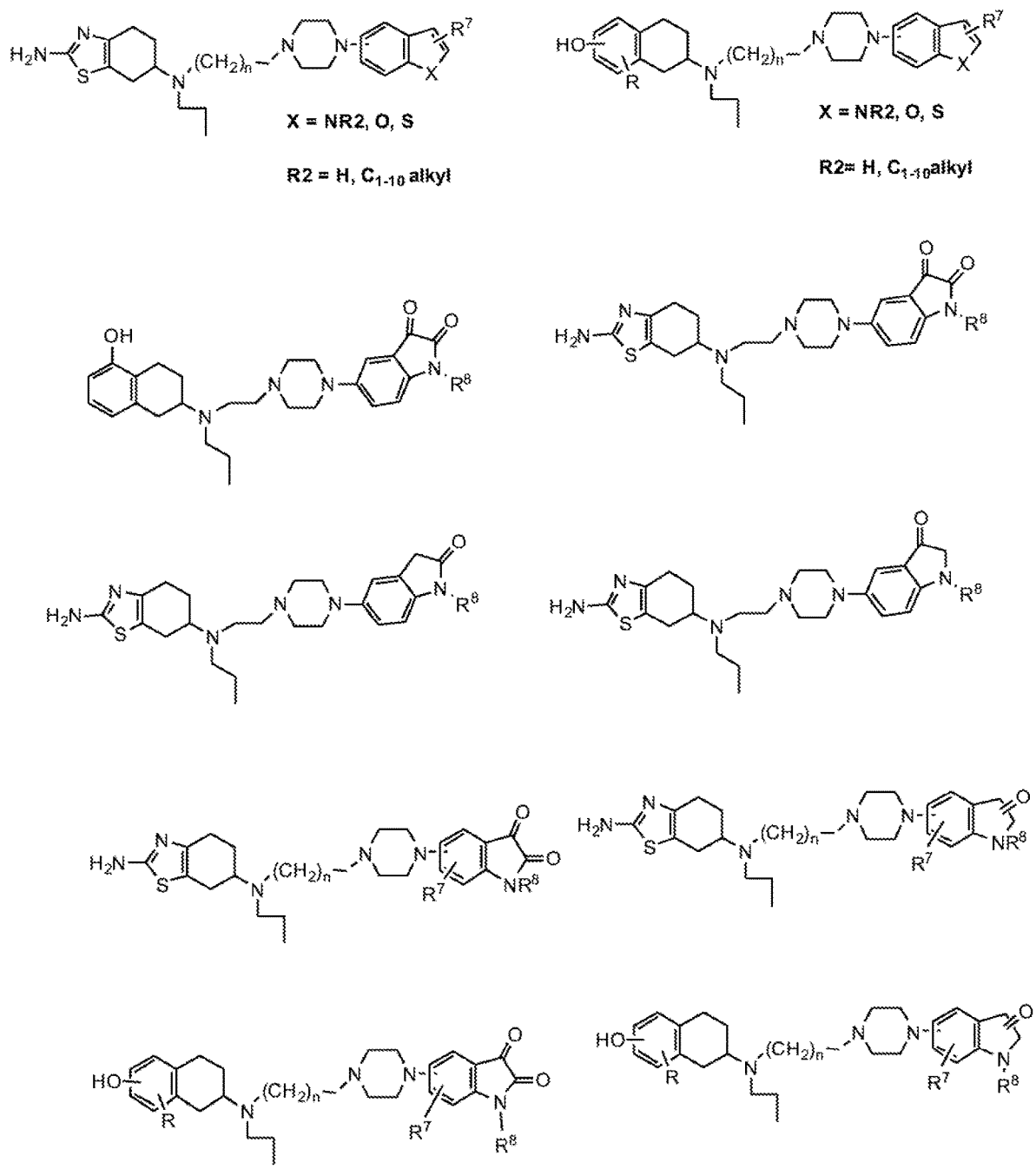
Figure 5:
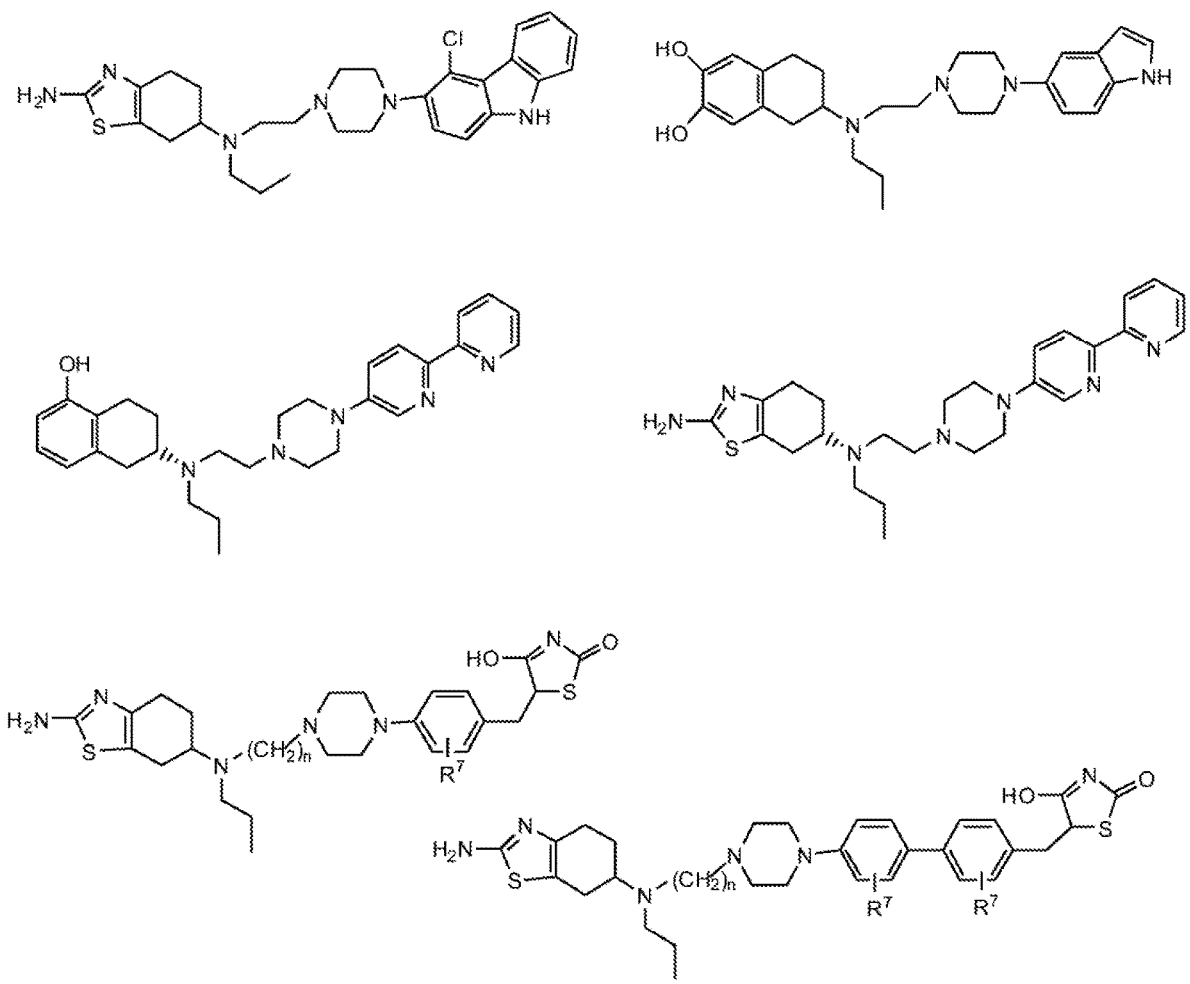
Figure 6:
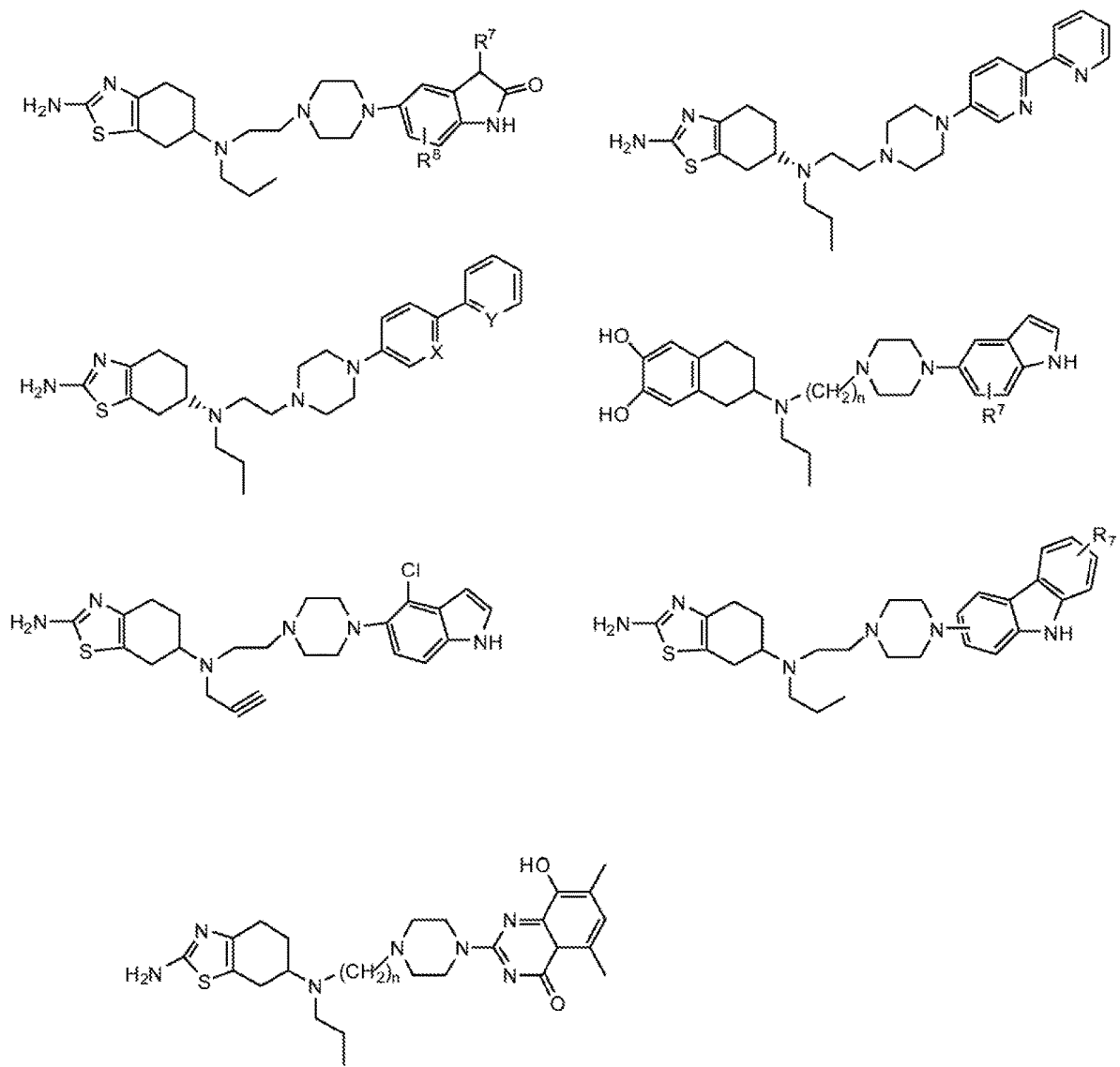
Figure 7:
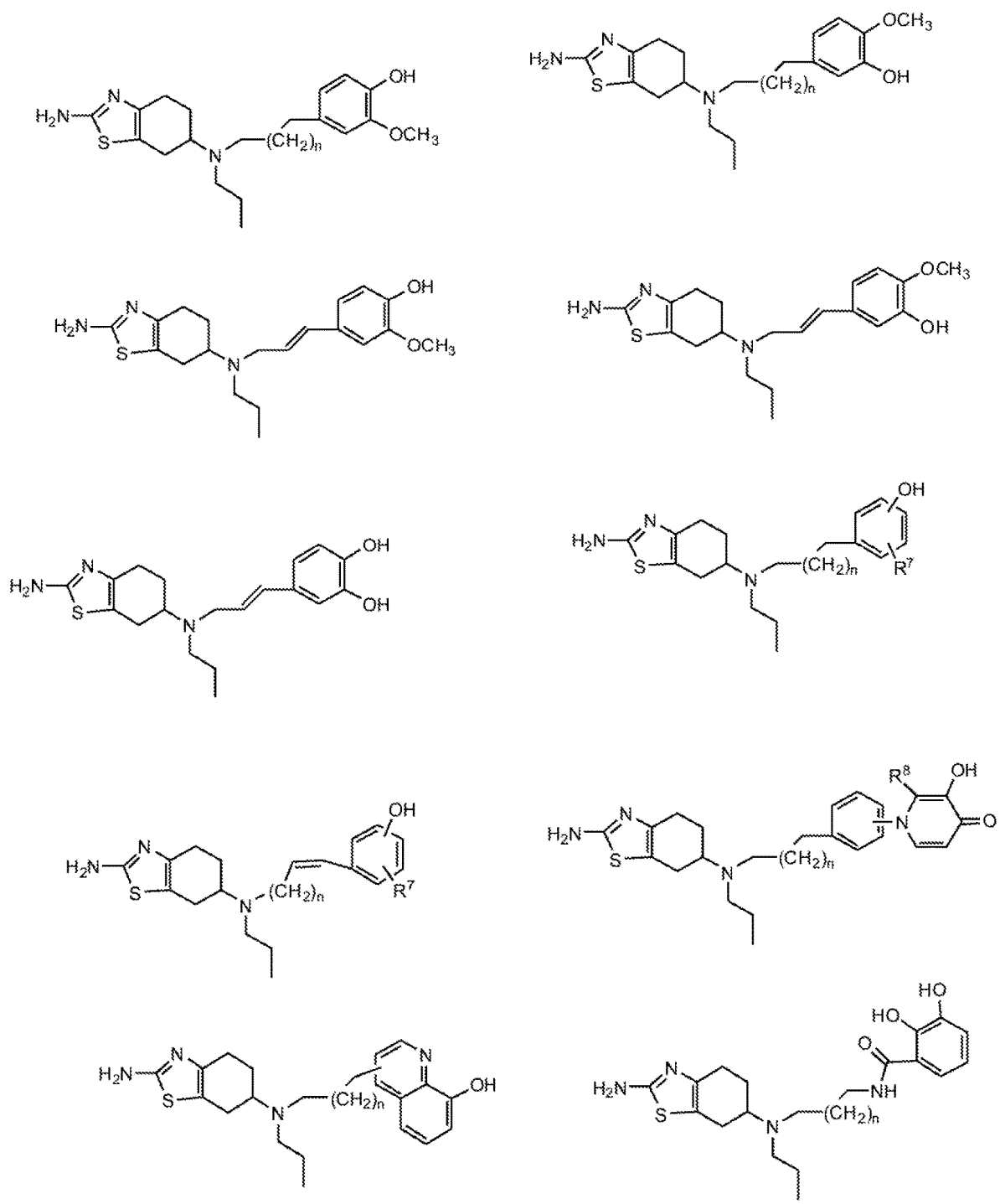
Figure 10:
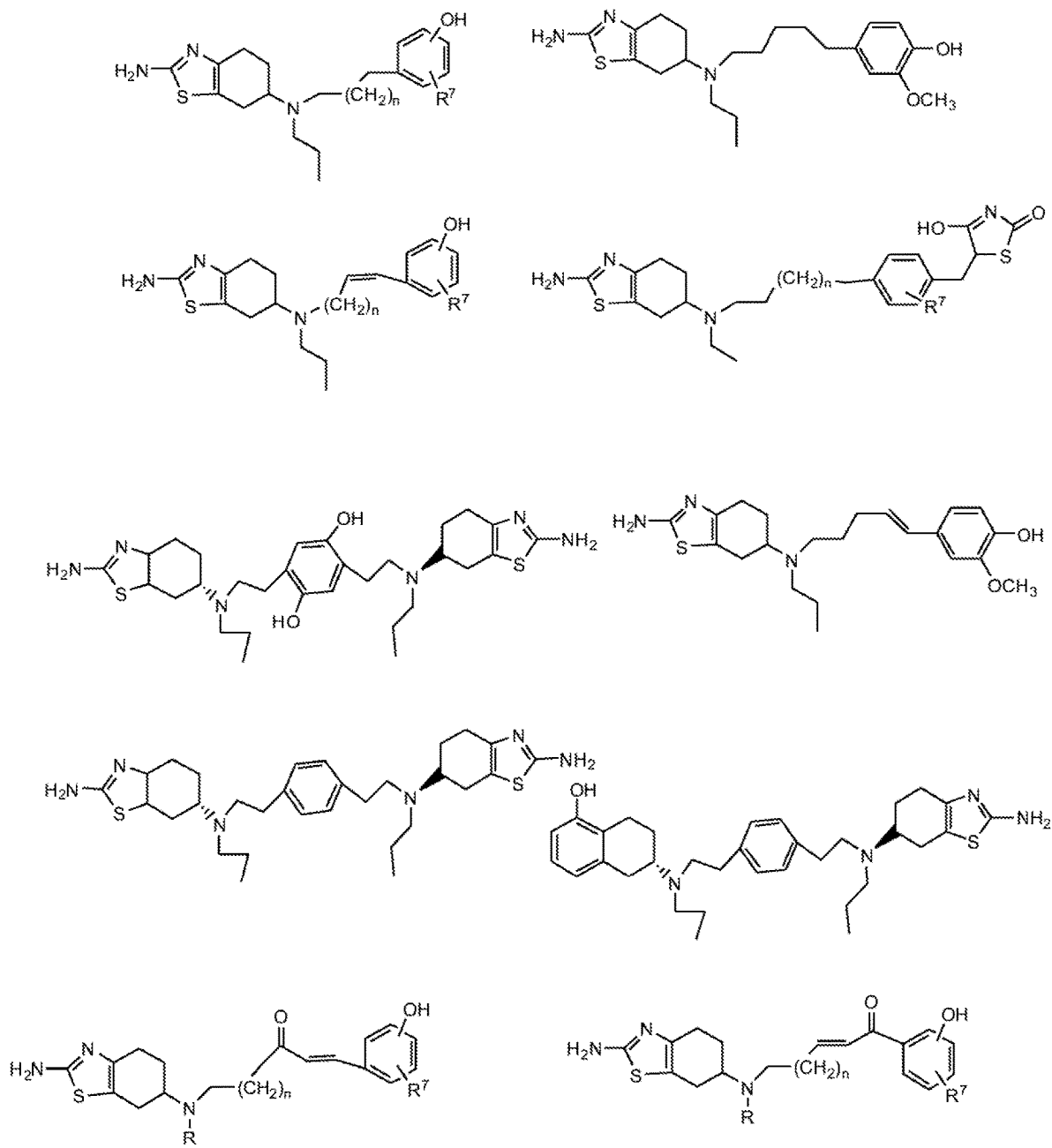

Experimental detection of reactive oxygen species (ROS) produced by 6-OHDA was carried out by DCFDA assay. 6-OHDA, a well known neurotoxin, produces oxidative stress similar to what is observed in PD and the mechanism of neurotoxicity of 6-OHDA takes place via its auto-oxidation and subsequent generation of hydrogen peroxide. DCFDA is a non-fluorogenic dye but in the presence of ROS, it is oxidized to produce DCF which produces florescence. We have previously shown that 6-OHDA causes cell death in a dose-dependent manner. We chose 75 μM 6-OHDA as we have shown that this dose induces 40-50% cell death. To examine whether our compounds (−)-91b, (−)-95a and (−)-95c can protect PC12 cells from the ROS produced by the exposure to 75 μM 6-OHDA, the PC12 cells were treated with 6-OHDA after pretreatment with various concentrations of drugs (5, 10, 20 μM) for 24 h, and compared with 6-OHDA alone treated cells. As shown in FIG. 3, a well over two-fold increase in ROS was observed in cells treated with 6-OHDA (75 μM) alone compared to the control untreated cells. However, the test compounds could dose dependently decrease the production of ROS induced by 6-OHDA (75 μM) in PC12 cells. In this regard, highest dose of all the three compounds was the most efficacious in producing significant antioxidant effect. Thus at 20 μM, a reduction in 76%, 93% and 36% ROS were induced by (−)-91b, (−)-95a and (−)-95c, respectively (FIG. 3A-C). Thus, (−)-95a was found to be the most potent antioxidant (FIG. 3B).

Cellular Neuroprotection Activity

To investigate the neuroprotection property of the selected target molecules (−)-91b, (−)-95a and (−)-95c against 6-OHDA-induced cytotoxicity, we used dopaminergic rat adrenal Pheochromocytoma PC12 cells. As reported above, treatment of PC12 cells with 6-OHDA at 75 μM for 24 h produced ~50% loss in cells viability and this concentration was used in subsequent experiments. In contrast, it was observed that the cells treated with increasing concentrations of either (−)-91b or (−)-95c alone (0.01-30 μM) showed no cells loss compared to untreated controls (FIGS. 4A and 4C, respectively), indicating no toxicity of the compounds at the doses tested. However, (−)-95a produced some incremental toxicity starting at 20 μM dose (FIG. 4B). The potential neuroprotective effects of (−)-91b, (−)-95a and (−)-95c against 6-OHDA-induced toxicity were evaluated next. Thus, pre-treatment of the cells with the test compounds for 24 h followed by exposure to 6-OHDA 75 μM for another 24 h produced dose-dependent protection of the cells from the neurotoxic insult and the greatest protective effect was observed at 5 μM for (−)-91b and 20 μM for (−)-95c. At those concentration both drugs increased cell survival by ~20% compared to 6-OHDA (75 μM) treated alone (FIGS. 4D and 4F), indicating neuroprotective effect of these drugs. Compound (−)-95a also revealed dose-dependent neuroprotection and the highest effect was observed at the dose of 10 μM (15%) but the effect was not observed at the higher doses (FIG. 4E). This could be due to the fact that the compound by itself produced toxicity to the cells at doses ≥20 μM and the presence of 6-OHDA enhanced the toxicity (FIG. 4B).

Effect of (−)-91b (D636) and (−)-95a (D653) on the Aggregation of α-syn with 0.5% Seeding The α-syn assay was carried out by following the procedures developed by us earlier. The compounds (−)-91b (D636) and (−)-95a (D653) were incubated with α-syn seeded with 0.5% PFFs for a period of 30D at 37° C. without agitation. Seeding of monomeric α-syn with 0.5% PFFs leads to a significant increase in aggregation characterized by a 15-fold increase in ThT fluorescence at 30D. Both (−)-91b and (−)-95a lead to a significant decrease in the ThT fluorescence (p<0.0001) when compared to α-syn seeded with 0.5% PFFs alone at 30D (FIG. 5A). (−)-91b and (−)-95a showed a 16 fold and 3 fold decrease in ThT fluorescence respectively, when compared to seeded α-syn at 30D.

When PC12 cells were treated with the aggregates formed by 0.5% PFFs seeding at 30D, it was observed that the viability went down to 37% when compared to control. However, the seeded samples formed in the presence of (−)-91b and (−)-95a showed significant less toxicity when compared to seeded α-syn without compounds. The viability values of PC12 cells when treated with α-syn seeded samples in the presence of (−)-91b and (−)-95a were 71% and 72% at 30D when compared to control (FIG. 5B). We have previously shown that the parent compounds to our hybrid molecules, Pramipexole and 5-OHDPAT were far less effective in decreasing ThT fluorescence and reducing toxicities when compared to our multifunctional hybrid agonist.

In conclusion, the present study represents the development of a novel series of carbazole-based multifunctional DA $D_2/D_3$ receptor agonists. Compounds (−)-91b, (−)-95a and (−)-95c exhibited high binding affinity and full agonist activity at the both $D_2$ and $D_3$ receptors. The lead molecules were highly efficacious in a PD animal model by reversing hypo-locomotion activity with a long duration of action, indicating their potential in relieving motor dysfunction in PD. In a cellular model, the lead compounds exhibited potent anti-oxidant activity produced by neurotoxin 6-OHDA. To gain further insight into their possible multifunctional property, the data presented here also demonstrates that all three compounds (−)-91b, (−)-95a and (−)-95c exhibited neuroprotective property in an in vitro cellular model of PD by protecting neuronal PC12 cells from neurotoxin 6-OHDA. Furthermore, in vitro assays with recombinant α-syn protein demonstrated potent modulatory effect of (−)-91b and (−)-95a on aggregation and toxicity of α-syn protein. In summary, we are able to demonstrate that multifunctional drugs like (−)-91b, (−)-95a and (−)-95c have the potential not only to alleviate motor dysfunction in PD patients, but also to modify disease progression. More in depth future studies to establish the disease-modifying effects of the compounds will shed more light into their potential therapeutic application.

Experimental Section

Reagents and solvents were obtained from commercial suppliers and used as received unless otherwise indicated. Dry solvent was obtained according to the standard procedure. All reactions were performed under $N_2$ atmosphere unless otherwise indicated. Analytical silica gel 60 F254-coated TLC plates were purchased from EMD Chemicals, Inc. and were visualized with UV light or by treatment with phosphomolybdic acid (PMA), or ninhydrin. Flash column chromatographic purification was done using Whatman Purasil 60A silica gel 230-400 mesh. Proton nuclear magnetic resonance ($^1$H NMR) spectra and carbon nuclear magnetic resonance ($^{13}$C NMR) spectra were measured on Varian 400 and 600 MHz NMR spectrometer with tetramethylsilane (TMS) as an internal standard. The NMR solvent used was either $CDCl_3$ or $CD_3OD$ unless otherwise indicated. Autopol III automatic polarimeter (Rudolph Research Analytical) was used to record the optical rotations. MEL-TEMP II (Laboratory Devices Inc., U.S.) capillary melting point apparatus was used to record the melting points. Purity of the compounds was determined by elemental analysis and was within ±0.4% of the theoretical value (≥95% purity). Elemental analyses were performed by Atlantic Microlab, Inc., GA, USA.

Procedure A. 4'-Bromo-2-nitro-1,1'-biphenyl (82a)

To a stirring solution of 1-bromo-2-nitrobenzene (2.0 g, 9.9 mmol) and (4-bromophenyl)boronic acid (2.19 g, 10.89 mmol) in THF (25 mL) were added $Pd(PPh_3)_4$ (0.572 g, 0.50 mmol) followed by 2M $K_2CO_3$ (5.53 g in 20 mL water) at room temperature. The reaction mixture was stirred at 90° C. for 12 h after which it was cooled and extracted with $CH_2Cl_2$. The combined organic layer was dried over $Na_2SO4$, filtered, and concentrated in vacuo. The crude material was purified by column chromatography over silica gel using hexane:ethyl acetate (9:1) as solvent to give compound 82a (2.7 g, 98%). $^1$H NMR (600 MHz, $CDCl_3$): δ 7.88 (d, J=8.4 Hz, 1H), 7.64-7.61 (m, 1H), 7.59-7.55 (m, 2H), 7.53-7.50 (m, 1H), 7.42-7.40 (m, 1H), 7.20-7.18 (m, 2H).

2-Bromo-2'-nitro-1, 1'-biphenyl (82c)

To a stirring solution of 1-bromo-2-nitrobenzene (2.50 g, 12.37 mmol) and (2-bromophenyl)boronic acid (2.73 g, 13.61 mmol) in THF (30 mL) were added $Pd(PPh_3)_4$ (0.715 g, 0.61 mmol) followed by 2M $K_2CO_3$ (5.53 g in 20 mL water) according to procedure A to give compound 82c (2.18 g, 94%). $^1$H NMR (600 MHz, $CDCl_3$): δ 7.87 (d, J=8.4 Hz, 1H), 7.44 (t, J=7.2 Hz, 1H), 7.40 (d, J=9 Hz, 1H), 7.30 (d, J=7.8 Hz, 1H), 7.14 (t, J=7.2 Hz, 1H), 7.10 (d, J=7.2 Hz, 1H), 7.03 (d, J=7.2 Hz, 2H).

Procedure B. 2-Bromo-9H-carbazole (83a)

Compound 82a and $PPh_3$ were dissolved in 1,2-dichlorobenzene and the resulting solution was stirred at 170° C. for 12 h after which it was cooled and extracted with $CH_2Cl_2/H_2O$. The combined organic layer was dried over $Na_2SO_4$, filtered, and concentrated in vacuo. The crude material was purified by column chromatography over silica gel using hexane:ethyl acetate (9:1) to yield compound 83a (1.57 g, 89%). $^1$H NMR (600 MHz, $CDCl_3$): δ 8.04 (d, J=8.4 Hz, 1H), 7.92 (d, J=8.4 Hz, 1H), 7.62-7.58 (m, 2H), 7.52-7.47 (m, 2H), 7.39 (d, J=8.4 Hz, 1H).

4-Bromo-9H-carbazole (83c)

Compound 82c and $PPh_3$ were reacted in 1,2-dichlorobenzene according to procedure B to yield compound 83c (1.25 g, 87%). $^1$H NMR (600 MHz, $CDCl_3$): δ 8.81 (d, J=7.8 Hz, 1H), 7.97 (s, 1H), 7.50 (t, J=7.2 Hz, 1H), 7.44 (d, J=7.2 Hz, 1H), 7.35 (t, J=7.8 Hz, 1H), 7.30 (d, J=7.8 Hz, 1H), 7.25-7.20 (m, 1H).

Procedure C. tert-Butyl 2-bromo-9H-carbazole-9-carboxylate (84a)

To a stirring solution of compound 83a (1.5 g, 6.09 mmol) in THF (20 mL) were added $(Boc)_2O$ (1.46 g, 6.7 mmol) and DMAP (0.819 g, 6.7 mmol) in THF (20 mL) at room temperature. The reaction mixture was stirred at the same temperature for 12 h. The crude mixture was evaporated under reduced pressure, followed by extraction with EtOAc (3×20 mL) in water. The combined organic layer was dried over Na$_2$SO$_4$, filtered, and concentrated in vacuo. The crude material was purified by silica gel column chromatography (hexane:EtOAc=19:1) to yield compound 84a (1.78 g, 84%). $^1$H NMR (600 MHz, CDCl$_3$): δ 8.48 (d, J=8.4 Hz, 1H), 8.07 (d, J=8.4 Hz, 1H), 7.24 (t, J=7.8 Hz, 1H), 7.18 (d, J=7.8 Hz, 1H), 7.11 (t, J=7.2 Hz, 1H), 6.97 (t, J=8.10 Hz, 1H), 1.53 (s, 9H).

tert-Butyl 3-bromo-9H-carbazole-9-carboxylate (84b)

Commercially available 3-Bromo-9H-carbazole (83b) (2.0 g, 8.13 mmol) was reacted with (Boc)$_2$O (1.95 g, 8.94 mmol) and DMAP (1.09 g, 8.94 mmol) in THF (20 mL) according to procedure C. The crude material was purified by column chromatography over silica gel using hexane: ethyl acetate (19:1) as solvent to give compound 84b (2.8 g, ~100%). $^1$H NMR (600 MHz, CDCl$_3$): δ 8.27 (d, J=8.4 Hz, 1H), 8.19 (d, J=8.4 Hz, 1H), 8.08 (d, J=2.4 Hz, 1H), 7.92 (qd, J=7.8, 0.6 Hz, 1H), 7.55 (dd, J=6.6, 2.4 Hz, 1H), 7.49 (td, J=8.4, 1.2 Hz, 1H), 7.36 (td, J=8.4, 1.2 Hz, 1H), 1.76 (s, 9H).

tert-Butyl 4-bromo-9H-carbazole-9-carboxylate (84c)

Compound 83c (1.5 g, 6.09 mmol) was reacted with (Boc)$_2$O (1.46 g, 6.7 mmol) and DMAP (0.819 g, 6.7 mmol) in THF (20 mL) according to procedure C. The crude material was purified by silica gel column chromatography (hexane:EtOAc=19:1) to yield compound 84c (1.78 g, 84%). $^1$H NMR (600 MHz, CDCl$_3$): δ 8.53 (s, 1H), 8.26 (d, J=8.4 Hz, 1H), 7.94 (d, J=7.8 Hz, 1H), 7.82 (d, J=8.4 Hz, 1H), 7.49-7.46 (m, 2H), 7.36 (t, J=7.2 Hz, 1H), 1.77 (s, 9H).

Procedure D. tert-Butyl 2-(4-(2-((tert-butyldimethylsilyl)oxy)ethyl)piperazin-1-yl)-9H-carbazole-9-carboxylate (85a)

To a mixture of compounds 84a (0.8 g, 2.31 mmol), 1-(2-((tert-butyldimethylsilyl)oxy)-ethyl)piperazine (1.13 g, 4.62 mmol), BINAP (0.144 g, 0.23 mmol) and Cs$_2$CO$_3$ (2.26 g, 6.93 mmol), toluene (15 mL) was added under N$_2$ atmosphere. The reaction mixture was degassed by bubbling N$_2$ for 5 min and then Pd(OAc)$_2$ (0.039 g, 0.17 mmol) was added quickly. The system was degassed again and refluxed for 24 h under inert condition. The reaction mixture was cooled to room temperature, filtered through a pad of celite, washed with dichloromethane and concentrated in vacuum. The crude residue was purified by column chromatography (hexane:EtOAc=4:1) to afford compound 85a (0.97 g, 82%). $^1$H NMR (600 MHz, CDCl$_3$): δ 8.23 (d, J=7.8 Hz, 1H), 7.92 (s, 1H), 7.84 (d, J=7.2 Hz, 1H), 7.81 (d, J=9.0 Hz, 1H), 7.35 (t, J=7.2 Hz, 1H), 7.29 (t, J=7.2 Hz, 1H), 7.00 (dd, J=9.0, 1.8 Hz, 1H), 3.82 (t, J=6.6 Hz, 2H), 3.32 (t, J=4.8 Hz, 4H), 2.74 (t, J=4.8 Hz, 4H), 2.62 (t, J=6.6 Hz, 2H), 1.75 (s, 9H), 0.91 (s, 9H), 0.09 (s, 6H).

tert-Butyl 3-(4-(2-((tert-butyldimethylsilyl)oxy)ethyl)piperazin-1-yl)-9H-carbazole-9-carboxylate (85b)

A mixture of compound 84b (1.2 g, 3.47 mmol), 1-(2-((tert-butyldimethylsilyl)oxy)ethyl)piperazine (1.27 g, 5.20 mmol), Pd(OAc)$_2$ (0.058 g, 0.26 mmol), BINAP (0.216 g, 0.35 mmol) and Cs$_2$CO$_3$ (3.39 g, 10.4 mmol) in toluene (25 mL) was heated at 110° C. for 24 h according to procedure D. The crude material was purified by silica gel column chromatography (hexane:EtOAc=4:1) to give compound 85b (1.4 g, 79%). $^1$H NMR (600 MHz, CDCl$_3$): δ 8.27 (d, J=8.4 Hz, 1H), 8.16 (d, J=8.4 Hz, 1H), 7.93 (d, J=7.8 Hz, 1H), 7.48 (d, J=2.4 Hz, 1H), 7.44 (t, J=7.8 Hz, 1H), 7.32 (t, J=7.8 Hz, 1H), 7.13 (dd, J=6.6, 2.4 Hz, 1H), 3.83 (t, J=6.6 Hz, 2H), 3.28 (t, J=4.8 Hz, 4H), 2.77 (t, J=4.8 Hz, 4H), 2.63 (t, J=6.6 Hz, 2H), 1.75 (s, 9H), 0.92 (s, 9H), 0.09 (s, 6H).

tert-Butyl 4-(4-(2-((tert-butyldimethylsilyl)oxy)ethyl)piperazin-1-yl)-9H-carbazole-9-carboxylate (85c)

A mixture of 84c (2.70 g, 7.80 mmol), 1-(2-((tert-butyldimethylsilyl)oxy)-ethyl)piperazine (3.24 g, 13.25 mmol), Pd(OAc)$_2$ (0.0.13 g, 0.59 mmol), BINAP (0.49 g, 0.78 mmol) and Cs$_2$CO$_3$ (7.62 g, 23.4 mmol) in toluene (30 mL) was heated at 110° C. for 24 h according to procedure D. The crude residue was purified by column chromatography (hexane:EtOAc=4:1) to afford compound 85c (3.24 g, 82%). $^1$H NMR (600 MHz, CDCl$_3$): δ 8.34 (dd, J=8.1, 4.8 Hz, 2H), 8.08 (d, J=8.4 Hz, 1H), 7.45 (t, J=7.2 Hz, 1H), 7.41-7.36 (m, 2H), 7.04 (d, J=8.4 Hz, 1H), 3.85 (t, J=6.6 Hz, 2H), 3.33 (d, J=5.4 Hz, 2H), 2.99 (t, J=5.4 Hz, 2H), 2.71 (t, J=6.6 Hz, 4H), 1.75 (s, 9H), 0.91 (s, 9H), 0.10 (s, 6H).

Procedure E. tert-Butyl 2-(4-(2-hydroxyethyl)piperazin-1-yl)-9H-carbazole-9-carboxylate (86a)

Into a stirring solution of compound 85a (0.95 g, 1.86 mmol) in THF (10 mL) was added n-tetrabutylammonium fluoride (2.8 mL, 2.8 mmol, 1.0 M solution in THF) at 0° C. The reaction mixture was then stirred at room temperature for 2 h. THF was evaporated in vacuo, and the residue was diluted with CH$_2$Cl$_2$ (25 mL) and washed with a saturated solution of NaHCO$_3$. The water layer was extracted with CH$_2$Cl$_2$ (3×50 mL). The combined organic layer was washed with brine, dried over Na$_2$SO$_4$, and evaporated under reduced pressure. The crude product was purified by silica gel column chromatography (EtOAc:MeOH=9:1) to give compound 86a (0.595 g, 81%). $^1$H NMR (600 MHz, CDCl$_3$): δ 8.23 (d, J=7.8 Hz, 1H), 7.94 (s, 1H), 7.85 (d, J=7.8 Hz, 1H), 7.82 (d, J=9.0 Hz, 1H), 7.36 (t, J=7.2 Hz, 1H), 7.30 (t, J=7.2 Hz, 1H), 7.00 (dd, J=6.6, 1.8 Hz, 1H), 3.68 (t, J=5.4 Hz, 2H), 3.34 (t, J=4.8 Hz, 4H), 2.73 (t, J=4.8 Hz, 4H), 2.64 (t, J=5.4 Hz, 2H), 1.76 (s, 9H).

tert-Butyl 3-(4-(2-hydroxyethyl)piperazin-1-yl)-9H-carbazole-9-carboxylate (6b)

Compound 85b (1.2 g, 2.35 mmol) in THF (15 mL) was reacted with n-tetrabutylammonium fluoride (4.71 mL, 4.71 mmol, 1.0 M solution in THF) according to procedure E. The crude product was purified by silica gel column chromatography (EtOAc:MeOH=9:1) to yield compound 86b (0.78 g, 84%). $^1$H NMR (600 MHz, CDCl$_3$): δ 8.28 (d, J=8.4 Hz, 1H), 8.18 (d, J=8.4 Hz, 1H), 7.93 (d, J=7.8 Hz, 1H), 7.49 (d, J=2.4 Hz, 1H), 7.44 (t, J=7.8 Hz, 1H), 7.33 (t, J=7.8 Hz, 1H), 7.13 (dd, J=6.6, 2.4 Hz, 1H), 3.69 (t, J=5.4 Hz, 2H), 3.29 (t, J=4.8 Hz, 4H), 2.76 (t, J=4.8 Hz, 4H), 2.66 (t, J=5.4 Hz, 2H), 1.75 (s, 9H).

tert-Butyl 4-(4-(2-hydroxyethyl)piperazin-1-yl)-9H-carbazole-9-carboxylate (86c)

Compound 85c (3.30 g, 6.47 mmol) was reacted with n-tetrabutylammonium fluoride (9.70 mL, 9.70 mmol, 1.0 M solution in THF) in THF (30 mL) according to procedure E. The crude product was purified by silica gel column chromatography (EtOAc:MeOH=9:1) to give compound 86c (2.01 g, 80%). $^1$H NMR (600 MHz, CDCl$_3$): δ 8.27 (d, J=6.6 Hz, 1H), 8.17 (d, J=7.8 Hz, 1H), 7.92 (d, J=7.8 Hz, 1H), 7.47 (s, 1H), 7.43 (t, J=7.2 Hz, 1H), 7.31 (t, J=7.2 Hz, 1H), 7.11 (d, J=9.0 Hz, 1H), 3.69 (t, J=5.4 Hz, 2H), 3.26 (s, 4H), 2.76 (s, 4H), 2.62 (t, J=5.4 Hz, 2H), 1.73 (s, 9H).

Procedure F. tert-Butyl 2-(4-(2-oxoethyl)piperazin-1-yl)-9H-carbazole-9-carboxylate (87a)

Into a stirring solution of compound 86a (0.30 g, 0.76 mmol) in CH$_2$Cl$_2$ (6 mL) and DMSO (3 mL), was added Et$_3$N (0.74 mL, 5.31 mmol) at 0° C. The reaction mixture was stirred for 5 min followed by addition of SO$_3$.py complex (0.604 g, 3.79 mmol) at 0° C. Ice bath was removed and the reaction mixture was stirred at room temperature for 2 h. The reaction mixture was quenched by addition of water and extracted with CH$_2$Cl$_2$ (3×30 mL). The combined organic layer was dried using Na$_2$SO$_4$, and the solvent was removed under reduced pressure. The crude product was purified by silica gel column chromatography (hexane: EtOAc=3:7) to give aldehyde 87a (0.25 g, 84%). The purified aldehyde was used immediately for next step. $^1$H NMR (600 MHz, CDCl$_3$): δ 9.74 (s, 1H), 8.23 (d, J=8.4 Hz, 1H), 7.94 (s, 1H), 7.84 (d, J=7.8 Hz, 1H), 7.80 (d, J=8.4 Hz, 1H), 7.36 (td, J=7.2, 1.2 Hz, 1H), 7.29 (td, J=7.2, 1.2 Hz, 1H), 6.97 (dd, J=6.6, 1.8 Hz, 1H), 3.36 (t, J=4.8 Hz, 4H), 3.24 (t, J=1.2 Hz, 2H), 2.73 (t, J=4.8 Hz, 4H), 1.75 (s, 9H).

tert-Butyl 3-(4-(2-oxoethyl)piperazin-1-yl)-9H-carbazole-9-carboxylate (87b)

Compound 86b (0.45 g, 1.14 mmol) in CH$_2$Cl$_2$ (10 mL) and DMSO (5 mL), was oxidized using SO$_3$.py complex (0.905 g, 5.69 mmol) and Et$_3$N (1.11 mL, 7.96 mmol) according to procedure F. The crude product was purified by silica gel column chromatography (EtOAc) to yield compound 87b (0.35 g, 78%). $^1$H NMR (600 MHz, CDCl$_3$): δ 9.76 (s, 1H), 8.28 (d, J=8.4 Hz, 1H), 8.18 (d, J=8.4 Hz, 1H), 7.93 (d, J=7.8 Hz, 1H), 7.48 (d, J=2.4 Hz, 1H), 7.44 (t, J=7.2 Hz, 1H), 7.32 (t, J=7.2 Hz, 1H), 7.12 (dd, J=6.6, 2.4 Hz, 1H), 3.31 (t, J=4.2 Hz, 4H), 3.25 (t, J=1.2 Hz, 2H), 2.74 (t, J=4.2 Hz, 4H), 1.74 (s, 9H).

tert-Butyl 4-(4-(2-oxoethyl)piperazin-1-yl)-9H-carbazole-9-carboxylate (87c)

Alcohol 86c (0.35 g, 0.88 mmol) was oxidized using SO$_3$.py complex (0.704 g, 4.425 mmol), DMSO (9 mL) and Et$_3$N (0.86 mL, 6.19 mmol) in CH$_2$Cl$_2$ (6 mL) according to procedure F. The crude product was purified by silica gel column chromatography (hexane:EtOAc=3:7) to give aldehyde 87c (0.31 g, 89%). The purified aldehyde was used immediately for next step. $^1$H NMR (600 MHz, CDCl$_3$): δ 9.78 (s, 1H), 8.33 (d, J=7.8 Hz, 1H), 8.27 (d, J=7.8 Hz, 1H), 7.84 (d, J=7.8 Hz, 1H), 8.09 (d, J=8.4 Hz, 1H), 7.44-7.40 (m, 2H), 7.35 (t, J=7.2 Hz, 1H), 7.06 (dd, J=7.8, 1.8 Hz, 1H), 3.36-3.34 (m, 4H), 3.06 (t, J=11.1 Hz, 2H), 2.73 (d, J=11.4 Hz, 2H), 2.71 (d, J=10.2 Hz, 2H), 1.75 (s, 9H).

Procedure G. tert-Butyl 2-(4-(2-((2-amino-4,5,6,7-tetrahydrobenzo[d]thiazol-6-yl)(propyl)amino)-ethyl)piperazin-1-yl)-9H-carbazole-9-carboxylate (88a)

Into a stirring solution of racemic N$^6$-propyl-4,5,6,7-tetrahydrobenzo[d]thiazole-2,6-diamine (0.058 g, 0.27 mmol) in CH$_2$Cl$_2$ (7 mL) was added aldehyde 87a (0.12 g, 0.31 mmol). After the mixture was stirred for 1.5 h, NaBH(OAc)$_3$ (0.13 g, 0.61 mmol) was added and the mixture was stirred for another 46 h at room temperature. The reaction mixture was quenched with a saturated solution of NaHCO$_3$ at 0° C. and extracted with CH$_2$Cl$_2$ (3×50 mL). The combined organic layer was dried over Na$_2$SO$_4$, and the solvent was removed under reduced pressure. The crude product was purified by silica gel column chromatography (CH$_2$Cl$_2$:MeOH=19:1) to afford compound 88a (0.06 g, 38%). $^1$H NMR (600 MHz, CDCl$_3$): δ 8.23 (d, J=8.4 Hz, 1H), 7.92 (s, 1H), 7.85 (d, J=7.8 Hz, 1H), 7.81 (d, J=8.4 Hz, 1H), 7.35 (td, J=7.2, 1.2 Hz, 1H), 7.29 (td, J=7.2, 1.2 Hz, 1H), 7.00 (dd, J=6.0, 2.4 Hz, 1H), 4.77 (bs, 2H), 3.33 (t, J=4.8 Hz, 4H), 3.07 (m, 1H), 2.78-2.68 (m, 8H), 2.60-2.47 (m, 6H), 2.02-2.00 (m, 1H), 1.75 (s, 10H), 1.51-1.47 (m, 2H), 0.90 (t, J=7.2 Hz, 3H).

tert-Butyl 3-(4-(2-((2-amino-4,5,6,7-tetrahydrobenzo[d]thiazol-6-yl)(propyl)amino) ethyl)piperazin-1-yl)-9H-carbazole-9-carboxylate (88b)

Aldehyde 87b (0.15 g, 0.38 mmol) in CH$_2$Cl$_2$ (10 mL) was reacted with racemic N$^6$-propyl-4,5,6,7-tetrahydrobenzo[d]thiazole-2,6-diamine (0.073 g, 0.34 mmol) and NaBH(OAc)$_3$ (0.162 g, 0.76 mmol) according to procedure G. Crude product was purified by column chromatography (EtOAc:MeOH=9:1) to afford compound 88b (0.065 g, 32%). $^1$H NMR (400 MHz, CDCl$_3$): δ 8.27 (d, J=8.0 Hz, 1H), 8.16 (d, J=9.2 Hz, 1H), 7.93 (d, J=7.6 Hz, 1H), 7.48 (d, J=2.4 Hz, 1H), 7.44 (t, J=7.2 Hz, 1H), 7.32 (t, J=7.2 Hz, 1H), 7.12 (dd, J=7.2, 2.4 Hz, 1H), 5.12 (bs, 2H), 3.28 (t, J=4.8 Hz, 4H), 3.07-3.02 (m, 1H), 2.78-2.67 (m, 8H), 2.58-2.45 (m, 6H), 2.00-1.98 (m, 1H), 1.74 (s, 10H), 1.52-1.46 (m, 2H), 0.90 (t, J=7.2 Hz, 3H).

tert-Butyl 4-(4-(2-((2-amino-4,5,6,7-tetrahydrobenzo[d]thiazol-6-yl)(propyl)amino) ethyl)piperazin-1-yl)-9H-carbazole-9-carboxylate (88c)

Aldehyde 87c (0.15 g, 0.38 mmol) was reacted with racemic N$^6$-propyl-4,5,6,7-tetrahydrobenzo[d]thiazole-2,6-diamine (0.073 g, 0.34 mmol) and NaBH(OAc)$_3$ (0.162 g, 0.76 mmol) in CH$_2$Cl$_2$ (10 mL) according to procedure G. The crude product was purified by silica gel column chromatography (CH$_2$Cl$_2$:MeOH=19:1) to afford compound 88c (0.91 g, 41%). $^1$H NMR (600 MHz, CDCl$_3$): δ 8.23 (d, J=6.6 Hz, 1H), 8.28 (d, J=6.6 Hz, 1H), 8.06 (d, J=6.6 Hz, 1H), 7.43 (d, J=5.4 Hz, 1H), 7.37 (d, J=5.4 Hz, 2H), 7.02 (d, J=6.0 Hz, 1H), 5.03 (s, 2H), 3.10-3.05 (m, 3H), 3.07-2.98 (m, 2H), 2.76-2.69 (m, 4H), 2.62-2.60 (m, 8H), 2.01-2.00 (m, 1H), 1.73 (s, 10H), 1.50-1.46 (m, 2H), 0.90 (t, J=7.2 Hz, 3H).

(S)-tert-Butyl 2-(4-(2-((2-amino-4,5,6,7-tetrahydrobenzo[d]thiazol-6-yl)(propyl) amino)ethyl)piperazin-1-yl)-9H-carbazole-9-carboxylate (89a)

Aldehyde 87a (0.125 g, 0.32 mmol) was reacted with (−)-pramipexole (0.06 g, 0.29 mmol) and NaBH(OAc)$_3$ (0.135 g, 0.64 mmol) in CH$_2$Cl$_2$ (8 mL) according to procedure G. The crude product was purified by silica gel column chromatography (CH$_2$Cl$_2$:MeOH=19:1) to afford compound 89a (0.067 g, 40%). $^1$H NMR (600 MHz, CDCl$_3$): δ 8.23 (d, J=8.4 Hz, 1H), 7.92 (s, 1H), 7.85 (d, J=7.2 Hz, 1H), 7.81 (d, J=8.4 Hz, 1H), 7.35 (td, J=7.2, 1.2 Hz, 1H), 7.29 (td, J=7.2, 1.2 Hz, 1H), 7.00 (dd, J=6.6, 2.4 Hz, 1H), 4.76 (bs, 2H), 3.33 (t, J=4.8 Hz, 4H), 3.07 (m, 1H), 2.79-2.68 (m, 8H), 2.61-2.48 (m, 6H), 2.02-2.00 (m, 1H), 1.75 (s, 10H), 1.51-1.48 (m, 2H), 0.90 (t, J=7.2 Hz, 3H); $[\alpha]_D^{25}$=−44.0 (c=1.0 in $CH_2Cl_2$).

(S)-tert-Butyl 3-(4-(2-((2-amino-4,5,6,7-tetrahydrobenzo[d]thiazol-6-yl)(propyl) amino)ethyl)piperazin-1-yl)-9H-carbazole-9-carboxylate (89b)

Aldehyde 87b (0.30 g, 0.76 mmol) was reacted with (−)-pramipexole (0.145 g, 0.69 mmol) and $NaBH(OAc)_3$ (0.323 g, 1.52 mmol) in $CH_2Cl_2$ (15 mL) according to procedure G. The crude product was purified by silica gel column chromatography (EtOAc:MeOH=9:1) to afford compound 89b (0.158 g, 39%). $^1H$ NMR (600 MHz, $CDCl_3$): δ 8.27 (d, J=7.2 Hz, 1H), 8.16 (d, J=8.4 Hz, 1H), 7.93 (d, J=7.8 Hz, 1H), 7.48 (d, J=2.4 Hz, 1H), 7.43 (t, J=7.2 Hz, 1H), 7.32 (t, J=7.2 Hz, 1H), 7.12 (dd, J=6.6, 2.4 Hz, 1H), 5.21 (bs, 2H), 3.28 (t, J=4.8 Hz, 4H), 3.07-3.02 (m, 1H), 2.78-2.66 (m, 8H), 2.59-2.46 (m, 6H), 2.01-1.99 (m, 1H), 1.74 (s, 10H), 1.52-1.46 (m, 2H), 0.90 (t, J=7.2 Hz, 3H).

(S)-tert-Butyl 4-(4-(2-((2-amino-4,5,6,7-tetrahydrobenzo[d]thiazol-6-yl)(propyl) amino)ethyl)piperazin-1-yl)-9H-carbazole-9-carboxylate (89c)

Aldehyde 87c (0.150 g, 0.38 mmol) was reacted with (−)-pramipexole (0.73 g, 0.54 mmol) and $NaBH(OAc)_3$ (0.162 g, 0.76 mmol) in $CH_2Cl_2$ (10 mL) according to procedure G. The crude product was purified by silica gel column chromatography ($CH_2Cl_2$:MeOH=19:1) to afford compound 89c (0.097 g, 43%). $^1H$ NMR (600 MHz, $CDCl_3$): δ 8.32 (d, J=7.2 Hz, 1H), 8.28 (d, J=7.8 Hz, 1H), 8.06 (d, J=7.8 Hz, 1H), 7.43 (d, J=7.2 Hz, 1H), 7.40-7.35 (m, 2H), 7.30 (d, J=7.2 Hz, 1H), 4.83 (bs, 2H), 3.33 (d, J=8.4 Hz, 2H), 3.06 (m, 3H), 2.99 (m, 2H), 2.76-2.70 (m, 4H), 2.60 (m, 7H), 1.74 (s, 10H), 1.51-1.48 (m, 2H), 0.90 (t, J=6.6 Hz, 3H); $[\alpha]_D^{25}$=−27.20 (c=1.0 in $CH_2Cl_2$).

Procedure H. $N^6$-(2-(4-(9H-carbazol-2-yl)piperazin-1-yl)ethyl)-$N^6$-propyl-4,5,6,7-tetrahydrobenzo-[d]thiazole-2,6-diamine (90a) (D-652)

To a stirred solution of 88a (0.055 g, 0.09 mmol) in $CH_2Cl_2$ (3 mL) at 0° C., trifluoroacetic acid (3 mL) was added slowly and the reaction mixture was stirred for 3 h at room temperature. Unreacted TFA and solvent were removed under reduced pressure and the obtained TFA salt was washed with ether for several times followed by drying to yield 90a (0.079 g, 90%). $^1H$ NMR (600 MHz, $CD_3OD$): δ 7.99 (d, J=8.4 Hz, 1H), 7.96 (d, J=7.8 Hz, 1H), 7.42 (d, J=7.8 Hz, 1H), 7.32 (t, J=7.2 Hz, 1H), 7.25 (s, 1H), 7.13 (t, J=7.2 Hz, 1H), 7.03 (d, J=8.4 Hz, 1H), 3.84 (m, 1H), 3.64-3.55 (m, 5H), 3.48-3.42 (m, 3H), 3.36 (s, 4H), 3.23-3.14 (m, 2H), 3.01-2.99 (m, 1H), 2.84-2.79 (m, 1H), 2.71-2.65 (m, 2H), 2.32-2.31 (m, 1H), 2.02-1.95 (m, 1H), 1.83-1.79 (m, 2H), 1.03 (t, J=7.2 Hz, 3H); $^{13}C$ NMR (150 MHz, $CD_3OD$): δ 170.28, 160.68, 145.32, 140.57, 132.69, 125.56, 124.53, 122.50, 121.20, 120.14, 119.84, 119.33, 118.79, 118.29, 117.08, 115.15, 111.37, 110.77, 109.73, 59.75, 52.49, 51.56, 50.08, 22.29, 21.88, 21.39, 18.01, 10.19; Anal. Calcd for $C_{28}H_{36}N_6S.4CF_3COOH$: C, 45.77; H, 4.27; N, 8.90. Found: C, 45.71; H, 4.64; N, 8.87.

$N^6$-(2-(4-(9H-carbazol-3-yl)piperazin-1-yl)ethyl)-$N^6$-propyl-4,5,6,7-tetrahydrobenzo[d]thiazole-2,6-diamine (90b) (D-627)

Compound 88b (0.05 g, 0.09 mmol) in $CH_2Cl_2$ (2 mL) at 0° C., was treated with trifluoroacetic acid (2 mL) according to procedure H to obtain the TFA salt of compound 90b (0.052 g, 84%). $^1H$ NMR (400 MHz, $CD_3OD$): δ 8.01 (d, J=8.0 Hz, 1H), 7.66 (d, J=1.6 Hz, 1H), 7.41-7.36 (m, 2H), 7.32 (t, J=7.2 Hz, 1H), 7.16-7.14 (m, 1H), 7.11 (t, J=7.2 Hz, 1H), 3.34 (s, 1H), 3.19 (s, 4H), 2.98-2.91 (m, 2H), 2.80-2.51 (m, 12H), 2.07-2.04 (m, 1H), 1.81-1.77 (m, 1H), 1.63-1.53 (m, 2H), 0.95 (t, J=7.2 Hz, 3H); $^{13}C$ NMR (100 MHz, $CD_3OD$): δ 168.63, 144.25, 143.69, 143.37, 140.69, 135.84, 125.07, 123.21, 122.92, 119.50, 118.21, 118.00, 113.45, 110.87, 110.41, 107.90, 58.85, 55.41, 53.24, 53.12, 51.07, 25.37, 24.70, 23.79, 20.35, 10.43; Anal. Calcd for $C_{28}H_{36}N_6S.2CF_3COOH$: C, 53.62; H, 5.34; N, 11.73. Found: C, 53.64; H, 5.83; N, 11.34.

$N^6$-(2-(4-(9H-carbazol-4-yl)piperazin-1-yl)ethyl)-$N^6$-propyl-4,5,6,7-tetrahydrobenzo[d]thiazole-2,6-diamine (90c) (D-658)

Compound 88c (0.082 g, 0.14 mmol) was treated with trifluoroacetic acid (3 mL) in $CH_2Cl_2$ (3 mL) according to procedure H to furnish the TFA salt of 90c (0.091 g, 90%). $^1H$ NMR (600 MHz, $CD_3OD$): δ 8.08 (d, J=7.8 Hz, 1H), 7.45 (d, J=7.8 Hz, 1H), 7.36 (t, J=7.8 Hz, 1H), 7.31 (t, J=7.8 Hz, 1H), 7.22 (d, J=7.8 Hz, 1H), 7.19 (t, J=7.2 Hz, 1H), 6.82 (d, J=7.8 Hz, 1H), 3.94-3.89 (m, 1H), 3.83 (d, J=7.2 Hz, 2H), 3.77-3.59 (m, 8H), 3.29 (d, J=1.2 Hz, 1H), 3.24-3.20 (m, 3H), 3.06-3.04 (m, 1H), 2.92-2.88 (m, 1H), 2.78-2.71 (m, 2H), 2.37-2.36 (m, 1H), 2.11-2.04 (m, 1H), 1.86-1.82 (m, 2H), 1.04 (t, J=7.2 Hz, 3H); $^{13}C$ NMR (150 MHz, $CD_3OD$): δ 170.32, 161.19, 146.42, 141.50, 139.78, 132.81, 125.91, 124.74, 121.78, 121.34, 118.62, 115.64, 111.66, 110.23, 107.39, 59.17, 53.36, 53.25, 52.80, 50.81, 48.60, 48.01, 44.95, 22.51, 22.03, 21.49, 18.34, 9.79; Anal. Calcd for $C_{28}H_{36}N_6S, 3CF_3COOH, CH_3OH, H_2O$: C, 47.73; H, 5.15; N, 9.54. Found: C, 47.63; H, 4.67; N, 9.23.

(S)—$N^6$-(2-(4-(9H-carbazol-2-yl)piperazin-1-yl)ethyl)-$N^6$-propyl-4,5,6,7-tetrahydrobenzo[d]thiazole-2,6-diamine (91a) (D-651)

Compound 89a (0.065 g, 0.11 mmol) was treated with trifluoroacetic acid (3 mL) in $CH_2Cl_2$ (3 mL) according to procedure H to furnish the TFA salt of 91a (0.085 g, 93%). $^1H$ NMR (600 MHz, $CD_3OD$): δ 7.99 (d, J=8.4 Hz, 1H), 7.96 (d, J=7.8 Hz, 1H), 7.42 (d, J=7.8 Hz, 1H), 7.33 (t, J=7.2 Hz, 1H), 7.26 (s, 1H), 7.13 (t, J=7.2 Hz, 1H), 7.04 (d, J=8.4 Hz, 1H), 3.86 (m, 1H), 3.65-3.56 (m, 5H), 3.49-3.42 (m, 3H), 3.37 (s, 4H), 3.25-3.16 (m, 2H), 3.02-3.00 (m, 1H), 2.85-2.81 (m, 1H), 2.73-2.66 (m, 2H), 2.34-2.32 (m, 1H), 2.04-1.97 (m, 1H), 1.83-1.80 (m, 2H), 1.03 (t, J=7.2 Hz, 3H); $^{13}C$ NMR (150 MHz, $CD_3OD$): δ 170.29, 160.41, 145.25, 140.58, 132.67, 125.55, 124.55, 122.49, 121.21, 120.15, 119.82, 119.32, 118.82, 118.24, 116.97, 115.06, 111.39, 110.76, 109.70, 59.75, 52.50, 51.55, 50.17, 22.31, 21.89, 21.40, 17.98, 10.18; $[\alpha]_D^{25}$=−24.8 (c=1.0 in $CH_3OH$); Anal. Calcd for $C_{28}H_{36}N_6S.3CF_3COOH.2H_2O$: C, 47.11; H, 5.00; N, 9.70. Found: C, 47.63; H, 4.67; N, 9.23.

(S)—$N^6$-(2-(4-(9H-carbazol-3-yl)piperazin-1-yl)ethyl)-$N^6$-propyl-4,5,6,7-tetrahydrobenzo[d]thiazole-2,6-diamine (91b) (D-636)

Compound 89b (0.15 g, 0.25 mmol) was treated with trifluoroacetic acid (8 mL) in $CH_2Cl_2$ (8 mL) according to procedure H to furnish the TFA salt of 91b (0.20 g, 96%). $^1H$ NMR (600 MHz, $CD_3OD$): δ 8.27 (s, 1H), 8.11 (d, J=7.2 Hz, 1H), 7.59-7.54 (m, 2H), 7.49 (d, J=8.4 Hz, 1H), 7.44 (t, J=7.2 Hz, 1H), 7.21 (t, J=7.2 Hz, 1H), 3.96 (m, 1H), 3.80 (s, 4H), 3.57-3.45 (m, 2H), 3.34-3.27 (m, 2H), 3.20-3.10 (m, 7H), 2.97-2.92 (m, 1H), 2.83-2.75 (m, 2H), 2.44-2.42 (m, 1H), 2.17-2.10 (m, 1H), 1.90-1.84 (m, 2H), 1.07 (t, J=7.2 Hz, 3H); $^{13}$C NMR (150 MHz, CD$_3$OD): δ 170.35, 160.54, 141.04, 139.17, 135.08, 132.80, 126.39, 123.44, 122.29, 119.95, 119.05, 117.60, 111.67, 111.55, 111.45, 110.90, 59.31, 54.18, 53.61, 51.21, 50.61, 22.42, 22.09, 21.50, 17.98, 9.82; $[α]_D^{25}$=−17.4 (c=1.0 in CH$_3$OH); Anal. Calcd for C$_{28}$H$_{36}$N$_6$S.3CF$_3$COOH.H$_2$O: C, 48.11; H, 4.87; N, 9.90. Found: C, 48.25; H, 4.99; N, 9.58.

(S)—N$^6$-(2-(4-(9H-carbazol-4-yl)piperazin-1-yl)ethyl)-N$^6$-propyl-4,5,6,7-tetrahydrobenzo[d]thiazole-2,6-diamine (91c) (D-657)

Compound 89c (0.83 g, 0.14 mmol) was treated with trifluoroacetic acid (7 mL) in CH$_2$Cl$_2$ (7 mL) according to procedure H to furnish the TFA salt of 91c (0.085 g, 93%). $^1$H NMR (600 MHz, CD$_3$OD): δ 8.07 (d, J=7.2 Hz, 1H), 7.44 (d, J=7.8 Hz, 1H), 7.36 (d, J=7.8 Hz, 1H), 7.31 (t, J=7.8 Hz, 1H), 7.22 (d, J=7.8 Hz, 1H), 7.19 (t, J=7.2 Hz, 1H), 6.81 (d, J=8.4 Hz, 1H), 3.90 (s, 1H) 3.84 (d, J=6.6 Hz, 2H), 3.78-3.71 (m, 4H), 3.56-3.43 (m, 4H), 3.29 (s, 2H), 3.26-3.21 (m, 3H), 3.06-3.04 (m, 1H), 2.92-2.88 (m, 1H), 2.78-2.71 (m, 2H), 2.36 (bs, 1H), 2.09-2.04 (m, 1H), 1.86-1.82 (m, 2H), 1.04 (t, J=7.2 Hz, 3H); $^{13}$C NMR (150 MHz, CD$_3$OD): δ 170.32, 161.06, 146.42, 139.77, 132.80, 126.38, 124.29, 122.26, 121.30, 119.075, 118.18, 115.62, 111.61, 110.74, 109.72, 59.72, 58.72, 53.27, 52.76, 50.70, 44.91, 22.99, 22.34, 21.44, 18.30, 10.07, 9.46; $[α]_D^{25}$=−25.0 (c=1.0 in CH$_3$OH); Anal. Calcd for C$_{28}$H$_{36}$N$_6$S.3CF$_3$COOH: C, 49.16; H, 4.73; N, 10.12. Found: C, 48.93; H, 4.84; N, 9.77.

tert-Butyl 2-(4-(2-((5-methoxy-1,2,3,4-tetrahydronaphthalen-2-yl)(propyl)amino) ethyl)-piperazin-1-yl)-9H-carbazole-9-carboxylate (92a)

Compound 87a (0.10 g, 0.25 mmol) was reacted with (±)-(5-methoxy-1,2,3,4-tetrahydro-naphthalen-2-yl)-propyl-amine (0.056 g, 0.25 mmol) and NaBH(OAc)$_3$ (0.108 g, 0.51 mmol) in CH$_2$Cl$_2$ (7 mL) according to procedure G. The crude product was purified by silica gel column chromatography (hexane:EtOAc=1:3) to afford compound 92a (0.115 g, 77%). $^1$H NMR (600 MHz, CDCl$_3$): δ 8.23 (d, J=7.8 Hz, 1H), 7.91 (s, 1H), 7.83 (d, J=7.8 Hz, 1H), 7.79 (d, J=8.4 Hz, 1H), 7.34 (t, J=7.2 Hz, 1H), 7.28 (t, J=7.2 Hz, 1H), 7.08 (t, J=7.8 Hz, 1H), 6.98 (dd, J=6.6, 1.8 Hz, 1H), 6.72 (d, J=7.2 Hz, 1H), 6.64 (d, J=7.8 Hz, 1H), 3.79 (s, 3H), 3.32 (t, J=4.8 Hz, 4H), 3.02-2.93 (m, 2H), 2.88-2.85 (m, 1H), 2.79-2.75 (m, 3H), 2.70 (t, J=4.8 Hz, 4H), 2.56-2.50 (m, 5H), 2.09-2.06 (m, 1H), 1.74 (s, 9H), 1.62-1.55 (m, 1H), 1.53-1.47 (m, 2H), 0.91 (t, J=7.2 Hz, 3H).

tert-Butyl 3-(4-(2-((5-methoxy-1,2,3,4-tetrahydronaphthalen-2-yl)(propyl)amino) ethyl)piperazin-1-yl)-9H-carbazole-9-carboxylate (92b)

Compound 87b (0.170 g, 0.43 mmol) was reacted with (±)-(5-methoxy-1,2,3,4-tetrahydro-naphthalen-2-yl)-propyl-amine (0.095 g, 0.43 mmol) and NaBH(OAc)$_3$ (0.183 g, 0.86 mmol) in CH$_2$Cl$_2$ (10 mL) according to procedure G. The crude product was purified by silica gel column chromatography with EtOAc to afford compound 92b (0.11 g, 43%). $^1$H NMR (600 MHz, CDCl$_3$): δ 8.27 (d, J=7.8 Hz, 1H), 8.16 (d, J=8.4 Hz, 1H), 7.92 (d, J=7.8 Hz, 1H), 7.47 (d, J=2.4 Hz, 1H), 7.43 (t, J=7.2 Hz, 1H), 7.31 (t, J=7.2 Hz, 1H), 7.12 (dd, J=6.6, 2.4 Hz, 1H), 7.08 (t, J=8.4 Hz, 1H), 6.72 (d, J=7.2 Hz, 1H), 6.64 (d, J=8.4 Hz, 1H), 3.79 (s, 3H), 3.27 (t, J=4.8 Hz, 4H), 3.03-2.98 (m, 2H), 2.90-2.87 (m, 1H), 2.81-2.77 (m, 3H), 2.73 (t, J=4.8 Hz, 4H), 2.59-2.51 (m, 5H), 2.11-2.08 (m, 1H), 1.74 (s, 9H), 1.63-1.57 (m, 1H), 1.55-1.49 (m, 2H), 0.91 (t, J=7.2 Hz, 3H).

tert-Butyl 4-(4-(2-((5-methoxy-1,2,3,4-tetrahydronaphthalen-2-yl)(propyl)amino) ethyl)piperazin-1-yl)-9H-carbazole-9-carboxylate (92c)

Compound 87c (0.10 g, 0.25 mmol) was reacted with (±)-(5-methoxy-1,2,3,4-tetrahydro-naphthalen-2-yl)-propyl-amine (0.055 g, 0.25 mmol) and NaBH(OAc)$_3$ (0.108 g, 0.50 mmol) in CH$_2$Cl$_2$ (8 mL) according to procedure G. The crude product was purified by silica gel column chromatography (hexane:EtOAc=1:3) to afford compound 92c (0.112 g, 74%). $^1$H NMR (600 MHz, CDCl$_3$): δ 8.23 (d, J=8.4 Hz, 1H), 8.16 (d, J=8.4, Hz, 1H), 8.09 (d, J=7.2 Hz, 1H), 7.47 (d, J=7.8 Hz, 1H), 7.39 (m, 2H), 7.13 (t, J=7.8 Hz, 1H), 7.00 (d, J=7.8 Hz, 1H), 6.70 (q, J=7.8 Hz, 2H), 3.92 (bs, 2H), 3.79 (s, 3H), 3.58-3.48 (m, 4H), 2.29 (m, 2H), 3.06-3.04 (m, 5H), 2.62, (m, 1H), 2.37 (bs, 1H), 2.09-2.06 (m, 1H), 1.74 (s, 9H), 1.62-1.55 (m, 1H), 1.53-1.47 (m, 2H), 0.92 (t, J=7.2 Hz, 3H).

(S)-tert-Butyl 2-(4-(2-((5-methoxy-1,2,3,4-tetrahydronaphthalen-2-yl)(propyl) amino)ethyl)piperazin-1-yl)-9H-carbazole-9-carboxylate (93a)

Compound 87a (0.10 g, 0.25 mmol) was reacted with (−)-(5-methoxy-1,2,3,4-tetrahydro-naphthalen-2-yl)-propyl-amine (0.056 g, 0.25 mmol) and NaBH(OAc)$_3$ (0.108 g, 0.51 mmol) in CH$_2$Cl$_2$ (7 mL) according to procedure G. The crude product was purified by silica gel column chromatography (hexane:EtOAc=1:3) to afford compound 93a (0.11 g, 74%). $^1$H NMR (600 MHz, CDCl$_3$): δ 8.23 (d, J=8.4 Hz, 1H), 7.91 (s, 1H), 7.82 (d, J=7.8 Hz, 1H), 7.78 (d, J=8.4 Hz, 1H), 7.34 (t, J=7.2 Hz, 1H), 7.28 (t, J=7.2 Hz, 1H), 7.08 (t, J=7.8 Hz, 1H), 6.97 (dd, J=6.6, 1.8 Hz, 1H), 6.71 (d, J=7.2, Hz, 1H), 6.63 (d, J=7.8 Hz, 1H), 3.78 (s, 3H), 3.32 (t, J=4.8 Hz, 4H), 3.02-2.94 (m, 2H), 2.88-2.85 (m, 1H), 2.79-2.74 (m, 3H), 2.70 (t, J=4.8 Hz, 4H), 2.56-2.50 (m, 5H), 2.08-2.06 (m, 1H), 1.74 (s, 9H), 1.61-1.54 (m, 1H), 1.52-1.47 (m, 2H), 0.91 (t, J=7.2 Hz, 3H); $[α]_D^{25}$=−28.6 (c=1.0 in CH$_2$Cl$_2$).

(S)-tert-Butyl 3-(4-(2-((5-methoxy-1,2,3,4-tetrahydronaphthalen-2-yl)(propyl)amino) ethyl)piperazin-1-yl)-9H-carbazole-9-carboxylate (93b)

Compound 87b (0.140 g, 0.456 mmol) was reacted with (−)-(5-methoxy-1,2,3,4-tetrahydro-naphthalen-2-yl)-propyl-amine (0.070 g, 0.32 mmol) and NaBH(OAc)$_3$ (0.151 g, 0.71 mmol) in CH$_2$Cl$_2$ (10 mL) according to procedure G. The crude product was purified by silica gel column chromatography with EtOAc to afford compound 13b (0.07 g, 33%). $^1$H NMR (600 MHz, CDCl$_3$): δ 8.18 (d, J=6 Hz, 1H), 8.09 (m, 1H), 7.83 (d, J=7.2 Hz, 1H), 7.38-7.32 (m, 2H), 7.23 (q, J=9.6, 7.5 Hz, 1H), 7.03 (d, J=9 Hz, 1H), 6.99 (t, J=7.8 Hz, 1H), 6.63 (d, J=6.6 Hz, 1H), 6.55 (d, J=7.8, Hz, 1H), 3.70 (s, 3H), 3.18 (t, J=4.2 Hz, 4H), 3.27-3.26 (m, 1H), 3.12-3.10 (m, 2H), 2.93-2.90 (m, 2H), 2.81-2.78 (m, 1H), 2.69-2.64 (m, 5H), 2.48-2.43 (m, 4H), 2.03-2.00 (m, 1H), 1.65 (s, 9H), 1.54-1.47 (m, 1H), 1.45-1.37 (m, 2H), 0.82 (t, J=7.2 Hz, 3H).

(S)-tert-Butyl 4-(4-(2-((5-methoxy-1,2,3,4-tetrahydronaphthalen-2-yl)(propyl)amino)ethyl)piperazin-1-yl)-9H-carbazole-9-carboxylate (93c)

Compound 87c (0.10 g, 0.25 mmol) was reacted with (−)-(5-methoxy-1,2,3,4-tetrahydro-naphthalen-2-yl)-propyl-amine (0.055 g, 0.25 mmol) and NaBH(OAc)$_3$ (0.108 g, 0.50 mmol) in CH$_2$Cl$_2$ (8 mL) according to procedure G. The crude product was purified by silica gel column chromatography (hexane:EtOAc=1:3) to afford compound 93c (0.124 g, 82%). $^1$H NMR (600 MHz, CDCl$_3$): δ 8.35-8.30 (m, 2H), 7.07 (d, J=7.8 Hz, 1H), 7.44-7.41 (m, 1H), 7.41-7.39 (m, 2H), 7.08 (d, J=7.8 Hz, 1H), 7.04 (d, J=7.8 Hz, 1H), 6.73 (d, J=7.2, Hz, 1H), 6.64 (d, J=8.4 Hz, 1H), 3.79 (s, 3H), 3.53-3.48 (m, 4H), 3.29 (m, 2H), 3.16-3.04 (m, 5H), 2.67-2.60 (m, 1H), 2.37 (bs, 1H), 2.03-2.01 (m, 2H), 1.85-1.84 (m, 3H), 1.75 (s, 9H), 1.26-1.24 (m, 3H), 0.92 (t, J=7.2 Hz, 3H); [α]$_D^{25}$=−20.3 (c=1.0 in CH$_2$Cl$_2$).

Procedure I. 6-((2-(4-(9H-carbazol-2-yl)piperazin-1-yl)ethyl)(propyl)amino)-5,6,7,8-tetrahydronaphthalen-1-ol (94a) (D-654)

A mixture of compound 92a (0.10 g, 0.17 mmol) and 48% aqueous HBr (8 mL) was refluxed at 130° C. for 4 h. The reaction mixture was evaporated to dryness, washed with ether followed by vacuo drying to yield HBr salt of 94a (0.095 g, 78%). $^1$H NMR (600 MHz, CD$_3$OD): δ 8.11 (d, J=8.4 Hz, 1H), 8.03 (d, J=7.8 Hz, 1H), 7.67-7.62 (m, 1H), 7.46 (d, J=7.8 Hz, 1H), 7.38 (t, J=7.2 Hz, 1H), 7.34-7.29 (m, 1H), 7.17 (t, J=7.2 Hz, 1H), 6.96 (t, J=7.8 Hz, 1H), 6.67 (d, J=7.8, Hz, 1H), 6.62 (d, J=7.8 Hz, 1H), 3.99-3.86 (m, 5H), 3.84-3.72 (m, 5H), 3.68-3.63 (m, 2H), 3.39 (m, 1H), 3.33-3.29 (m, 2H), 3.16-3.08 (m, 2H), 2.71-2.66 (m, 1H), 2.63 (m, 1H), 2.49-2.47 (m, 1H), 2.00-1.93 (m, 3H), 1.07 (t, J=7.2 Hz, 3H); $^{13}$C NMR (150 MHz, CD$_3$OD): δ 154.74, 140.88, 140.12, 133.27, 129.28, 126.63, 125.85, 122.06, 121.59, 121.12, 120.99, 119.93, 119.78, 119.11, 117.61, 112.08, 110.61, 110.26, 61.26, 52.93, 51.47, 50.73, 50.47, 50.32, 45.16, 29.29, 23.55, 22.35, 18.26, 9.92, 8.31; Anal. Calcd for C$_{31}$H$_{38}$N$_4$O.3HBr: C, 51.33; H, 5.70; N, 7.72. Found: C, 51.50; H, 5.92; N, 7.46.

6-((2-(4-(9H-carbazol-3-yl)piperazin-1-yl)ethyl)(propyl)amino)-5,6,7,8-tetrahydro-naphthalen-1-ol (94b) (D-650)

A mixture of compound 92b (0.08 g, 0.13 mmol) and 48% aqueous HBr (7 mL) was refluxed according to procedure I to yield HBr salt of 94b (0.095 g, 98%). $^1$H NMR (600 MHz, CD$_3$OD): δ 8.58 (s, 1H), 8.14 (d, J=7.8 Hz, 1H), 7.76 (d, J=8.4 Hz, 1H), 7.61 (d, J=9.0 Hz, 1H), 7.50 (d, J=7.8 Hz, 1H), 7.44 (t, J=7.2 Hz, 1H), 7.21 (t, J=7.2 Hz, 1H), 6.94 (t, J=7.8 Hz, 1H), 6.66 (d, J=7.8 Hz, 1H), 6.61 (d, J=7.8, Hz, 1H), 4.30 (s, 4H), 4.11-4.04 (m, 6H), 3.93-3.89 (m, 2H), 3.78 (s, 1H), 3.46-3.39 (m, 1H), 3.33-3.29 (m, 2H), 3.22-3.16 (m, 1H), 3.09-3.05 (m, 1H), 2.72-2.69 (m, 1H), 2.52-2.47 (m, 1H), 2.02-1.94 (m, 3H), 1.07 (t, J=7.2 Hz, 3H); $^{13}$C NMR (150 MHz, CD$_3$OD): δ 154.67, 141.05, 139.88, 133.32, 132.51, 127.22, 126.31, 123.45, 122.11, 121.60, 120.77, 120.15, 119.76, 117.91, 116.92, 112.40, 112.24, 111.96, 111.54, 111.40, 110.53, 60.95, 53.09, 50.47, 49.91, 29.34, 22.81, 22.37, 18.30, 10.26, 9.73; Anal. Calcd for C$_{31}$H$_{38}$N$_4$O.3HBr.2H$_2$O: C, 48.90; H, 5.96; N, 7.36. Found: C, 49.30; H, 5.86; N, 7.24.

6-((2-(4-(9H-carbazol-4-yl)piperazin-1-yl)ethyl)(propyl)amino)-5,6,7,8-tetrahydro-naphthalen-1-ol (94c) (D-655)

Compound 92c (0.11 g, 0.18 mmol) was refluxed with 48% aqueous HBr (8 mL) according to procedure I to yield HBr salt of 94c (0.097 g, 78%). $^1$H NMR (600 MHz, CD$_3$OD): δ 8.11 (d, J=7.8 Hz, 1H), 8.07 (d, J=7.8 Hz, 1H), 7.46-7.43 (m, 1H), 7.37-7.32 (m, 1H), 7.31-7.27 (m, 1H), 7.25-7.19 (m, 1H), 6.95 (t, J=7.8 Hz, 1H), 6.87 (d, J=7.8 Hz, 1H), 6.79 (d, J=6.6, Hz, 1H), 6.61 (d, J=7.8 Hz, 1H), 4.02 (s, 3H), 3.90-3.85 (m, 5H), 3.58-3.57 (m, 3H), 3.39 (m, 2H), 3.33-3.29 (m, 2H), 3.29-3.17 (m, 2H), 3.11-3.08 (m, 1H), 2.72-2.70 (m, 1H), 2.48 (m, 1H), 1.99-1.94 (m, 3H), 1.07 (t, J=7.2 Hz, 3H); $^{13}$C NMR (150 MHz, CD$_3$OD): δ 154.71, 141.47, 139.70, 133.20, 126.61, 125.85, 124.74, 121.97, 121.81, 121.58, 121.25, 119.96, 118.76, 118.66, 115.57, 112.07, 110.24, 110.21, 107.23 61.40, 52.89, 50.25, 48.57, 47.09, 45.57, 43.81, 29.23, 23.57, 22.30, 18.45, 9.91; Anal. Calcd for C$_{31}$H$_{38}$N$_4$O.3HBr: C, 51.33; H, 5.70; N, 7.72. Found: C, 51.07; H, 5.91; N, 8.17.

(S)-6-((2-(4-(9H-carbazol-2-yl)piperazin-1-yl)ethyl)(propyl)amino)-5,6,7,8-tetrahydronaphthalen-1-ol (95a) (D-653)

Compound 93a (0.10 g, 0.17 mmol) was refluxed with 48% aqueous HBr (8 mL) according to procedure I to yield HBr salt of 95a (0.10 g, 82%). $^1$H NMR (600 MHz, CD$_3$OD): δ 8.11 (d, J=8.4 Hz, 1H), 8.03 (d, J=7.8 Hz, 1H), 7.62 (m, 1H), 7.46 (d, J=7.8 Hz, 1H), 7.38 (t, J=7.2 Hz, 1H), 7.34-7.28 (m, 1H), 7.17 (t, J=7.2 Hz, 1H), 6.96 (t, J=7.8 Hz, 1H), 6.68 (d, J=7.8 Hz, 1H), 6.62 (d, J=7.8 Hz, 1H), 3.99 (s, 3H), 3.93-3.85 (m, 2H), 3.82-3.63 (m, 7H), 3.39 (m, 1H), 3.33-3.29 (m, 2H), 3.17-3.08 (m, 2H), 2.70 (m, 1H), 2.63-2.62 (m, 1H), 2.49-2.47 (m, 1H), 2.01-1.94 (m, 3H), 1.07 (t, J=7.2 Hz, 3H); $^{13}$C NMR (150 MHz, CD$_3$OD): δ 154.73, 140.86, 140.14, 133.28, 129.27, 126.62, 125.82, 122.08, 121.60, 121.09, 120.97, 119.93, 119.76, 119.10, 117.58, 112.08, 110.60, 110.26, 72.29, 61.27, 52.94, 51.83, 51.45, 50.78, 50.49, 41.61, 29.31, 23.48, 22.35, 18.26, 9.92, 8.31; [α]$_D^{25}$=−21.5 (c=1.0 in CH$_3$OH); Anal. Calcd for C$_{31}$H$_{38}$N$_4$O.3HBr: C, 51.33; H, 5.70; N, 7.72. Found: C, 51.44; H, 5.93; N, 7.47.

(S)-6-((2-(4-(9H-carbazol-3-yl)piperazin-1-yl)ethyl)(propyl)amino)-5,6,7,8-tetra-hydronaphthalen-1-ol (95b) (D-659)

Compound 93b (0.07 g, 0.12 mmol) was refluxed with 48% aqueous HBr (7 mL) according to procedure I to yield HBr salt of 95b (0.085 g, 97%). $^1$H NMR (600 MHz, CD$_3$OD): δ 8.58 (s, 1H), 8.15 (q, J=7.8 Hz, 2H), 7.76 (d, J=6.6 Hz, 1H), 7.61 (d, J=8.4 Hz, 1H), 7.57 (d, J=7.8 Hz, 1H), 7.43 (q, J=7.8 Hz, 1H), 7.21 (d, J=7.8 Hz, 1H), 6.94 (t, J=7.2 Hz, 1H), 6.66 (d, J=7.2 Hz, 1H), 6.61 (d, J=7.8 Hz, 1H), 4.17 (s, 4H), 3.91-3.85 (m, 6H), 3.87-3.85 (m, 2H), 3.57 (s, 1H), 3.50-3.49 (m, 1H), 3.32-3.28 (m, 2H), 3.17-3.14 (m, 1H), 3.08-3.05 (m, 1H), 2.69-2.67 (m, 1H), 2.51-2.46 (m, 1H), 1.96-1.93 (m, 3H), 1.48 (t, J=6.0 Hz, 3H); $^{13}$C NMR (150 MHz, CD$_3$OD): δ 157.19, 151.08, 147.936, 147.513.32, 138.93, 137.85, 133.55, 132.78, 129.08, 127.16, 126.92, 122.87, 122.74, 121.64, 119.43, 118.42, 117.40, 107.78, 106.90, 106.54, 57.16, 55.21, 51.85, 50.41, 48.10, 40.131, 29.71, 25.60, 23.87, 22.08, 11.92; $[\alpha]_D^{25}$=−22.2 (c=1.0 in $CH_3OH$); Anal. Calcd for $C_{31}H_{38}N_4O$.4HBr: C, 46.18; H, 5.25; N, 6.95. Found: C, 46.13; H, 5.66; N, 7.59.

(S)-6-((2-(4-(9H-carbazol-4-yl)piperazin-1-yl)ethyl)(propyl)amino)-5,6,7,8-tetra-hydronaphthalen-1-ol (95c) (D-656)

Compound 93c (0.112 g, 0.18 mmol) was refluxed with 48% aqueous HBr (9 mL) according to procedure I to yield HBr salt of 95c (0.10 g, 82%). $^1$H NMR (600 MHz, $CD_3OD$): δ 8.09 (d, J=7.2 Hz, 1H), 7.34 (d, J=8.4 Hz, 1H), 7.33 (t, J=7.2 Hz, 1H), 7.26 (dd, J=4.8, 2.4 Hz, 1H), 7.20 (d, J=8.4 Hz, 2H), 6.92 (t, J=7.8 Hz, 1H), 6.72 (d, J=7.2 Hz, 1H), 6.65 (d, J=7.2 Hz, 1H), 6.62 (d, J=7.8, Hz, 1H), 4.02 (s, 3H), 3.90-3.84 (m, 6H), 3.59-3.56 (m, 2H), 3.40 (m, 2H), 3.30-3.28 (m, 2H), 3.19-3.14 (m, 1H), 3.06-3.05 (m, 1H), 2.71-2.68 (m, 1H), 2.47 (bs, 1H), 1.96-1.92 (m, 3H), 1.05 (t, J=7.2 Hz, 3H); $^{13}$C NMR (150 MHz, $CD_3OD$): δ 154.69, 141.41, 139.73, 133.24, 127.24, 125.30, 124.28, 122.56, 121.57, 121.21, 120.28, 119.63, 119.28, 118.33, 115.52, 112.43, 111.75, 110.77, 109.71, 107.68, 61.27, 52.94, 51.83, 60.95, 52.82, 50.31, 44.47, 43.68, 22.53, 18.97, 9.92; $[\alpha]_D^{25}$=−17.8 (c=1.0 in $CH_3OH$); Anal. Calcd for) $C_{31}H_{38}N_4O$.2HBr. $CH_2Cl_2$: C, 52.69; H, 5.80; N, 7.68. Found: C, 52.23; H, 6.18; N, 7.96.

9-(2-bromoethyl)-9H-carbazole (96)

A suspension of carbazole (1.0 g, 5.98 mmol), $K_2CO_3$ (1.82 g, 13.16 mmol), tetrabutylammonium bromide (0.039 g, 0.12 mmol) and KOH (2.25 g, 40.07 mmol) in dibromoethane (10 mL, 119.61 mmol) was stirred at 50° C. under $N_2$ overnight. The reaction mixture was filtered off and diluted with $CH_2Cl_2$. The organic layer was washed with water, dried over sodium sulfate, filtered and concentrated. The crude product was purified by silica gel column chromatography with petroleum ether to afford compound 96 (0.52 g, 32%). $^1$H NMR (400 MHz, $CDCl_3$): δ 8.10 (d, J=7.6 Hz, 2H), 7.51-7.42 (m, 4H), 7.29-7.25 (m, 2H), 4.71 (t, J=7.2 Hz, 2H), 3.68 (t, J=7.2 Hz, 2H).

9-(2-(4-(2-((tert-butyldimethylsilyl)oxy)ethyl)piperazin-1-yl)ethyl)-9H-carbazole (97)

A mixture of compound 96 (0.7 g, 2.55 mmol), 1-(2-((tert-butyldimethylsilyl)-oxy)ethyl)piperazine (0.75 g, 3.06 mmol), and $K_2CO_3$ (1.06 g, 7.66 mmol) in acetonitrile (20 mL) was refluxed for 24 h under inert condition. The reaction mixture was cooled to room temperature, filtered, washed with EtOAc and concentrated in vacuo. The crude material was purified by silica gel column chromatography (hexane:EtOAc=3:2) to give compound 97 (0.81 g, 73%). $^1$H NMR (400 MHz, $CDCl_3$): δ 8.09 (d, J=7.2 Hz, 2H), 7.49-7.41 (m, 4H), 7.25-7.21 (m, 2H), 4.45 (t, J=7.2 Hz, 2H), 3.76 (t, J=6.8 Hz, 2H), 2.76 (t, J=7.2 Hz, 2H), 2.68-2.57 (m, 6H), 2.54 (t, J=6.4 Hz, 4H), 0.90 (s, 9H), 0.06 (s, 6H).

2-(4-(2-(9H-carbazol-9-yl)ethyl)piperazin-1-yl)ethanol (98)

Compound 97 (0.875 g, 2.0 mmol) was treated with n-tetrabutylammonium fluoride (4.0 mL, 4.0 mmol, 1.0 M solution in THF) in THF (12 mL) according to procedure E. The crude product was purified by silica gel column chromatography (EtOAc:MeOH=5:1) to give compound 98 (0.525 g, 81%). $^1$H NMR (400 MHz, $CDCl_3$): δ 8.09 (d, J=7.2 Hz, 2H), 7.48-7.41 (m, 4H), 7.25-7.21 (m, 2H), 4.44 (t, J=7.2 Hz, 2H), 3.62 (t, J=5.4 Hz, 2H), 2.82-2.76 (m, 4H), 2.61-2.55 (m, 8H).

2-(4-(2-(9H-carbazol-9-yl)ethyl)piperazin-1-yl)acetaldehyde (99)

Alcohol 98 (0.30 g, 0.93 mmol) was oxidized using $SO_3$.py complex (0.74 g, 4.64 mmol), DMSO (3 mL) and $Et_3N$ (0.90 mL, 6.49 mmol) in $CH_2Cl_2$ (6 mL) according to procedure F. The crude product was purified by silica gel column chromatography (EtOAc:MeOH=9:1) to give aldehyde 99 (0.23 g, 77%). The purified aldehyde was used immediately for next step. $^1$H NMR (600 MHz, $CDCl_3$): δ 9.67 (s, 1H), 8.07 (d, J=7.8 Hz, 2H), 7.47-7.41 (m, 4H), 7.23-7.21 (m, 2H), 4.44-4.42 (m, 2H), 3.38-3.36 (m, 2H), 2.78-2.74 (m, 4H), 2.60-2.56 (m, 6H).

$N^6$-(2-(4-(2-(9H-carbazol-9-yl)ethyl)piperazin-1-yl)ethyl)-$N^6$-propyl-4,5,6,7-tetrahydrobenzo[d]thiazole-2,6-diamine (100) (D-626)

Compound 99 (0.14 g, 0.44 mmol) was reacted with (±)-pramipexole (0.083 g, 0.39 mmol) and $NaBH(OAc)_3$ (0.185 g, 0.87 mmol) in $CH_2Cl_2$ (10 mL) according to procedure G. The crude product was purified by silica gel column chromatography (EtOAc:MeOH=4:1) to afford compound 100 (0.115 g, 57%). The compound was converted to HCl salt. $^1$H NMR (400 MHz, $CDCl_3$): δ 8.07 (d, J=8.4 Hz, 2H), 7.47-7.39 (m, 4H), 7.23-7.20 (m, 2H), 5.20 (bs, 2H), 4.41 (t, J=7.2 Hz, 2H), 3.04-2.97 (m, 1H), 2.75 (t, J=7.2 Hz, 2H), 2.69-2.48 (m, 14H), 2.45 (t, J=7.2 Hz, 4H), 1.97-1.94 (m, 1H), 1.73-1.63 (m, 1H), 1.49-1.40 (m, 2H), 0.87 (t, J=7.2 Hz, 3H); $^{13}$C NMR (100 MHz, $CDCl_3$): δ 166.01, 144.77, 140.29, 125.70, 122.90, 120.39, 118.96, 116.88, 108.54, 58.52, 58.08, 56.12, 53.59, 53.48, 48.28, 40.94, 26.46, 25.82, 25.09, 22.33, 11.85; Anal. Calcd for $C_{30}H_{40}N_6S$.5HCl.$CH_3OH$: C, 50.25; H, 6.61; N, 11.72. Found: C, 50.81; H, 7.00; N, 11.33.

(S)—$N^6$-(2-(4-(2-(9H-carbazol-9-yl)ethyl)piperazin-1-yl)ethyl)-$N^6$-propyl-4,5,6,7-tetrahydrobenzo[d]thiazole-2,6-diamine (101) (D-637)

Compound 99 (0.19 g, 0.59 mmol) was reacted with (−)-pramipexole (0.112 g, 0.53 mmol) and $NaBH(OAc)_3$ (0.25 g, 1.18 mmol) in $CH_2Cl_2$ (12 mL) according to procedure G. The crude product was purified by silica gel column chromatography (EtOAc:MeOH=4:1) to afford compound 101 (0.13 g, 47%). The compound was converted to HCl salt. $^1$H NMR (600 MHz, $CDCl_3$): δ 8.07 (d, J=7.8 Hz, 2H), 7.45 (t, J=7.8 Hz, 2H), 7.40 (d, J=7.8 Hz, 2H), 7.22 (t, J=7.8 Hz, 2H), 5.11 (bs, 2H), 4.41 (t, J=7.2 Hz, 2H), 3.03-2.98 (m, 1H), 2.74 (t, J=7.2 Hz, 2H), 2.69-2.48 (m, 14H), 2.45 (t, J=7.2 Hz, 4H), 1.96-1.94 (m, 1H), 1.71-1.64 (m, 1H), 1.48-1.41 (m, 2H), 0.87 (t, J=7.2 Hz, 3H); $^{13}$C NMR (150 MHz, $CDCl_3$): δ 165.85, 144.91, 140.28, 125.68, 122.89, 120.39, 118.95, 117.00, 108.53, 58.58, 58.08, 56.13, 53.63, 53.52, 48.33, 40.95, 26.52, 25.84, 25.10, 22.35, 11.85; $[\alpha]_D^{25}$=−19.8 (c=1.0 in $CH_2Cl_2$); Anal. Calcd for $C_{30}H_{40}N_6S$.4HCl.$2CH_3OH$: C, 52.89; H, 7.21; N, 11.57. Found: C, 53.16; H, 7.14; N, 11.68.

Evaluation of Binding Affinity and Functional Potencies at Dopamine D2 and D3 Receptors.

Binding affinity was evaluated by inhibition of [$^3$H] spiroperidol (15.0 Ci/mmol, Perkin-Elmer) binding to DA rD$_2$ and rD$_3$ receptors expressed in HEK-293 cells in a buffer containing 0.9% NaCl. Functional activity of test compounds in activating dopamine hD$_2$ and hD$_3$ receptors expressed in CHO cells was measured by stimulation of [$^{35}$S]GTPγS (1250 Ci/mmol, Perkin-Elmer) binding in comparison to stimulation by the full agonist DA. All these procedures were described by us previously.

In Vivo Study of (−)-91b, (−)-95a and (−)-95c in Parkinsonian Rats

Drugs and Chemicals.

The following commercially available drug was used in the experiment: reserpine hydrochloride (Alfa Aesar). The TFA salt of (−)-91b (D-636) and HBr salts of (−)-95a (D-653) and (−)-95c (D-656) were dissolved in water. Reserpine was dissolved in 20 μL of glacial acetic acid and further diluted with 5.5% glucose solution. The compounds for this study were administered in a volume of 0.1-0.2 mL for subcutaneous administration and 0.5-0.7 ml for interaperitoneal administration into each rat.

Animals.

In rodent studies, animals were male and female Sprague-Dawley rats from Harlan (Indianapolis, Ind.) weighing 220-225 g unless otherwise specified. Animals were maintained in sawdust-lined cages in a temperature and humidity controlled environment at 22±1° C. and 60±5% humidity, respectively. A 12 h light/dark cycle was maintained, with lights on from 6:00 a.m. to 6:00 p.m. They were group-housed with unrestricted access to food and water. All experiments were performed during the light component. All animal use procedures were in compliance with the Wayne State University Animal Investigation Committee, consistent with AALAC guidelines.

Reversal of Reserpine-Induced Hypolocomotion in Rats.

The ability of compounds (−)-91b, (−)-95a and (−)-95c to reverse reserpine-induced hypolocomotion was investigated according to a reported procedure. Reserpine (5.0 mg/kg, sc) was administered 18 h before the injection of drug or vehicle. The rats were placed individually in the chambers for 1 h for acclimatization before administration of the test drugs or vehicle. Immediately after administration of drug or vehicle, animals were individually placed in Opto-Varimex 4 animal activity monitor chamber (Columbus Instruments, Ohio, USA) to start measuring locomotor activity. Locomotion was monitored for 6 h. Consecutive interruption of two infrared beams, situated 50 cm apart and 4 cm above the cage floor, in the monitor chamber recorded movement. The data were presented as horizontal activity (HACTV). The effect of individual doses of drugs on locomotor activity was compared with respect to saline treated controls (mean±SEM). The data were analyzed by one-way analysis of variance (ANOVA) followed by Dunnett's post hoc test. The effect was considered significant if the difference from control group was observed at p<0.05.

Assessment of Anti-Oxidant Activity:

Cell Cultures and Treatments.

PC12 cells (ATCC CRL1721.1, Manassas, Va., USA), a rat adrenal pheochromocytoma cell line, were cultured in T-75 flasks (Greiner Bio One, Frickenhausen, Germany) and maintained in RPMI 1640 medium supplemented with 10% heat inactivated horse serum, 5% fetal bovine sérum, 100 U/ml penicillin, and 100 μg/mL streptomycin at 37° C. in 95% air/5% CO$_2$. Stock solutions of (−)-91b, (−)-95a and (−)-95c were prepared in dimethylsulfoxide (DMSO) and stored at −20° C., a stock solution of 6-Hydroxydopamine (6-OHDA) was stored at −80° C., a solution of 6-carboxy-2',7'-dichlorodihydroflourescence diacetate (carboxy-DCFDA) was prepared fresh in DMSO before addition. All stock solution were stored for the period of the experiments.

Measurement of Antioxidant Activity:

To determine the effects of (−)-91b, (−)-95a and (−)-95c in decreasing reactive oxygen species (ROS) in PC12 cells produced by the neurotoxin 6-OHDA, a quantitative fluorometric ROS assay was performed. PC12 cells were plated at 30,000 cells/well density in 100 μL media in 96-well black plates and incubated at 37° C. under 5% CO$_2$ atmosphere for 24 h. The cells were treated for 24 h with various concentrations of compounds (−)-91b, (−)-95a and (−)-95c. Then the drugs containing media were removed and replaced with DCFDA 20 μm for 30 min in an incubator (37° C., 5% CO$_2$). The DCFDA containing media was then removed and the cells were washed with PBS buffer to remove the traces of the dye. Fresh culture media was added followed by treatment with 75 μM of 6-OHDA alone for an additional 1 h under the same conditions. After incubation for 1 h, the fluorescence was measured using spectrophotometer fluorescence generated microplate reader (Biotek Epoch, Winooski, Vt., USA) at excitation 497 nm and emission at 527 nm. Data from at least three experiments were analyzed by one-way analysis of variance (ANOVA) followed by Tukey's multiple comparison post hoc test using GraphPad software (version 6, San Diego, Calif., USA). The specific fluorescence emission was calculated after subtraction of the DCFDA untreated control cells from the DCFDA treated cells for both the background and 1 h treatment conditions. This was followed by the division of the 1 h treatment data by the background activity which was determined from vials before treatment with 6-OHDA, to derive the final data point.

Assessment of Cell Viability:

Cell Cultures and Treatments.

PC12 cells (ATCC CRL1721.1, Manassas, Va., USA), a rat adrenal pheochromocytoma cell line, were cultured in T-75 flasks (Greiner Bio One, Frickenhausen, Germany) and maintained in RPMI 1640 medium supplemented with 10% heat inactivated horse serum, 5% fetal bovine serum, 100 U/ml penicillin, and 100 μg/mL streptomycin at 37° C. in 95% air/5% CO$_2$. Stock solutions of (−)-91b, (−)-95a, (−)-95c, and 6-hydroxydopamine (6-OHDA) were prepared in dimethylsulfoxide (DMSO) and aliquots were stored at −20° C. and −80° C., respectively. For all experiments assessing neuroprotective effects of the test compounds, PC12 cells were pretreated with indicated concentrations of (−)-91b, (−)-95a and (−)-95c for 24 h and then treated with 75 μM 6-OHDA for another 24 h. The control cells were treated with above media containing 0.01% DMSO only.

To determine the neuroprotective effects of (−)-91b, (−)-95a and (−)-95c in the presence of neurotoxin 6-OHDA, a quantitative colorimetric MTT assay was performed. PC12 cells were plated at 17000 cells/well density in 100 μL of media in 96-well plates and incubated at 37° C. under 5% CO$_2$ atmosphere for 24 h. Cells were treated with varying concentrations of the test compounds to determine their direct effect on cell viability. Neuroprotection experiments were conducted by treating cells for 24 h with varying concentrations of (−)-91b, (−)-95a and (−)-95c. Then the drug containing media was replaced with fresh culture media followed by treatment with 75 μM of 6-OHDA alone for an additional 24 h under the same condition. After incubation for 24 h, 5 mg/mL MTT solution (prepared in Dulbecco's phosphate-buffered saline) was added to the cells (to a final concentration of 0.5 mg/mL) and the plates were further incubated at 37° C. in 95% air/5% CO$_2$ atmosphere for 3-4 h to produce dark-blue formazan crystals. Afterward, the plates were centrifuged at 450 g for 10 min and the supernatants were carefully removed. Formazan crystals were dissolved by adding 100 µL of methanol:DMSO (1:1) mixture to each well and shaking gently at 400 rpm for 30 min at room temperature on a Thermomix R shaker (Eppendorf, Hamburg, Germany). The absorbance was measured on a microplate reader (Biotek Epoch, Winooski, Vt., USA) at 570 nm with background correction performed at 690 nm. Data from at least three experiments were analyzed using GraphPad software (version 6, San Diego, Calif., USA). Cell viability was defined as percentage reduction in absorbance compared to untreated controls. The data were analyzed by one-way analysis of variance (ANOVA) followed by Tukey's multiple comparison post hoc test.

Assessment of α-Synuclein Aggregation Inhibition Activity:

The experimental conditions were followed as described in our earlier publication. Briefly, α-syn fibrils were formed by incubating purified α-syn at a concentration of 5 mg/mL at 37° C. under constant agitation at 1000 rpm in a Thermomix R shaker (Eppendorf, Hamburg, Germany) for a period of 5 days. These fibrils at a concentration of 0.5% were used to seed the aggregation of α-syn at 1.25 mg/ml (86.45 µM) with or without compounds D636 or D653 at a concentration of 172.9 µM without agitation at 37° C. for a period of 30 days. Samples were collected at 0D and 30D. Thioflavin T (ThT) assay was performed using these samples as described previously to evaluate the extent of aggregation.

Further, the cytotoxicity of the aggregates formed was evaluated in PC12 cells. Briefly, PC12 cells were treated with α-syn aggregates such that its concentration is 10 µM. 24 h following treatments, viability was measured by MTT assay as described previously.

Additional Compounds

104. (2-Bromo-ethoxy)-tert-butyl-dimethyl-silane

A solution of bromoethanol 103 (1 mL, 14.1 mmol), imidazole (1.9 g, 27.9 mmol), and tert-butyldimethylsilyl chloride (2.1 g, 13.9 mmol) in $CH_2Cl_2$ (15 mL) was stirred at room temperature for 20 h. After the reaction was complete, water (20 mL) was added, and reaction mixture was extracted with $CH_2Cl_2$ (3×50 mL). The $CH_2Cl_2$ layer was dried over $Na_2SO_4$, filtered, and concentrated in vacuo. The resulting crude was purified by column chromatography using 5% ethyl acetate in hexanes to give compound 104 (2.85 g, 86%). $^1$H NMR (CDCl$_3$, 600 MHz): δ ppm 0.09 (s, 6H), 0.91 (s, 9H), 3.40 (t, J=6.6 Hz, 2H), 3.89 (t, J=6.6 Hz, 2H).

106. 1-[2-(tert-Butyl-dimethyl-silanyloxy)-ethyl]-piperazine

A suspension of piperazine 105 (2.3 g, 26.7 mmol), intermediate 104 (2.55 g, 10.7 mmol), and potassium carbonate (11 g, 79.6 mmol) in acetonitrile (35 mL) was refluxed at 80-90° C. for overnight. The reaction mixture was filtered, and the filtrate was condensed in vacuo. The residue was then diluted with ether, washed with water, dried over $Na_2SO_4$, filtered, and concentrated to produce intermediate 106 (2.19 g, 84%). $^1$H NMR (CDCl$_3$, 600 MHz): δ ppm 0.06 (s, 6H), 0.89 (s, 9H), 2.49-2.53 (m, 6H), 2.89 (t, J=4.8 Hz, 4H), 3.76 (t, J=6.6 Hz, 2H).

109. 4'-bromo-3,4-dimethoxy-1,1'-biphenyl

Into a mixture of starting material 107 (5.96 g, 25.3 mmol), Pd(PPh$_3$)$_4$ (0.73 g, 0.63 mmol), and K$_2$CO$_3$ (3.5 g, 25.3 mmol) in toluene/H$_2$O (20 mL/10 mL), a suspension of boronic acid 108 (2.3 g, 12.6 mmol) in ethanol (10 mL) was added and stirred at room temperature for 10 min. The reaction mixture was refluxed at 85-90° C. for 3 h. The solvent was partially evaporated, and the mixture was extracted with ethyl acetate (3×100 mL), which was then concentrated in vacuo after dried over Na$_2$SO$_4$. The resulting crude was purified by column chromatography using 5-10% ethyl acetate in hexanes to give compound 109 (2.89 g, 78%). $^1$H NMR (CDCl$_3$, 600 MHz): δ ppm 3.93 (s, 3H), 3.95 (s, 3H), 6.94 (d, J=8.4 Hz, 1H), 7.06 (d, J=1.8 Hz, 1H), 7.11 (dd, J=8.4, 2.4 Hz, 1H), 7.42-7.43 (m, 2H), 7.54 (dt, J=8.4, 1.8 Hz, 2H).

110. 1-(2-((tert-butyldimethylsilyl)oxy)ethyl)-4-(3',4'-dimethoxy-[1,1'-biphenyl]-4-yl)piperazine The mixture of intermediate 106 (3.33 g, 13.6 mmol), intermediate 109 (2 g, 6.8 mmol), BINAP (0.425 g, 0.68 mmol), and Cs$_2$CO$_3$ (6.67 g, 20.5 mmol) in toluene (60 mL) was degassed by bubbling N$_2$ for 5 min. Then Pd(OAc)$_2$ (115 mg, 0.51 mmol) was added quickly followed by degassing for another 5 min. The reaction mixture was refluxed at 110° C. for 24 h under inert condition. Afterward, it was cooled to room temperature, filtered through a pad of celite, washed with CH$_2$Cl$_2$, and concentrated in vacuo. The resulting crude was purified by column chromatography using 10-30% ethyl acetate in hexanes to give compound 110 (2.4 g, 77%). $^1$H NMR (CDCl$_3$, 600 MHz): δ ppm 0.80 (s, 6H), 0.91 (s, 9H), 2.60 (t, J=6.6 Hz, 2H), 2.71 (t, J=4.8 Hz, 4H), 3.24 (t, J=4.8 Hz, 4H), 3.81 (t, J=5.4 Hz, 2H), 3.91 (s, 3H), 3.94 (s, 3H), 6.91 (d, J=7.8 Hz, 1H), 6.97 (d, J=8.4 Hz, 2H), 7.07-7.11 (m, 2H), 7.46 (d, J=7.8 Hz, 2H).

111. 2-(4-(3',4'-dimethoxy-[1,1'-biphenyl]-4-yl)piperazin-1-yl)ethanol

Compound 110 (2 g, 4.4 mmol) was dissolved in THF (25 mL) and cooled to 0° C. TBAF (n-tetrabutylammonium fluoride) 1M in THF (8.76 mL, 8.76 mmol) was added at 0° C., and reaction stirred at room temperature for 2 h. After reaction was complete, saturated NaHCO$_3$ solution (50 mL) was added, and reaction mixture was extracted with CH$_2$Cl$_2$ (3×150 mL), which was then concentrated in vacuo. The resulting crude was purified by column chromatography using 0-5% methanol in CH$_2$Cl$_2$ to give compound 111 (1.34 g, 89%). $^1$H NMR (CDCl$_3$, 600 MHz): δ ppm 2.63 (t, J=5.4 Hz, 2H), 2.71 (t, J=5.4 Hz, 4H), 3.26 (t, J=4.8 Hz, 4H), 3.68 (t, J=5.4 Hz, 2H), 3.92 (s, 3H), 3.94 (s, 3H), 6.92 (d, J=8.4 Hz, 1H), 6.86 (d, J=9.0 Hz, 2H), 7.07-7.11 (m, 2H), 7.47 (d, J=9.0 Hz, 2H).

112. 2-(4-(3',4'-dimethoxy-[1,1'-biphenyl]-4-yl)piperazin-1-yl)acetaldehyde

A solution of DMSO (0.31 mL, 4.37 mmol) in CH$_2$Cl$_2$ (2 mL) was added into a round-bottom flask containing a stirring solution of oxalyl chloride (0.21 mL, 2.41 mmol) in CH$_2$Cl$_2$ (2 mL) at −78° C. The mixture was stirred for 0.5 h at the same temperature, and compound 111 (0.42 g, 1.23 mmol) in CH$_2$Cl$_2$ (3 mL) was added. The stirring of the reaction mixture was continued at −78° C. for another 0.5 h. Thereafter, Et$_3$N (1.38 mL, 9.90 mmol) was added, and the reaction was allowed to warm to room temperature and continued for another 1 h. The reaction mixture was quenched by the addition of a saturated solution of NaHCO$_3$ at 0° C. and was extracted with CH$_2$Cl$_2$ (3×100 mL). The combined organic layer was dried over Na$_2$SO$_4$, and the solvent was removed in vacuo to produce the crude, which was purified by column chromatography using ethyl acetate to give compound 112 (0.379 g, 91%). $^1$H NMR (600 MHz, CDCl$_3$): δ ppm 2.73 (t, J=4.8 Hz, 4H), 3.27 (s, 2H), 3.30 (t, J=4.8 Hz, 4H), 3.92 (s, 3H), 3.94 (s, 3H), 6.92 (d, J=8.4 Hz, 1H), 6.98 (d, J=9.0 Hz, 2H), 7.07-7.11 (m, 2H), 7.47 (d, J=9.0 Hz, 2H), 9.76 (s, 1H).

Procedure A. 114a. 2-(4-(3',4'-dimethoxy-[1,1'-biphenyl]-4-yl)piperazin-1-yl)-N,N-diethylethanamine Into a stirring solution of amine 113a (38.4 µL, 0.37 mmol) in CH$_2$Cl$_2$ (10 mL) was added aldehyde 112 (127 mg, 0.37 mmol), and the mixture stirred for 1.5 h. NaBH(OAc)$_3$ (0.158 g, 0.75 mmol) was then added portion-wise. The reaction was stirred for 48 h at room temperature. The reaction mixture was quenched with a sat. NaHCO$_3$ solution at 0° C. and extracted with CH$_2$Cl$_2$ (3×30 mL). The combined organic layer was dried over Na$_2$SO$_4$, and solvent was removed under reduced pressure. The crude product was purified by column chromatography using 0-10% MeOH in CH$_2$Cl$_2$ to give compound 114a (127 mg, 86%). $^1$H NMR (600 MHz, CDCl$_3$): δ ppm 1.08 (t, J=7.2 Hz, 6H), 2.59-2.73 (m, 12H), 3.25 (t, J=5.4 Hz, 4H), 3.91 (s, 3H), 3.94 (s, 3H), 6.91 (d, J=8.4 Hz, 1H), 6.96 (d, J=8.4 Hz, 2H), 7.07-7.11 (m, 2H), 7.46 (d, J=9.0 Hz, 2H).

114b. N-(2-(4-(3',4'-dimethoxy-[1,1'-biphenyl]-4-yl)piperazin-1-yl)ethyl)-N-isopropylpropan-2-amine Aldehyde 112 (194 mg, 0.57 mmol), amine 113b (80.5 µL, 0.57 mmol), and NaBH(OAc)$_3$ (0.242 g, 1.14 mmol) in CH$_2$Cl$_2$ (10 mL) were reacted using procedure A, and the resulting crude was purified by column chromatography using 0-10% MeOH in CH$_2$Cl$_2$ to give compound 114b (117 mg, 48%). $^1$H NMR (600 MHz, CDCl$_3$): δ ppm 1.08 (bs, 12H), 2.45-2.81 (m, 8H), 2.98-3.16 (m, 2H), 3.25 (t, J=4.2 Hz, 4H), 3.92 (s, 3H), 3.94 (s, 3H), 6.91 (d, J=8.4 Hz, 1H), 6.97 (d, J=9.0 Hz, 2H), 7.07-7.10 (m, 2H), 7.46 (d, J=8.4 Hz, 2H).

114c. 2-(4-(3',4'-dimethoxy-[1,1'-biphenyl]-4-yl)piperazin-1-yl)-N-(4-fluorobenzyl)ethanamine Aldehyde 112 (185 mg, 0.54 mmol), amine 113c (61.7 µL, 0.54 mmol), and NaBH(OAc)$_3$ (0.23 g, 1.09 mmol) in CH$_2$Cl$_2$ (10 mL) were reacted using procedure A, and the resulting crude was purified by column chromatography using 0-10% MeOH in CH$_2$Cl$_2$ to give compound 114c (73 mg, 30%). $^1$H NMR (600 MHz, CDCl$_3$): δ ppm 2.59 (t, J=6.0 Hz, 6H), 2.75 (t, J=6.6 Hz, 2H), 3.22 (t, J=4.8 Hz, 4H), 3.81 (s, 2H), 3.91 (s, 3H), 3.94 (s, 3H), 6.91 (d, J=8.4 Hz, 1H), 6.97 (d, J=8.4 Hz, 2H), 7.02 (t, J=8.4 Hz, 2H), 7.07-7.11 (m, 2H), 7.31 (dd, J=8.4, 5.4 Hz, 2H), 7.46 (d, J=8.4 Hz, 2H).

Procedure B. 115a. 4'-[4-(2-Diethylamino-ethyl)-piperazin-1-yl]-biphenyl-3,4-diol (D-690)

Compound 114a (44 mg, 0.11 mmol) was treated with 48% hydrobromic acid (2.5 mL) and refluxed for 6 h. HBr was removed to obtain the residue, which was then dissolved in MeOH and filtered through cotton. The filtrate was concentrated and washed with ether for three times followed drying to give the hydrobromide salt of compound 115a (63.5 mg, 89%). $^1$H NMR (600 MHz, CD$_3$OD): δ ppm 1.40 (t, J=7.2 Hz, 6H), 3.31-3.94 (m, 16H), 6.78 (d, J=7.8 Hz, 1H), 6.91 (d, J=8.4 Hz, 1H), 7.00 (d, J=2.4 Hz, 1H), 7.10-7.31 (m, 2H), 7.52 (d, J=8.4 Hz, 2H). Mp 198-200° C. Ana. (C$_{22}$H$_{38}$Br$_3$N$_3$O$_4$) C, H, N.

115b. 4'-[4-(2-Diisopropylamino-ethyl)-piperazin-1-yl]-biphenyl-3,4-diol (D-687)

Compound 114b (41 mg, 0.096 mmol) was treated with 48% hydrobromic acid (2.2 mL) and refluxed for 6 h by following procedure B. The crude was washed with ether for three times followed drying to give the hydrobromide salt of compound 115b (49.6 mg, 75%). $^1$H NMR (600 MHz, CD$_3$OD): δ ppm 1.46 (s, 6H), 1.47 (s, 6H), 3.34-3.90 (m, 14H), 6.79 (d, J=7.8 Hz, 1H), 6.90 (d, J=8.4 Hz, 1H), 7.00 (s, 1H), 7.18-7.28 (m, 2H), 7.51 (d, J=8.4 Hz, 2H). Mp 168-171° C. Ana. (C$_{24}$H$_{43}$Br$_3$N$_3$O$_{4.5}$) C, H, N.

115c. 4'-{4-[2-(4-Fluoro-benzylamino)-ethyl]-piperazin-1-yl}-biphenyl-3,4-diol (D-688)

Compound 114c (63 mg, 0.14 mmol) was treated with 48% hydrobromic acid (3.2 mL) and refluxed for 6 h by following procedure B. The crude was washed with ether for three times followed drying to give the hydrobromide salt of compound 115c (80.5 mg, 82%). $^1$H NMR (600 MHz, CD$_3$OD): δ ppm 3.59-3.72 (m, 12H), 4.39 (s, 2H), 6.82 (d, J=7.8 Hz, 1H), 6.93 (d, J=6.6 Hz, 1H), 7.03 (d, J=1.8 Hz, 1H), 7.20-7.25 (m, 4H), 7.53 (d, J=9.0 Hz, 2H), 7.69-7.71 (m, 2H). Mp 200-203° C. Ana. (C$_{25}$H$_{35}$Br$_3$FN$_3$O$_4$) C, H, N.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A compound having formula I for treating a neurodegenerative and other related CNS diseases:

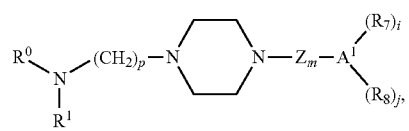

or a pharmaceutically acceptable salt or ester or carbamate thereof,
wherein
R$^0$ is an optionally substituted C$_{1-8}$ alkyl, C$_{1-8}$ alkoxyl, C$_{2-8}$ alkenyl, C$_{2-8}$ alkynyl, C$_{4-8}$ cycloalkyl, C$_{4-8}$ cycloalkenyl, C$_{6-10}$ aryl,

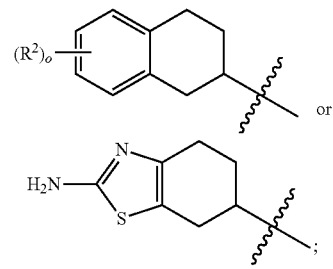

$R^1$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl;

$R^2$ are halo, hydroxyl, $C_{1-4}$ alkoxyl, or $C_{1-8}$ alkyl;

$R^7$, $R^8$ are each independently oxo, $C_{1-8}$ alkyl, $C_{1-8}$ alkoxyl, $C_{2-8}$ alkenyl, $C_{2-10}$ alkynyl, $C_{5-7}$ cycloalkyl, $C_{5-7}$ cycloalkenyl, or halo;

$A^1$ is

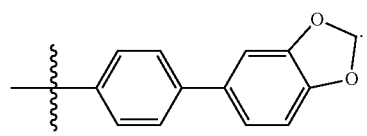 [SMILES: *c1ccc(-c2ccc3c(c2)OCO3)cc1]

p is an integer from 1 to 6;

$Z_m$ is absent or a divalent linking moiety in which Z is repeated m times;

m is an integer from 0 to 5;

j are each independently 0, 1, 2, or 3; and o is 0, 1, 2, 3, or 4.

2. The compound of claim 1 wherein i and j are 0.

3. The compound of claim 1 wherein $R^1$ is substituted with a component selected from the group consisting of, $C_{1-4}$ acyloxy, $C_{1-4}$ acyl, —C(O)—$R^4$, $R^5$—NH—SO$_2$—NR$^4_r$, $R^5$—NH—C(O)—$R^4$; —$R^5$—NR$^4_r$, and —$R^5$—Ar where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

$R^5$ is $C_{2-8}$ alkenyl;

r is 2 or 3; and

Ar is a $C_{6-10}$ aryl ring system, optionally including one or more heteroatoms or $C_{5-10}$ heteroaryl; with the proviso that when r is 3, the nitrogen of the NR$^4_r$ group bears a positive formal charge.

4. The compound of claim 1 wherein $R^1$ is substituted with —$R^5$—Ar where $R^5$ is $C_{2-8}$ alkenyl and Ar is an optionally substituted phenyl, thienyl, pyridyl, bipyridyl, biphenylyl, or naphthyl.

5. The compound of claim 1 wherein $A^1$ is directly bonded to a nitrogen atom of the piperazinyl group.

6. The compound of claim 4 wherein Z is —CH$_2$—, —CO—, N—CH$_2$— or N—CO—.

7. The compound of claim 1 wherein $R^2$ are hydroxyl or $C_{1-4}$ alkoxyl.

8. A compound having formula I for treating a neurodegenerative and other related CNS diseases:

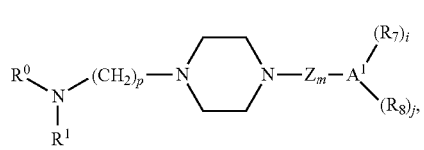

or a pharmaceutically acceptable salt or ester or carbamate thereof, wherein $R^0$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, $C_{6-10}$ aryl,

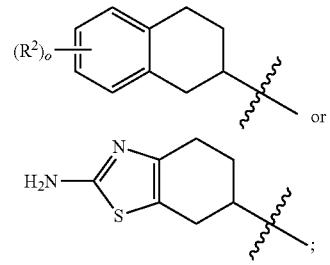

$R^1$ is an optionally substituted $C_{1-8}$ alkyl, $C_{1-8}$ alkoxyl, $C_{2-8}$ alkenyl, $C_{2-8}$ alkynyl, $C_{4-8}$ cycloalkyl, $C_{4-8}$ cycloalkenyl, or $C_{6-10}$ aryl;

$R^2$ are hydroxyl, $C_{1-4}$ alkyl, $C_{1-4}$ alkoxyl, or $C_{1-8}$ alkyl;

$R^7$, $R^8$ are each independently oxo, $C_{1-8}$ alkyl, $C_{2-8}$ alkenyl, $C_{2-10}$ alkynyl, $C_{5-7}$ cycloalkyl, $C_{5-7}$ cycloalkenyl, or halo with at least one of $R^7$ and one of $R^8$ combined as —OCH$_2$O—;

$A^1$ is a $C_{6-12}$ aryl group or $C_{5-12}$ heteroaryl group;

p is an integer from 1 to 6;

$Z_m$ is absent or a divalent linking moiety in which Z is repeated m times;

m is an integer from 0 to 5;

i, j are each independently 1, 2, or 3; and o is 0, 1, 2, 3, or 4.

9. The compound of claim 8 wherein $A^1$ is:

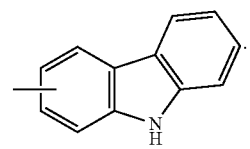

10. The compound of claim 8 wherein $A^1$ is:

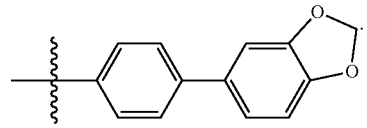 [SMILES: *c1ccc(-c2ccc3c(c2)OCO3)cc1]

11. The compound of claim 8 wherein $R^1$ is substituted with a component selected from the group consisting of, $C_{1-4}$ acyloxy, $C_{1-4}$ acyl, —C(O)—$R^4$, $R^5$—NH—SO$_2$—NR$^4_r$, $R^5$—NH—C(O)—$R^4$; —$R^5$—NR$^4_r$, and —$R^5$—Ar where $R^4$ is H, $C_{1-8}$ alkyl, $C_{2-8}$ alkenyl, $C_{4-8}$ cycloalkyl, $C_{4-8}$ cycloalkenyl, or $C_{6-10}$ aryl;

$R^5$ is $C_{2-8}$ alkenyl;

r is 2 or 3; and

Ar is a $C_{6-10}$ aryl ring system, optionally including one or more heteroatoms or $C_{5-10}$ heteroaryl; with the proviso that when r is 3, the nitrogen of the NR$^4_r$ group bears a positive formal charge.

12. The compound of claim 8 wherein $R^1$ is substituted with —$R^5$—Ar where $R^5$ is $C_{2-8}$ alkenyl and Ar is an optionally substituted phenyl, thienyl, pyridyl, bipyridyl, biphenylyl, or naphthyl.

13. The compound of claim 8 wherein $A^1$ is directly bonded to a nitrogen atom of the piperazinyl group.

14. The compound of claim 8 wherein Z is —CH$_2$—, —CO—, —N—CH$_2$— or —N—CO—.

15. The compound of claim 8 wherein $R^2$ are hydroxyl or C$_{1-4}$ alkoxyl.

16. The compound of claim 8 having a formula selected from the group consisting of:

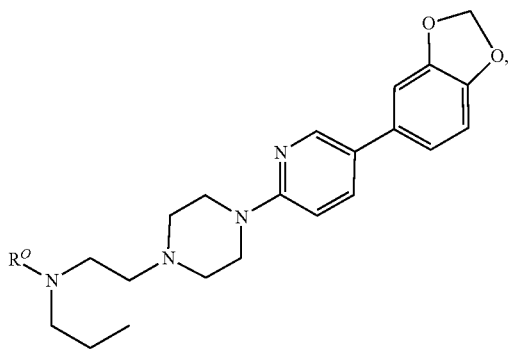

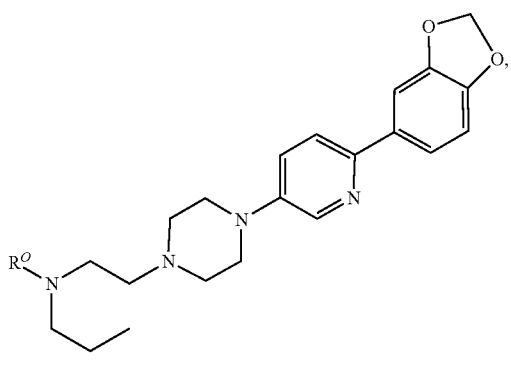

pharmaceutically acceptable salts thereof, esters thereof, and carbamates thereof.

17. The compound of claim 8 having a formula selected from the group consisting of:

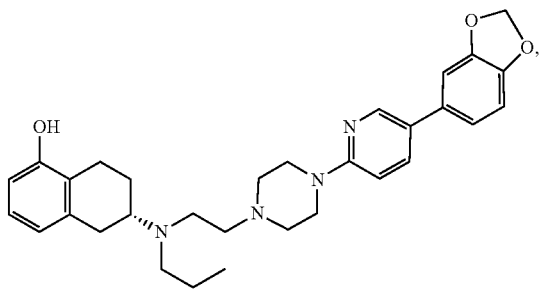

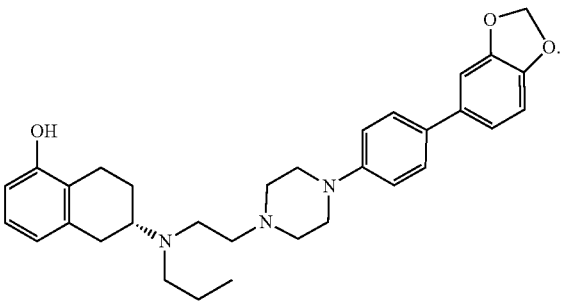 [SMILES: CCCN(CCN1CCN(c2ccc(-c3ccc4c(c3)OCO4)cc2)CC1)[C@H]1CCc2c(O)cccc2C1]

pharmaceutically acceptable salts thereof, esters thereof, and carbamates thereof.

18. A compound having the following formula:

or a pharmaceutically acceptable salt or ester or carbamate thereof.

* * * * *

UNITED STATES PATENT AND TRADEMARK OFFICE
CERTIFICATE OF CORRECTION

PATENT NO. : 10,874,669 B2
APPLICATION NO. : 16/124974
DATED : December 29, 2020
INVENTOR(S) : Aloke K. Dutta et al.

It is certified that error appears in the above-identified patent and that said Letters Patent is hereby corrected as shown below:

In the Claims

Column 59, Lines 21-22, Claim 1:
After "m is an integer from 0 to 5;"
Delete "j are each independently 0, 1, 2, or 3 and" and
Insert -- i, j are each independently 0, 1, 2, or 3; and --

Signed and Sealed this
Twenty-sixth Day of April, 2022

Katherine Kelly Vidal
*Director of the United States Patent and Trademark Office*